(12) United States Patent
Simpson et al.

(10) Patent No.: US 11,478,457 B2
(45) Date of Patent: Oct. 25, 2022

(54) CASTRATION-RESISTANT PROSTATE CANCER

(71) Applicant: NUtech Ventures, Lincoln, NE (US)

(72) Inventors: Melanie A. Simpson, Lincoln, NE (US); Joseph Barycki, Lincoln, NE (US)

(73) Assignee: NUtech Ventures, Lincoln, NE (US)

( * ) Notice: Subject to any disclaimer, the term of this patent is extended or adjusted under 35 U.S.C. 154(b) by 172 days.

(21) Appl. No.: 15/136,419

(22) Filed: Apr. 22, 2016

(65) Prior Publication Data

US 2016/0310528 A1    Oct. 27, 2016

Related U.S. Application Data

(60) Provisional application No. 62/151,869, filed on Apr. 23, 2015.

(51) Int. Cl.
| | |
|---|---|
| *A61K 31/4245* | (2006.01) |
| *A61K 31/381* | (2006.01) |
| *A61K 31/198* | (2006.01) |
| *A61K 31/428* | (2006.01) |
| *A61K 31/341* | (2006.01) |
| *A61K 31/426* | (2006.01) |
| *A61K 31/421* | (2006.01) |
| *A61K 31/4025* | (2006.01) |
| *A61K 31/415* | (2006.01) |
| *A61K 31/50* | (2006.01) |
| *A61K 31/47* | (2006.01) |
| *A61K 31/41* | (2006.01) |
| *A61K 31/192* | (2006.01) |
| *A61K 31/416* | (2006.01) |
| *A61K 31/4045* | (2006.01) |
| *A61K 31/165* | (2006.01) |
| *A61K 31/136* | (2006.01) |
| *A61K 31/277* | (2006.01) |
| *A61K 31/433* | (2006.01) |
| *A61K 31/145* | (2006.01) |
| *A61K 31/4709* | (2006.01) |
| *A61K 31/352* | (2006.01) |

(Continued)

(52) U.S. Cl.
CPC ........ *A61K 31/4245* (2013.01); *A61K 31/075* (2013.01); *A61K 31/09* (2013.01); *A61K 31/122* (2013.01); *A61K 31/136* (2013.01); *A61K 31/145* (2013.01); *A61K 31/165* (2013.01); *A61K 31/17* (2013.01); *A61K 31/192* (2013.01); *A61K 31/198* (2013.01); *A61K 31/277* (2013.01); *A61K 31/282* (2013.01); *A61K 31/305* (2013.01); *A61K 31/341* (2013.01); *A61K 31/352* (2013.01); *A61K 31/357* (2013.01); *A61K 31/381* (2013.01); *A61K 31/409* (2013.01); *A61K 31/4025* (2013.01); *A61K 31/4045* (2013.01); *A61K 31/41* (2013.01); *A61K 31/415* (2013.01); *A61K 31/416* (2013.01); *A61K 31/4184* (2013.01); *A61K 31/421* (2013.01); *A61K 31/426* (2013.01); *A61K 31/428* (2013.01); *A61K 31/433* (2013.01); *A61K 31/4365* (2013.01); *A61K 31/444* (2013.01); *A61K 31/47* (2013.01); *A61K 31/4709* (2013.01); *A61K 31/50* (2013.01); *A61K 31/5025* (2013.01); *A61K 31/519* (2013.01); *A61K 31/5377* (2013.01); *A61K 31/7034* (2013.01); *A61K 45/06* (2013.01); *A61P 35/00* (2018.01); *C12Q 1/32* (2013.01)

(58) Field of Classification Search
CPC .... A61K 31/075; A61K 31/09; A61K 31/122; A61K 31/136; A61K 31/145; A61K 31/165; A61K 31/17; A61K 31/192; A61K 31/198; A61K 31/277; A61K 31/282; A61K 31/305; A61K 31/341; A61K 31/352; A61K 31/357; A61K 31/381; A61K 31/4025; A61K 31/4045; A61K 31/409; A61K 31/41; A61K 31/415; A61K 31/416; A61K 31/4184; A61K 31/421; A61K 31/4245; A61K 31/426; A61K 31/428; A61K 31/433; A61K 31/4365; A61K 31/444; A61K 31/47; A61K 31/4709; A61K 31/50; A61K 31/5025; A61K 31/519; A61K 31/5377; A61K 31/7034; A61K 45/06; A61P 13/08; A61P 35/00; C12Q 1/32
See application file for complete search history.

(56) References Cited

U.S. PATENT DOCUMENTS 8,106,037 B2    1/2012  Rubin et al.
2004/0204435 A1 * 10/2004  Liehr ................. A61K 31/70
                                                        514/283

(Continued)

FOREIGN PATENT DOCUMENTS

WO    WO 2005/019190 A2 *  3/2005

OTHER PUBLICATIONS

Batog et al. 2000, vol. 36 No. 1, Chemistry of Heterocyclic Compounds pp. 91-100.*

(Continued)

*Primary Examiner* — Kara R McMillian
(74) *Attorney, Agent, or Firm* — Fish & Richardson P.C.

(57) ABSTRACT

This invention relates to inhibitors of UDP-glucose dehydrogenase, and more particularly to UDP-glucose dehydrogenase inhibitors that are useful in the treatment of prostate cancer. Methods of inhibiting UDP-glucose dehydrogenase and improving the efficacy of additional prostate cancer therapies are also provided.

18 Claims, 19 Drawing Sheets

(51) Int. Cl.
| | |
|---|---|
| A61K 31/5377 | (2006.01) |
| A61K 31/5025 | (2006.01) |
| A61K 31/09 | (2006.01) |
| A61K 31/075 | (2006.01) |
| A61K 31/4365 | (2006.01) |
| A61K 31/444 | (2006.01) |
| A61K 31/357 | (2006.01) |
| A61K 31/4184 | (2006.01) |
| A61K 31/519 | (2006.01) |
| A61K 31/17 | (2006.01) |
| A61K 31/122 | (2006.01) |
| A61K 31/305 | (2006.01) |
| A61K 31/409 | (2006.01) |
| A61K 31/282 | (2006.01) |
| A61K 31/7034 | (2006.01) |
| A61K 45/06 | (2006.01) |
| C12Q 1/32 | (2006.01) |
| A61P 35/00 | (2006.01) |

(56) References Cited

U.S. PATENT DOCUMENTS

| | | | |
|---|---|---|---|
| 2008/0020973 A1* | 1/2008 | Stivers | G01N 33/542 |
| | | | 514/711 |
| 2009/0291967 A1* | 11/2009 | Gupta | C07D 409/04 |
| | | | 514/255.05 |
| 2010/0099683 A1 | 4/2010 | Tomkinson et al. | |
| 2012/0034250 A1 | 2/2012 | Shirakami et al. | |
| 2014/0011767 A1 | 1/2014 | Yang et al. | |

OTHER PUBLICATIONS

Egger et al. 2010, Biochemical Society Transactions, vol. 38, part 5, pp. 1378-1385 (Year: 2010).*

Buonerba et al. (Cancer Chemother. Pharmacol. 2011, 67:1455-1461). (Year: 2011).*

Loriot et al. (Annals of Oncology, 20, 2009, pp. 703-708). (Year: 2009).*

Huang et al. (Int. J. Cancer, 2010 126(2), 315-327). (Year: 2010).*

Sengupta et al. Indian Journal of Chemistry, vol. 47B, Mar. 2008, pp. 460-462. (Year: 2008).*

Fraser et al., "Hyaluronan: its nature, distribution, functions and turnover," J. Intern. Med., 1997, 242: 27-33.

Guillemette C., "Pharmacogenomics of human UDP-glucuronosyltransferase enzymes," Pharmacogenomics J., 2003, 3:136-158.

Huang et al., "UDP-glucose dehydrogenase as a novel field-specific candidate biomarker of prostate cancer," International Journal of Cancer, 2010, 126(2), 315-327.

Hyde et al., "UDP-glucose Dehydrogenase Activity and Optimal Downstream Cellular Function Require Dynamic Reorganization at the Dimer-Dimer Subunit Interfaces," Journal of Biological Chemistry, Dec. 2013, 288(49): 35049-35057.

International Search Report and Written Opinion in International Application No. PCT/US2016/028936, dated Jul. 27, 2016, 12 pages.

King et al., "Characterization of Rat and Human UDP-Glucuronosyltransferases Responsible for the in Vitro Glucuronidation of Diclofenac," Toxicol. Sci., 2001, 61(1):49-53.

Prydz et al., "Synthesis and sorting of proteoglycans," J. Cell Sci., 2000, 113:193-205.

Wei et al., "Androgen-stimulated UDP-glucose dehydrogenase expression limits prostate androgen availability without impacting hyaluronan levels," Cancer Res., Mar. 2009, 69(6): 2332-2339.

International Preliminary Report on Patentability in International Application No. PCT/US2016/028936, dated Oct. 24, 2017, 7 pages.

* cited by examiner

FIG. 7A
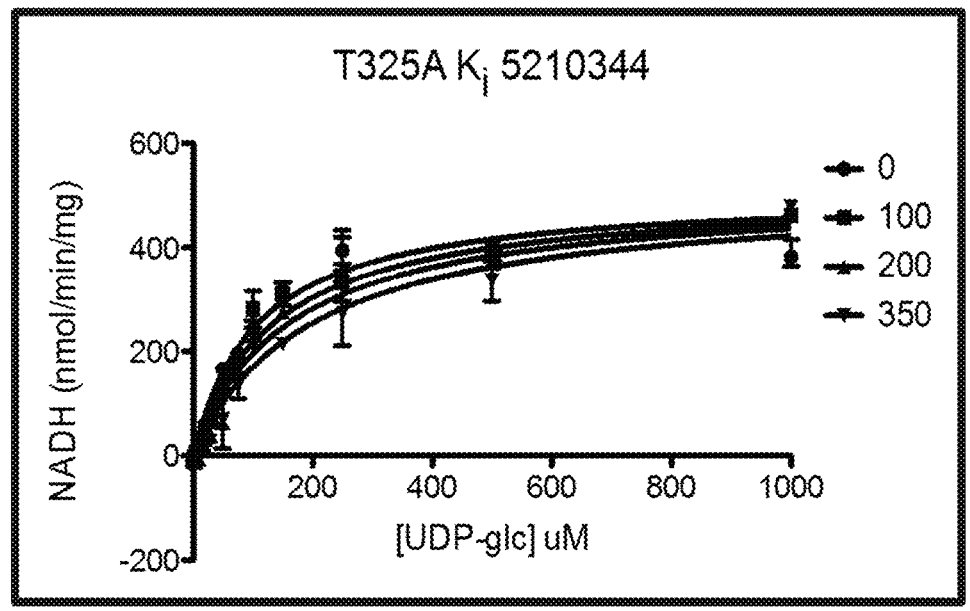
FIG. 7B
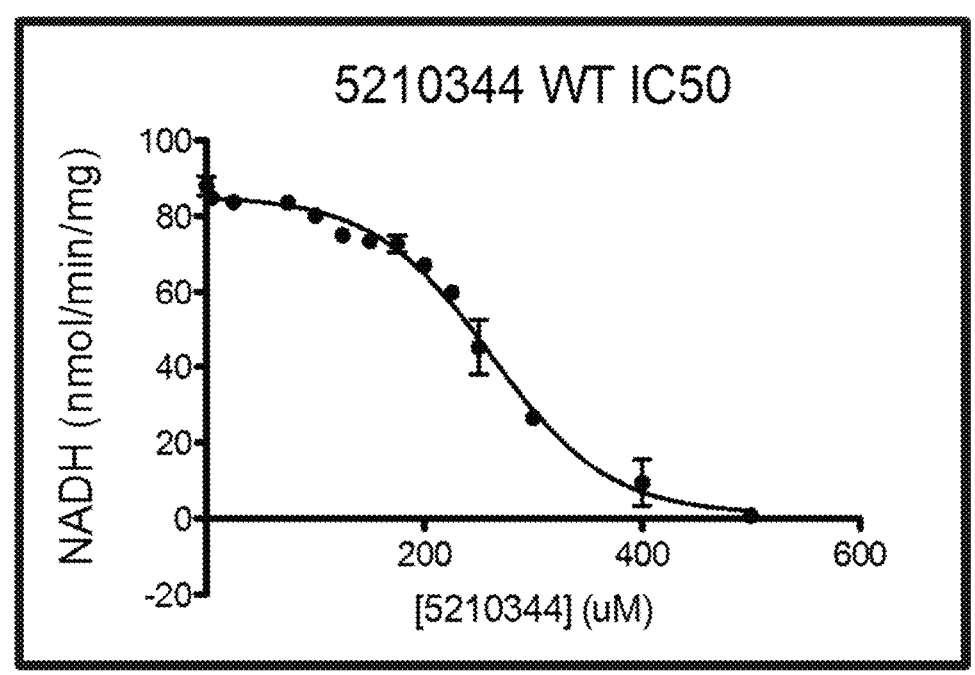
FIGs. 7A-7B

FIG. 12

CASTRATION-RESISTANT PROSTATE CANCER

CROSS-REFERENCE TO RELATED APPLICATIONS

This application claims the benefit of U.S. Provisional Application Ser. No. 62/151,869, filed Apr. 23, 2015, the disclosure of which is incorporated herein by reference in its entirety.

FEDERALLY SPONSORED RESEARCH OR DEVELOPMENT

This invention was made with Government support under Grant Nos. 2012-31100-06031, 2013-31100-06031, 2014-31100-06031, and 2015-31100-06031 awarded by the United States Department of Agriculture and the National Institute of Food and Agriculture. The Government has certain rights in the invention.

TECHNICAL FIELD

This invention relates to inhibitors of UDP-glucose dehydrogenase, and more particularly to UDP-glucose dehydrogenase inhibitors that are useful in the treatment of prostate cancer.

BACKGROUND

Prostate cancer is the most frequently diagnosed cancer among men in the United States, and the second most frequent cause of cancer death. One of the first line treatments for inoperable or locally advanced cancers is androgen deprivation therapy, since the cells of the prostate normally depend on circulating androgen hormones for survival. This treatment fails in approximately 20% of cases treated this way, and leads to even more aggressive cancer, termed castration resistant prostate cancer (CRPC).

SUMMARY

The present application provides, inter alia, a method of treating prostate cancer, comprising administering to a patient in need thereof a therapeutically effective amount of a compound provided in Table 1, or a pharmaceutically acceptable salt thereof.

In some embodiments, the prostate cancer is castration resistant prostate cancer (CRPC).

In some embodiments, the compound is administered in combination with one or more additional therapies. In some embodiments, at least one of the one or more additional therapies comprises administration of a chemotherapeutic agent. In some embodiments, at least one of the one or more additional therapeutic agents comprises androgen deprivation therapy. In some embodiments, the compound is administered prior to the one or more additional therapies. In some embodiments, the compound is 2,2'-[1-(4-amino-1,2,5-oxadiazol-3-yl)-1H-1,2,3-triazole-4,5-diyl]di(2-butanol) (1), or a pharmaceutically acceptable salt thereof. In some embodiments, the compound is 3-[5-(2-thienyl)-2-furyl]propanoic acid (31), or a pharmaceutically acceptable salt thereof.

The present application further provides a method of modulating an activity of UDP-glucose dehydrogenase (UGDH) in a cell, the method comprising contacting the cell with an effective amount of a compound provided in Table 1, or a pharmaceutically acceptable salt thereof.

In some embodiments, the modulating an activity of UDP-glucose dehydrogenase (UGDH) comprises inhibiting UDP-glucose dehydrogenase (UGDH).

In some embodiments, the compound is 2,2'-[1-(4-amino-1,2,5-oxadiazol-3-yl)-1H-1,2,3-triazole-4,5-diyl]di(2-butanol) (1), or a pharmaceutically acceptable salt thereof. In some embodiments, the compound is 3-[5-(2-thienyl)-2-furyl]propanoic acid (31), or a pharmaceutically acceptable salt thereof.

The present application further provides a method of treating a prostate cancer mediated by UDP-glucose dehydrogenase (UGDH) in a patient in need thereof, the method comprising administering a therapeutically effective amount of a compound provided in Table 1, or a pharmaceutically acceptable salt thereof.

In some embodiments, the prostate cancer is castration resistant prostate cancer (CRPC).

In some embodiments, the compound is 2,2'-[1-(4-amino-1,2,5-oxadiazol-3-yl)-1H-1,2,3-triazole-4,5-diyl]di(2-butanol) (1), or a pharmaceutically acceptable salt thereof. In some embodiments, the compound is 3-[5-(2-thienyl)-2-furyl]propanoic acid (31), or a pharmaceutically acceptable salt thereof.

The present application further provides a method of predicting patient response to prostate cancer therapy, comprising:

a) obtaining a biopsy sample from the patient, wherein the biopsy sample comprises prostate cancer cells and non-cancerous tissue cells; and b) comparing the UDP-glucose dehydrogenase (UGDH) expression in the prostate cancer cells and the non-cancerous tissue cells;

wherein if the UDP-glucose dehydrogenase (UGDH) expression is greater in the prostate cancer cells compared to the UDP-glucose dehydrogenase (UGDH) expression in the non-cancerous tissue cells, then the patient is more likely to respond to the prostate cancer therapy.

In some embodiments, the prostate cancer is castration resistant prostate cancer (CRPC).

In some embodiments, the comparing comprises determining the ratio of UDP-glucose dehydrogenase (UGDH) expression in the prostate cancer cells and UDP-glucose dehydrogenase (UGDH) expression in the non-cancerous tissue cells.

In some embodiments, the prostate cancer therapy comprises androgen deprivation therapy. In some embodiments, the prostate cancer therapy is androgen deprivation therapy.

The present application further provides a method of treating a prostate cancer mediated by UDP-glucose dehydrogenase (UGDH) in a patient in need thereof, the method comprising:

a) obtaining a biopsy sample from the patient, wherein the biopsy sample comprises prostate cancer cells and non-cancerous tissue cells;

b) comparing the UDP-glucose dehydrogenase (UGDH) expression in the prostate cancer cells and the non-cancerous tissue cells; and c) if the prostate cancer is determined to be associated with one or more of overexpression and amplification of UDP-glucose dehydrogenase (UGDH) in the prostate cancer cells, administering a therapeutically effective amount of a compound provided in Table 1, or a pharmaceutically acceptable salt thereof.

In some embodiments, the comparing comprises determining the ratio of UDP-glucose dehydrogenase (UGDH)

expression in the prostate cancer cells and UDP-glucose dehydrogenase (UGDH) expression in the non-cancerous tissue cells.

In some embodiments, the prostate cancer is castration resistant prostate cancer (CRPC).

In some embodiments, the method further comprises administration of one or more additional therapies. In some embodiments, at least one of the one or more additional therapies comprises administration of a chemotherapeutic agent. In some embodiments, at least one of the one or more additional therapeutic agents comprises administration of androgen deprivation therapy.

In some embodiments, the compound is 2,2'-[1-(4-amino-1,2,5-oxadiazol-3-yl)-1H-1,2,3-triazole-4,5-diyl]di(2-butanol) (1), or a pharmaceutically acceptable salt thereof. In some embodiments, the compound is 3-[5-(2-thienyl)-2-furyl]propanoic acid (31), or a pharmaceutically acceptable salt thereof.

The present application further provides a method of improving the efficacy of androgen deprivation therapy in a patient, comprising administering to the patient a therapeutically effective amount of a UDP-glucose dehydrogenase (UGDH) inhibitor.

In some embodiments, the androgen deprivation therapy is administered for the treatment of prostate cancer in the patient. In some embodiments, the prostate cancer is castration resistant prostate cancer (CRPC).

In some embodiments, the UDP-glucose dehydrogenase (UGDH) inhibitor is selected from a compound provided in Table 1, or a pharmaceutically acceptable salt thereof. In some embodiments, the compound is 2,2'-[1-(4-amino-1,2,5-oxadiazol-3-yl)-1H-1,2,3-triazole-4,5-diyl]di(2-butanol) (1), or a pharmaceutically acceptable salt thereof. In some embodiments, the compound is 3-[5-(2-thienyl)-2-furyl]propanoic acid (31), or a pharmaceutically acceptable salt thereof.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

DESCRIPTION OF DRAWINGS

FIG. 7A-7E show kinetic characterization of inhibitors (1) (i.e. 5210344) and (31) (i.e., 6847944).

FIG. 12 illustrates the effects of inhibitor (1) and (31) on trypsin digestion of WT and mutant UGDH.

DETAILED DESCRIPTION

Figure 1:
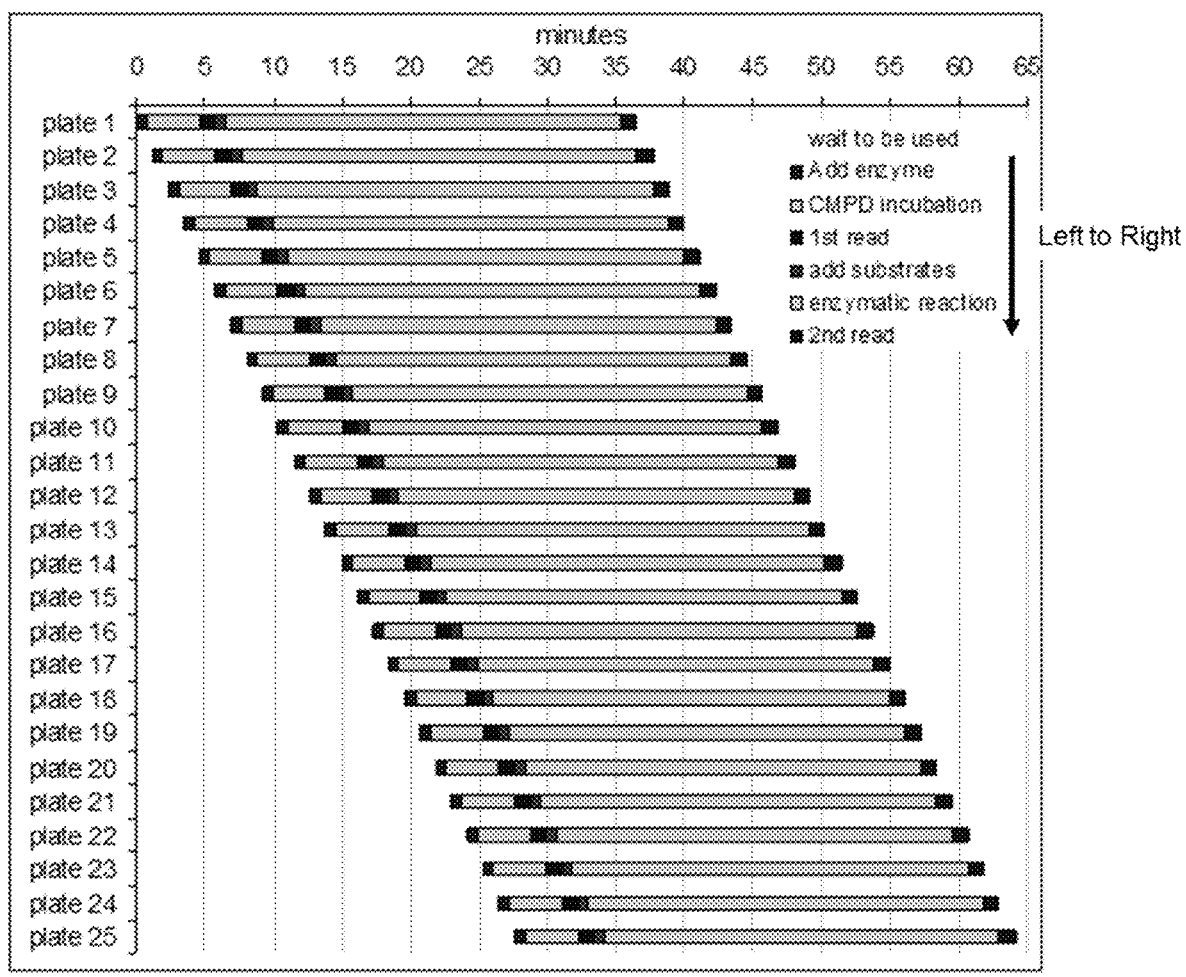
FIG. 1 shows a Gantt chart providing representative timing of the assay of Example 1.

UDP-glucose dehydrogenase (UGDH) catalyzes the $NAD^+$-dependent, two-step oxidation of UDP-glucose to UDP-glucuronic acid, an essential precursor for hyaluronan synthesis by HAS enzymes, other glycosaminoglycan/proteoglycan production in the Golgi, and glucuronidation of steroid hormones by UGTs for solubilization and excretion (see, e.g., Prydz et al., *J. Cell Sci.* 2000, 113, 193-205; Fraser et al., *J. Intern. Med.* 1997, 242, 27-33; Guillemette C., *Pharmacogenomics J.* 2003, 3, 136-158; and King et al., *Toxicol. Sci.* 2001, 61, 49-53). High levels of UGDH expression are specific to the liver and prostate in males, and prostate tumor progression has been correlated with a loss of UGDH regulation. Accordingly, the present application provides inhibitors of UGDH that are useful in the treatment of prostate cancer and methods for predicting the efficacy of androgen deprivation therapy.

Definitions

For the terms "for example" and "such as" and grammatical equivalences thereof, the phrase "and without limitation" is understood to follow unless explicitly stated otherwise. As used herein, the term "about" is meant to account for variations due to experimental error. All measurements reported herein are understood to be modified by the term "about", whether or not the term is explicitly used, unless explicitly stated otherwise. As used herein, the singular forms "a," "an," and "the" include plural referents unless the context clearly dictates otherwise.

A "therapeutically effective amount" of a conjugate with respect to the subject method of treatment, refers to an amount of the conjugate(s) in a preparation which, when administered as part of a desired dosage regimen (to a patient, e.g., a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment.

As used herein, the term "treating" or "treatment" includes reversing, reducing, or arresting the symptoms, clinical signs, and underlying pathology of a condition in manner to improve or stabilize a patient's condition.

Compounds and Pharmaceutical Compositions

The present application provides, inter alia, compounds that are useful as UDP-glucose dehydrogenase (UGDH)

inhibitors. In some embodiments, the compound is 2,2'-[1-(4-amino-1,2,5-oxadiazol-3-yl)-1H-1,2,3-triazole-4,5-diyl]di(2-butanol) (1), or a pharmaceutically acceptable salt thereof. In some embodiments, the compound is 3-[5-(2-thienyl)-2-furyl]propanoic acid (31), or a pharmaceutically acceptable salt thereof. In some embodiments, the compound 2,2'-[1-(4-amino-1,2,5-oxadiazol-3-yl)-1H-1,2,3-triazole-4,5-diyl]di(2-butanol) (1) (i.e., compound (1) or inhibitor (1)) is also referred to as inhibitor 5210344. In some embodiments, the compound 3-[5-(2-thienyl)-2-furyl]propanoic acid (31) (i.e. compound (31) or inhibitor (31)) is also referred to as inhibitor 6847944.

In some embodiments, a compound is selected from the group provided in Table 1.

TABLE 1

List of Compounds

| Compound # | Name | Structure |
|---|---|---|
| 1 | 2,2'-[1-(4-amino-1,2,5-oxadiazol-3-yl)-1H-1,2,3-triazole-4,5-diyl]di(2-butanol) | 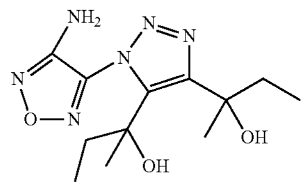 [SMILES: CCC(C)(O)c1nnn(-c2nonc2N)c1C(C)(O)CC] |
| 2 | 2-[1-(4-amino-1,2,5-oxadiazol-3-yl)-5-(2-hydroxypropan-2-yl)-1,2,3-triazol-4-yl]propan-2-ol | 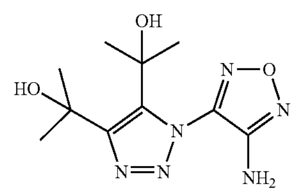 [SMILES: CC(C)(O)c1nnn(-c2nonc2N)c1C(C)(C)O] |
| 3 | 1-[1-(4-amino-1,2,5-oxadiazol-3-yl)-5-methyl-1,2,3-triazol-4-yl]ethanol | 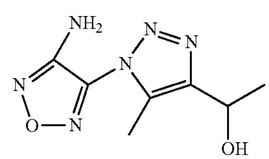 |
| 4 | [3-(4-amino-1,2,5-oxadiazol-3-yl)-1,2,3-triazol-4-yl]methanol | 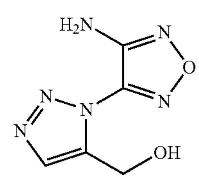 [SMILES: Nc1nonc1-n1nncc1CO] |
| 5 | [1-(4-amino-1,2,5-oxadiazol-3-yl)-1H-1,2,3-triazol-4-yl]methanol | 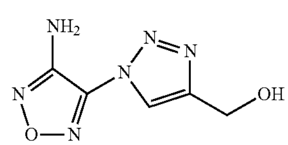 [SMILES: Nc1nonc1-n1cc(CO)nn1] |
| 6 | 1-[1-(4-amino-1,2,5-oxadiazol-3-yl)-1,2,3-triazol-4-yl]ethanol | 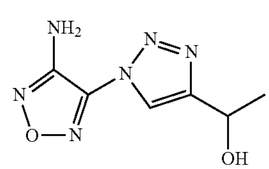 |
| 7 | 2-[1-(4-amino-1,2,5-oxadiazol-3-yl)-1,2,3-triazol-4-yl]propan-2-ol | 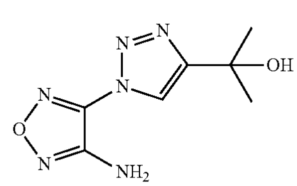 |

TABLE 1-continued

List of Compounds

| Compound # | Name | Structure |
|---|---|---|
| 8 | 4-(5-ethyl-1,2,3-triazol-1-yl)-1,2,5-oxadiazol-3-amine | 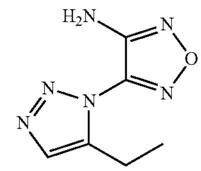 |
| 9 | methyl 1-(4-amino-1,2,5-oxadiazol-3-yl)-5-tert-butyl-1,2,3-triazole-4-carboxylate | 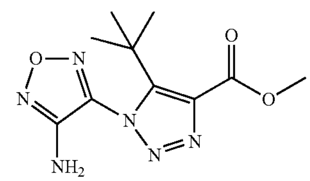 [SMILES: COC(=O)c1nnn(-c2nonc2N)c1C(C)(C)C] |
| 10 | methyl 1-(4-amino-1,2,5-oxadiazol-3-yl)-5-ethyl-1,2,3-triazole-4-carboxylate | 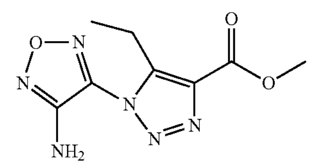 [SMILES: CCc1c(C(=O)OC)nnn1-c1nonc1N] |
| 11 | ethyl 1-(4-amino-1,2,5-oxadiazol-3-yl)-5-ethyl-1,2,3-triazole-4-carboxylate | 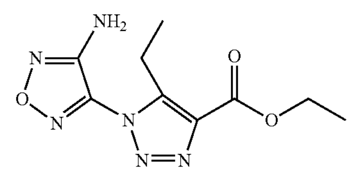 [SMILES: CCOC(=O)c1nnn(-c2nonc2N)c1CC] |
| 12 | 1-(4-amino-1,2,5-oxadiazol-3-yl)-5-propyl-1,2,3-triazole-4-carboxylic acid | 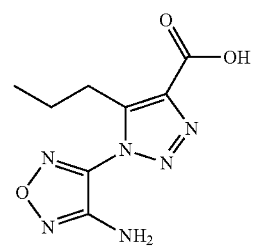 [SMILES: CCCc1c(C(=O)O)nnn1-c1nonc1N] |
| 13 | tert-butyl 1-(4-amino-1,2,5-oxadiazol-3-yl)-5-methyl-1,2,3-triazole-4-carboxylate | 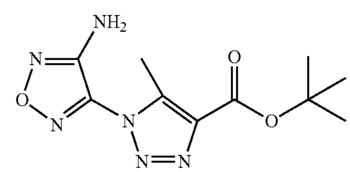 [SMILES: Cc1c(C(=O)OC(C)(C)C)nnn1-c1nonc1N] |
| 14 | isopropyl 1-(4-amino-1,2,5-oxadiazol-3-yl)-5-methyl-1,2,3-triazole-4-carboxylate | 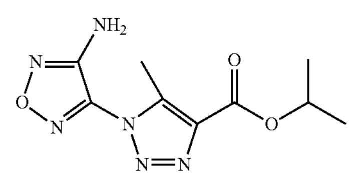 [SMILES: Cc1c(C(=O)OC(C)C)nnn1-c1nonc1N] |
| 15 | 1-(4-amino-1,2,5-oxadiazol-3-yl)-5-(methoxymethyl)-1H-1,2,3-triazole-4-carboxylic acid | 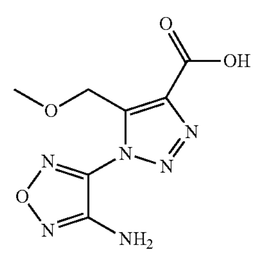 [SMILES: COCc1c(C(=O)O)nnn1-c1nonc1N] |

TABLE 1-continued

List of Compounds

| Compound # | Name | Structure |
|---|---|---|
| 16 | methyl 1-(4-amino-1,2,5-oxadiazol-3-yl)-5-(methoxymethyl)-1H-1,2,3-triazole-4-carboxylate | 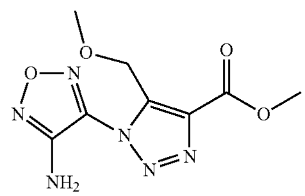 [SMILES: COCc1c(C(=O)OC)nnn1-c1nonc1N] |
| 17 | 1-(4-amino-1,2,5-oxadiazol-3-yl)-5-[(dimethylamino)methyl]-1,2,3-triazole-4-carboxylic acid | 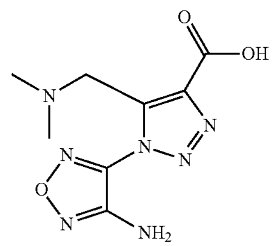 [SMILES: CN(C)Cc1c(C(=O)O)nnn1-c1nonc1N] |
| 18 | 1-(4-amino-1,2,5-oxadiazol-3-yl)-5-phenyl-1,2,3-triazole-4-carboxylic acid | 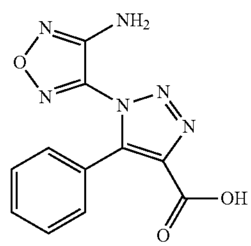 [SMILES: Nc1nonc1-n1nnc(C(=O)O)c1-c1ccccc1] |
| 19 | prop-2-en-1-yl 1-(4-amino-1,2,5-oxadiazol-yl)-5-methyl-1H-1,2,3-triazole-4-carboxylate | 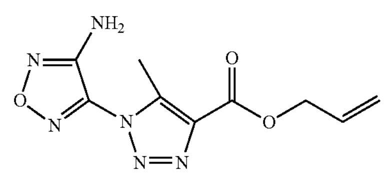 [SMILES: C=CCOC(=O)c1nnn(-c2nonc2N)c1C] |
| 20 | 2-methoxyethyl 1-(4-amino-1,2,5-oxadiazol-3-yl)-5-methyl-1,2,3-triazole-4-carboxylate | 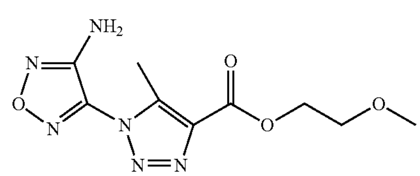 [SMILES: COCCOC(=O)c1nnn(-c2nonc2N)c1C] |
| 21 | ethyl 5-(adamantan-1-yl)-1-(4-amino-1,2,5-oxadiazol-3-yl)-1H-1,2,3-triazole-4-carboxylate | 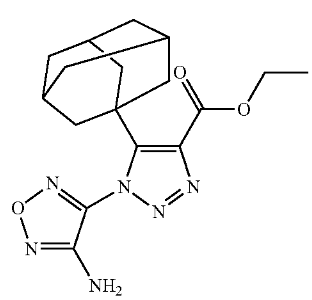 [SMILES: CCOC(=O)c1nnn(-c2nonc2N)c1C12CC3CC(CC(C3)C1)C2] |

TABLE 1-continued

List of Compounds

| Compound # | Name | Structure |
|---|---|---|
| 22 | (2R,2'S)-2,2'-(1-(4-amino-1,2,5-oxadiazol-3-yl)-1H-1,2,3-triazole-4,5-diyl)bis(butan-2-ol) | 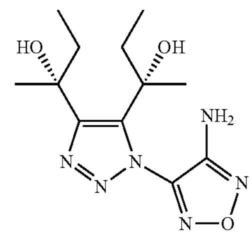 [SMILES: CC[C@](C)(O)c1c([C@](C)(O)CC)nnn1-c1nonc1N] |
| 23 | (S)-1-(1-(4-amino-1,2,5-oxadiazol-3-yl)-5-methyl-1H-1,2,3-triazol-4-yl)ethanol | 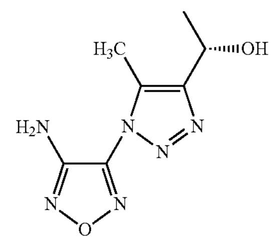 |
| 24 | 2-[1-(4-amino-1,2,5-oxadiazol-3-yl)-1H-1,2,3-triazol-5-yl]propan-2-ol | 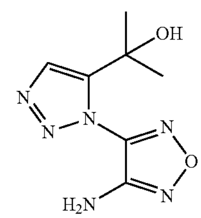 |
| 25 | [3-(4-amino-1,2,5-oxadiazol-3-yl)-5-(hydroxymethyl)-1,2,3-triazol-4-yl]methanol | 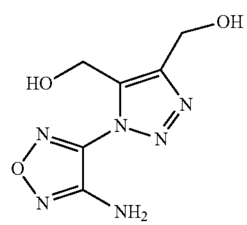 [SMILES: Nc1nonc1-n1nnc(CO)c1CO] |
| 26 | 1-[3-(4-amino-1,2,5-oxadiazol-3-yl)-1,2,3-triazol-4-yl]ethanol | 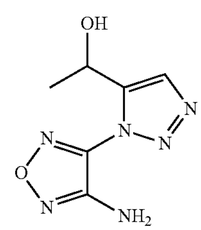 |
| 27 | 1-(4-amino-1,2,5-oxadiazol-3-yl)-5-tert-butyl-1,2,3-triazole-4-carboxylic acid | 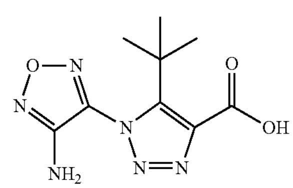 [SMILES: CC(C)(C)c1c(C(=O)O)nnn1-c1nonc1N] |
| 28 | 1-(4-amino-1,2,5-oxadiazol-3-yl)-5-(propan-2-yl)-1H-1,2,3-triazole-4-carboxylic acid | 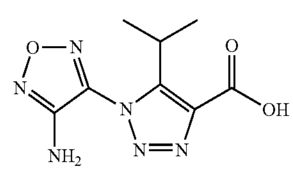 [SMILES: CC(C)c1c(C(=O)O)nnn1-c1nonc1N] |

TABLE 1-continued

List of Compounds

| Compound # | Name | Structure |
|---|---|---|
| 29 | methyl 1-(4-amino-1,2,5-oxadiazol-3-yl)-5-isopropyl-1H-1,2,3-triazole-4-carboxylate | 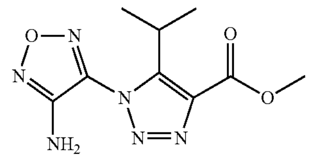 [SMILES: COC(=O)c1nnn(-c2nonc2N)c1C(C)C] |
| 30 | 1-(4-amino-1,2,5-oxadiazol-3-yl)-5-(4-methylphenyl)-1,2,3-triazole-4-carboxylic acid | 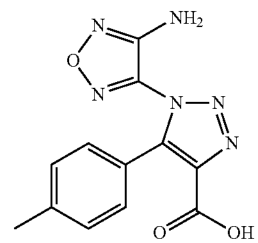 [SMILES: Cc1ccc(-c2c(C(=O)O)nnn2-c2nonc2N)cc1] |
| 31 | 3-[5-(2-thienyl)-2-furyl]propanoic acid | 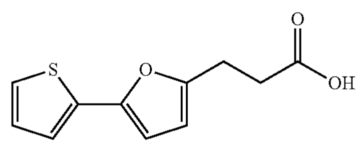 [SMILES: O=C(O)CCc1ccc(-c2cccs2)o1] |
| 32 | N-methyl-N-phenylglycine hydrochloride | 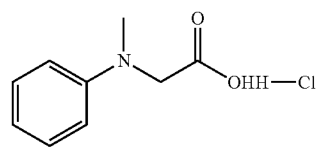 |
| 33 | 3-(5-ethyl-2-thienyl)acrylic acid | 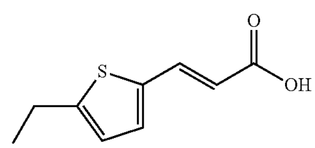 |
| 34 | 2-[(carboxymethyl)thio]-3-methyl-1,3-benzothiazol-3-ium bromide | 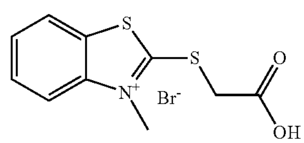 |
| 35 | 3-[5-(4-fluorophenyl)-2-furyl]acrylic acid | 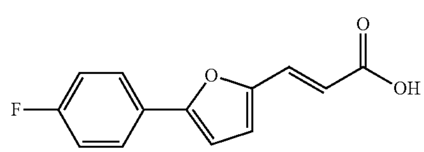 [SMILES: O=C(O)/C=C/c1ccc(-c2ccc(F)cc2)o1] |
| 36 | 3-phenyl-1,3-thiazolidine-2-carboxylic acid | 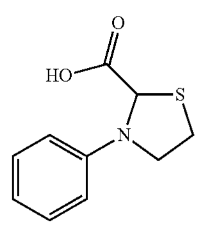 [SMILES: O=C(O)C1SCCN1c1ccccc1] |
| 37 | 3-(5-phenyl-2-furyl)propanoic acid | 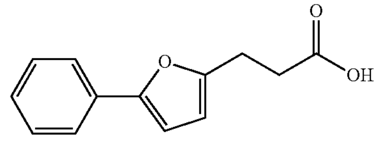 [SMILES: O=C(O)CCc1ccc(-c2ccccc2)o1] |

TABLE 1-continued

List of Compounds

| Compound # | Name | Structure |
|---|---|---|
| 38 | 3-[5-(4-fluorophenyl)-2-furyl]propanoic acid | 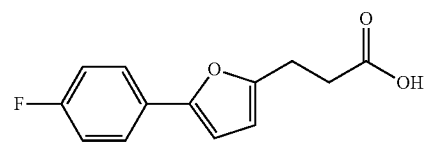 [SMILES: O=C(O)CCc1ccc(-c2ccc(F)cc2)o1] |
| 39 | (E)-3-(5-phenylfuran-2-yl)prop-2-enoic acid | 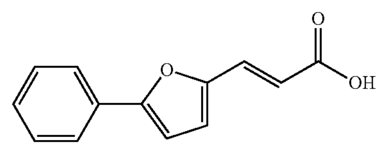 [SMILES: O=C(O)/C=C/c1ccc(-c2ccccc2)o1] |
| 40 | 3-(5-phenyl-1,3-oxazol-2-yl)propanoic acid | 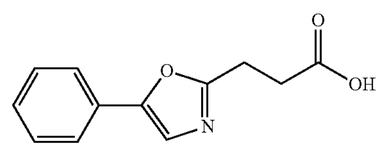 [SMILES: O=C(O)CCc1ncc(-c2ccccc2)o1] |
| 41 | 3-[5-(4-chlorophenyl)-1,3-oxazol-2-yl]propanoic acid | 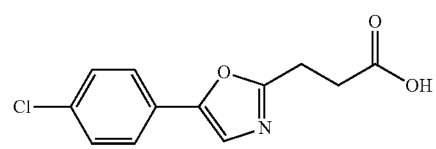 [SMILES: O=C(O)CCc1ncc(-c2ccc(Cl)cc2)o1] |
| 42 | 3-(5-phenyl-1,3,4-oxadiazol-2-yl)propanoic acid | 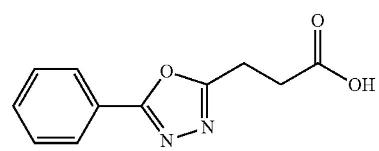 [SMILES: O=C(O)CCc1nnc(-c2ccccc2)o1] |
| 43 | 2-[(4-phenyl-1,3-thiazol-2-yl)sulfanyl]acetic acid | 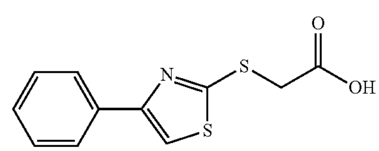 [SMILES: O=C(O)CSc1nc(-c2ccccc2)cs1] |
| 44 | 3-[5-(4-bromophenyl)-1,3-oxazol-2-yl]propanoic acid | 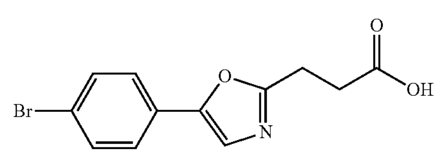 [SMILES: O=C(O)CCc1ncc(-c2ccc(Br)cc2)o1] |
| 45 | 3-(5-thiophen-2-yl-1H-pyrrol-2-yl)propanoic acid | 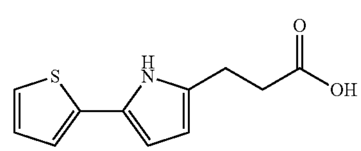 |
| 46 | 3-(5-phenyl-3,4-dihydropyrazol-2-yl)propanoic acid | 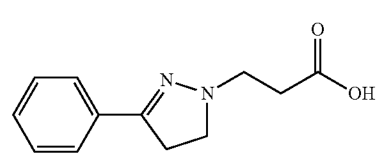 [SMILES: O=C(O)CCN1CCC(c2ccccc2)=N1] |
| 47 | (E)-3-[5-(2-chlorophenyl)furan-2-yl]prop-2-enoic acid | 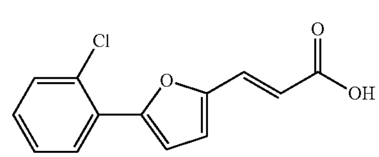 [SMILES: O=C(O)/C=C/c1ccc(-c2ccccc2Cl)o1] |

TABLE 1-continued

List of Compounds

| Compound # | Name | Structure |
|---|---|---|
| 48 | 2-[(E)-2-nitroethenyl]-5-phenylfuran | 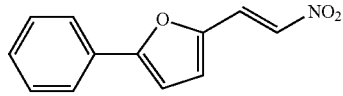 [SMILES: O=[N+]([O-])/C=C/c1ccc(-c2ccccc2)o1] |
| 49 | 3-(6-oxo-3-phenylpyridazin-1-yl)propanoic acid | 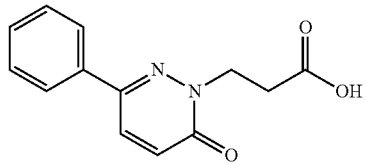 [SMILES: O=C(O)CCn1nc(-c2ccccc2)ccc1=O] |
| 50 | 3-(3-phenyl-1,2,4-oxadiazol-5-yl)propanoic acid | 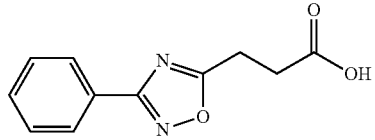 [SMILES: O=C(O)CCc1nc(-c2ccccc2)no1] |
| 51 | 2-quinolin-2-ylsulfanylacetate | 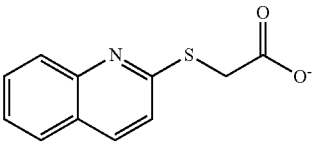 [SMILES: O=C([O-])CSc1ccc2ccccc2n1] |
| 52 | 2-[(5-phenyl-1,3,4-oxadiazol-2-yl)sulfanyl]acetic acid | 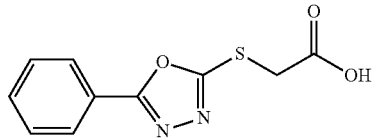 |
| 53 | 3-(5-phenyl-1H-pyrrol-2-yl)propanoic acid | 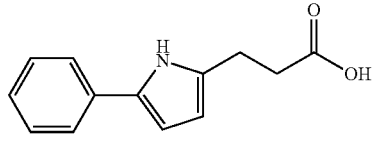 [SMILES: O=C(O)CCc1ccc(-c2ccccc2)[nH]1] |
| 54 | 3-[3-(4-chlorophenyl)-6-oxopyridazin-1-yl]propanoic acid | 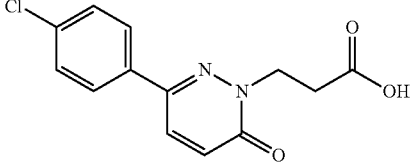 [SMILES: O=C(O)CCn1nc(-c2ccc(Cl)cc2)ccc1=O] |
| 55 | 3-[3-(4-fluorophenyl)-6-oxopyridazin-1-yl]propanoic acid | 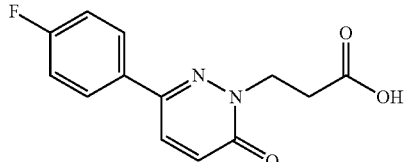 |
| 56 | 2-[3-(tetrazol-1-yl)phenoxy]acetic acid | 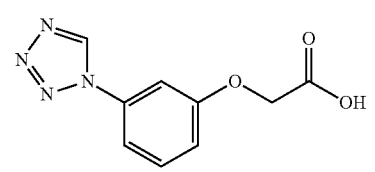 [SMILES: O=C(O)COc1cccc(-n2cnnn2)c1] |

TABLE 1-continued

List of Compounds

| Compound # | Name | Structure |
|---|---|---|
| 57 | (E)-3-[5-(2-bromophenyl)furan-2-yl]prop-2-enoic acid | 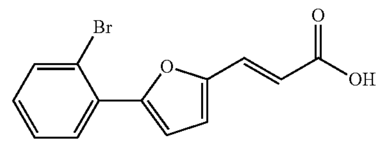 |
| 58 | 4-phenyl-methoxybutanoic acid | 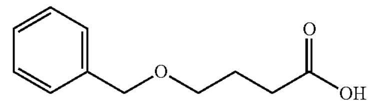 [SMILES: O=C(O)CCCOCc1ccccc1] |
| 59 | 3-[3-(4-methylphenyl)-6-oxopyridazin-1-yl]propanoic acid | 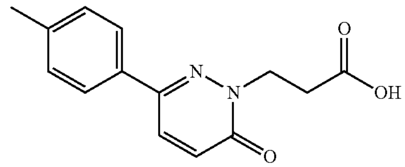 [SMILES: Cc1ccc(-c2ccc(=O)n(CCC(=O)O)n2)cc1] |
| 60 | 3-[3-(2-fluorophenyl)-1,2,4-oxadiazol-5-yl]propanoic acid | 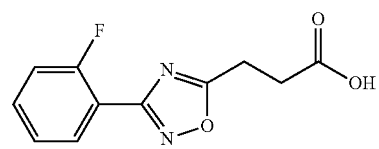 [SMILES: O=C(O)CCc1nc(-c2ccccc2F)no1] |
| 61 | 6-nitro-2-phenylindazole | 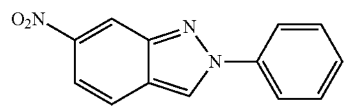 [SMILES: O=[N+]([O-])c1ccc2cn(-c3ccccc3)nc2c1] |
| 62 | 2-[1-(2,2,2-trifluoroethyl)pyrazol-3-yl]acetic acid | 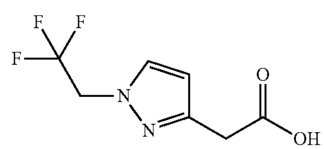 [SMILES: O=C(O)Cc1ccn(CC(F)(F)F)n1] |
| 63 | 3-(5-thiophen-2-ylfuran-2-yl)propanoate | 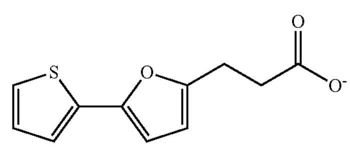 [SMILES: O=C([O-])CCc1ccc(-c2cccs2)o1] |
| 64 | 3-(5-thiophen-2-ylfuran-2-yl)prop-2-enoic acid | (E)- or (Z)- isomer |
| 65 | methyl 3-(5-thiophen-2-ylfuran-2-yl)propanoate | 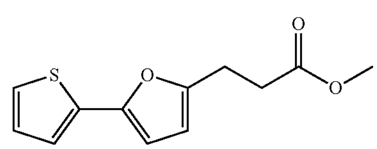 [SMILES: COC(=O)CCc1ccc(-c2cccs2)o1] |
| 66 | (E)-3-(5-thiophen-2-ylfuran-2-yl)prop-2-enoic acid | 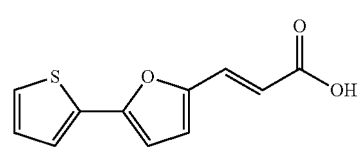 [SMILES: O=C(O)/C=C/c1ccc(-c2cccs2)o1] |

TABLE 1-continued

List of Compounds

| Compound # | Name | Structure |
|---|---|---|
| 67 | 5-(5-methylfuran-2-yl)thiophene-2-carboxylic acid | 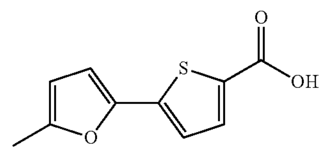 |
| 68 | 2-(5-thiophen-2-ylfuran-2-yl)acetic acid | 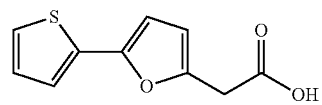 [SMILES: O=C(O)Cc1ccc(-c2cccs2)o1] |
| 69 | methyl 3-(5-thiophen-2-ylfuran-2-yl)prop-2-enoate | 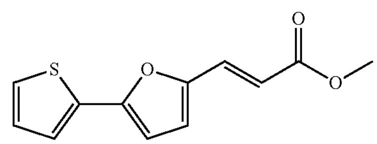 [SMILES: COC(=O)/C=C/c1ccc(-c2cccs2)o1] |
| 70 | thiophen-2-ylmethyl 3-(furan-2-yl)propanoate | 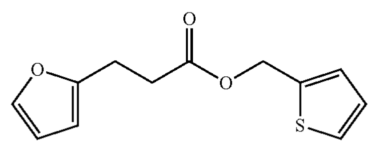 [SMILES: O=C(CCc1ccco1)OCc1cccs1] |
| 71 | | 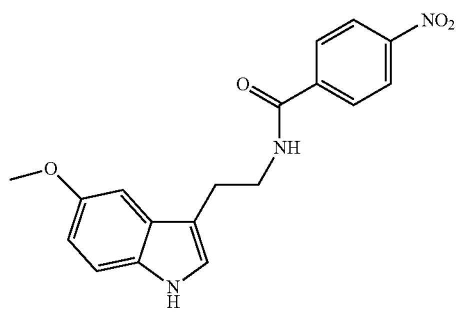 [SMILES: COc1ccc2[nH]cc(CCNC(=O)c3ccc([N+](=O)[O-])cc3)c2c1] |
| 72 | | 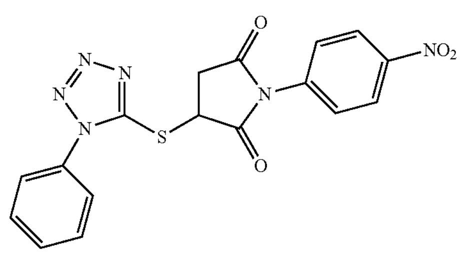 [SMILES: O=C1CC(Sc2nnnn2-c2ccccc2)C(=O)N1c1ccc([N+](=O)[O-])cc1] |
| 73 | | 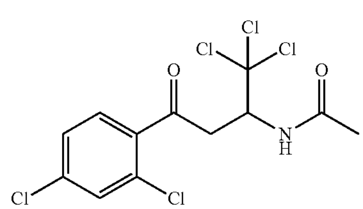 [SMILES: CC(=O)NC(CC(=O)c1ccc(Cl)cc1Cl)C(Cl)(Cl)Cl] |
| 74 | | 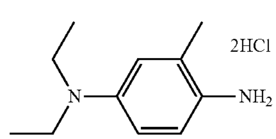 |

TABLE 1-continued

List of Compounds

| Compound # | Name | Structure |
|---|---|---|
| 75 | | (structure) |
| 76 | | (structure) |
| 77 | | (structure) |
| 78 | | (structure) |
| 79 | | (structure) |
| 80 | | (structure) |

TABLE 1-continued
List of Compounds
| Compound # | Name | Structure |
|---|---|---|
| 81 | | 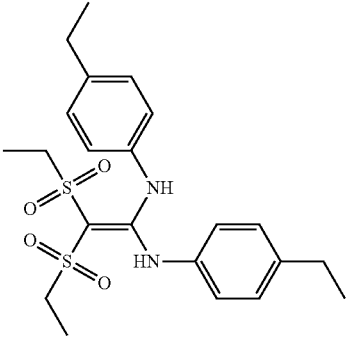 [SMILES: CCc1ccc(NC(Nc2ccc(CC)cc2)=C(S(=O)(=O)CC)S(=O)(=O)CC)cc1] |
| 82 | | 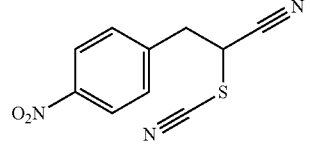 [SMILES: N#CSC(C#N)Cc1ccc([N+](=O)[O-])cc1] |
| 83 | | 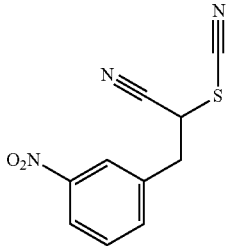 [SMILES: N#CSC(C#N)Cc1cccc([N+](=O)[O-])c1] |
| 84 | | 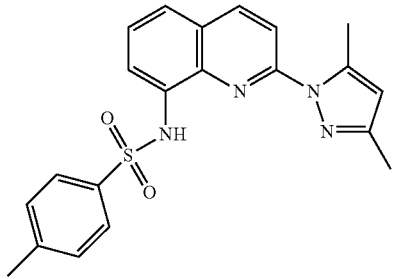 |
| 85 | | 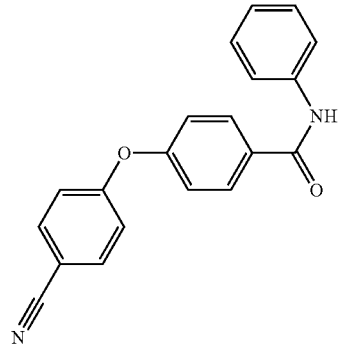 [SMILES: N#Cc1ccc(Oc2ccc(C(=O)Nc3ccccc3)cc2)cc1] |

TABLE 1-continued

List of Compounds

| Compound # | Name | Structure |
|---|---|---|
| 86 | | 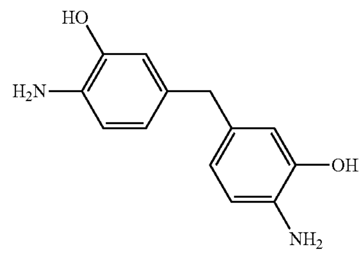 [SMILES: Nc1ccc(Cc2ccc(N)c(O)c2)cc1O] |
| 87 | | 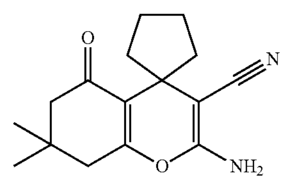 [SMILES: CC1(C)CC(=O)C2=C(C1)OC(N)=C(C#N)C21CCCC1] |
| 88 | | 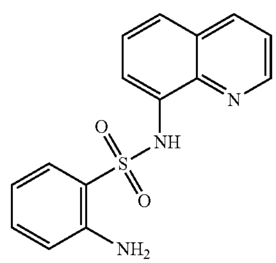 [SMILES: Nc1ccccc1S(=O)(=O)Nc1cccc2cccnc12] |
| 89 | | 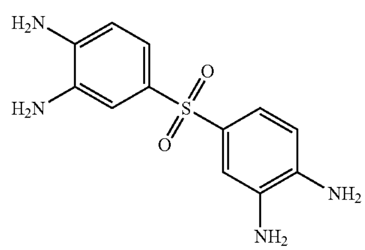 [SMILES: Nc1ccc(S(=O)(=O)c2ccc(N)c(N)c2)cc1N] |
| 90 | | 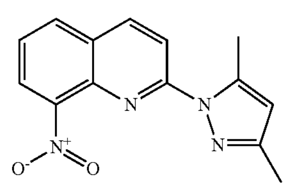 [SMILES: Cc1cc(C)n(-c2ccc3cccc([N+](=O)[O-])c3n2)n1] |
| 91 | | 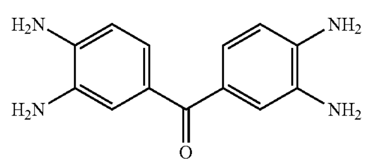 [SMILES: Nc1ccc(C(=O)c2ccc(N)c(N)c2)cc1N] |
| 92 | | 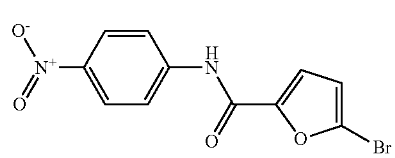 [SMILES: O=C(Nc1ccc([N+](=O)[O-])cc1)c1ccc(Br)o1] |

TABLE 1-continued

List of Compounds

| Compound # | Name | Structure |
|---|---|---|
| 93 | | 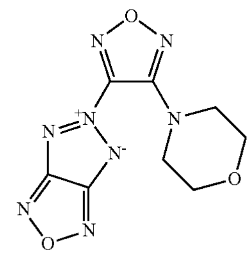 [SMILES: C1CN(c2nonc2-[n+]2nc3nonc3[n-]2)CCO1] |
| 94 | | 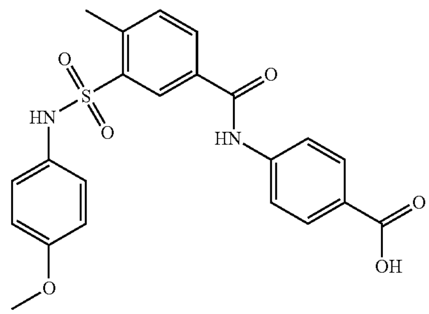 [SMILES: COc1ccc(NS(=O)(=O)c2cc(C(=O)Nc3ccc(C(=O)O)cc3)ccc2C)cc1] |
| 95 | | 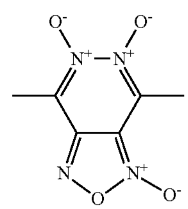 |
| 96 | | 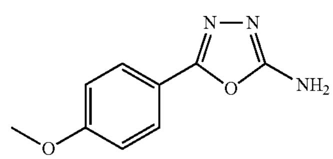 |
| 97 | | 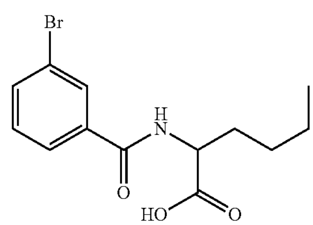 [SMILES: CCCCC(NC(=O)c1cccc(Br)c1)C(=O)O] |
| 98 | | 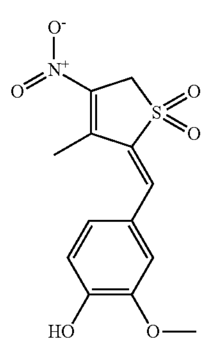 [SMILES: COc1cc(/C=C2\C(C)=C([N+](=O)[O-])CS2(=O)=O)ccc1O] |

TABLE 1-continued

List of Compounds

| Compound # | Name | Structure |
|---|---|---|
| 99 | | 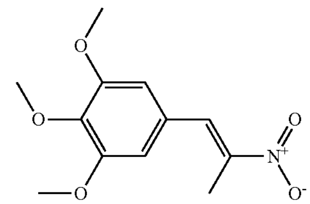 [SMILES: COc1cc(/C=C(\C)[N+](=O)[O-])cc(OC)c1OC] |
| 100 | | 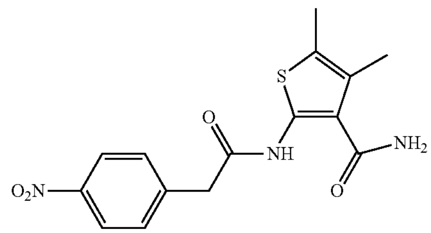 [SMILES: Cc1sc(NC(=O)Cc2ccc([N+](=O)[O-])cc2)c(C(N)=O)c1C] |
| 101 | | 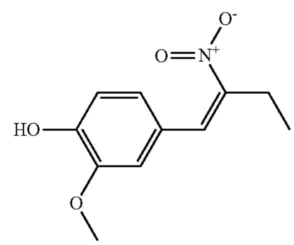 [SMILES: CC/C(=C/c1ccc(O)c(OC)c1)[N+](=O)[O-]] |
| 102 | | 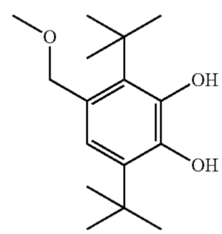 [SMILES: COCc1cc(C(C)(C)C)c(O)c(O)c1C(C)(C)C] |
| 103 | | 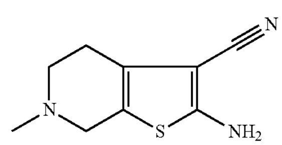 |
| 104 | | 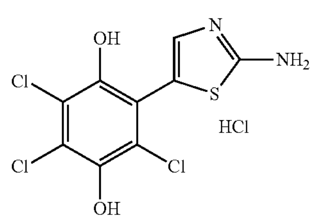 [SMILES: Nc1ncc(-c2c(O)c(Cl)c(Cl)c(O)c2Cl)s1 ; Cl] |
| 105 | | 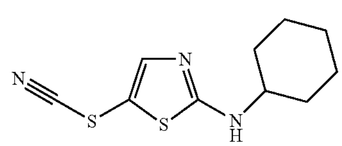 [SMILES: N#CSc1cnc(NC2CCCCC2)s1] |

TABLE 1-continued

List of Compounds

| Compound # | Name | Structure |
|---|---|---|
| 106 | | 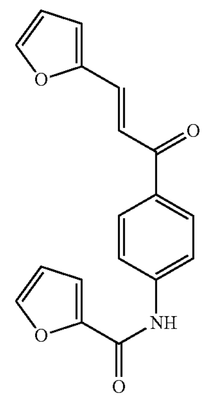 [SMILES: O=C(/C=C/c1ccco1)c1ccc(NC(=O)c2ccco2)cc1] |
| 107 | | 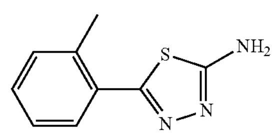 |
| 108 | | 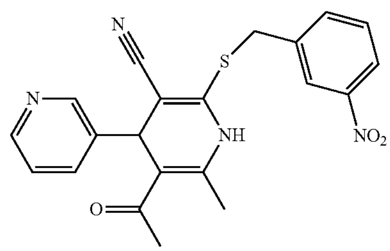 [SMILES: CC(=O)C1=C(C)NC(SCc2cccc([N+](=O)[O-])c2)=C(C#N)C1c1cccnc1] |
| 109 | | 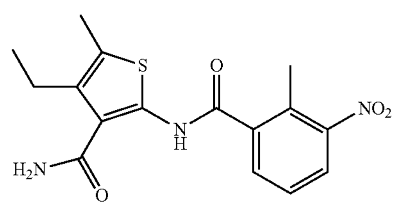 [SMILES: CCc1c(C)sc(NC(=O)c2cccc([N+](=O)[O-])c2C)c1C(N)=O] |
| 110 | | 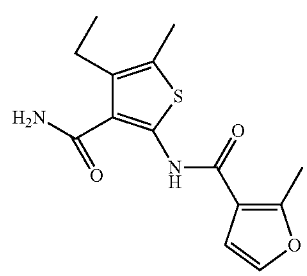 [SMILES: CCc1c(C)sc(NC(=O)c2ccoc2C)c1C(N)=O] |
| 111 | | 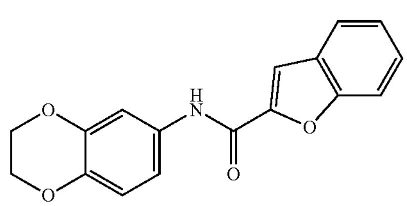 [SMILES: O=C(Nc1ccc2c(c1)OCCO2)c1cc2ccccc2o1] |

TABLE 1-continued

| Compound # | Name | Structure |
|---|---|---|
| 112 | | 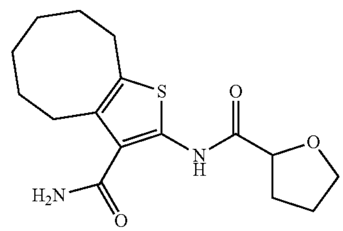 [SMILES: NC(=O)c1c(NC(=O)C2CCCO2)sc2c1CCCCCC2] |
| 113 | | 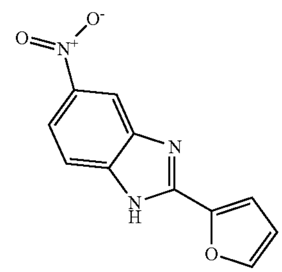 [SMILES: O=[N+]([O-])c1ccc2[nH]c(-c3ccco3)nc2c1] |
| 114 | | 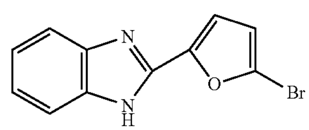 [SMILES: Brc1ccc(-c2nc3ccccc3[nH]2)o1] |
| 115 | | 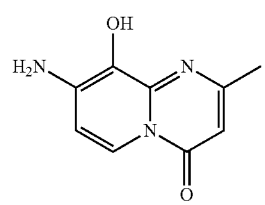 |
| 116 | | 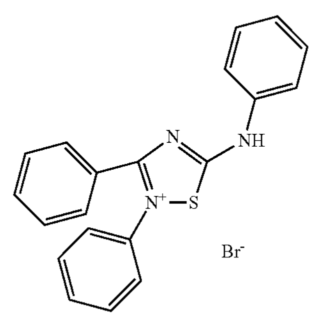 [SMILES: c1ccc(Nc2nc(-c3ccccc3)[n+](-c3ccccc3)s2)cc1 ; [Br-]] |
| 117 | | 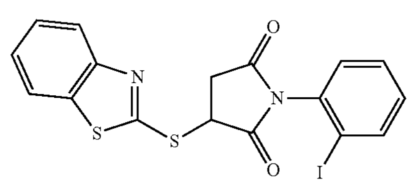 [SMILES: O=C1CC(Sc2nc3ccccc3s2)C(=O)N1c1ccccc1I] |

TABLE 1-continued

List of Compounds

| Compound # | Name | Structure |
|---|---|---|
| 118 | | 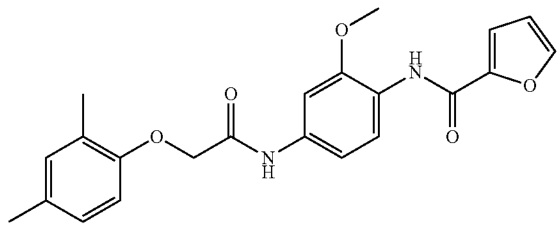 [SMILES: COc1cc(NC(=O)COc2ccc(C)cc2C)ccc1NC(=O)c1ccco1] |
| 119 | | 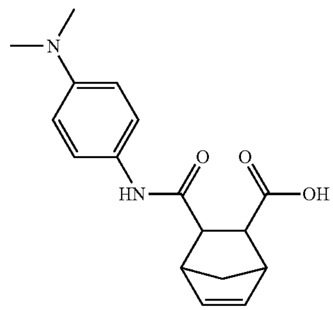 [SMILES: CN(C)c1ccc(NC(=O)C2C3C=CC(C3)C2C(=O)O)cc1] |
| 120 | | 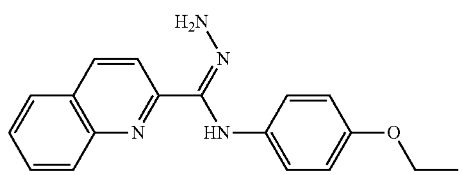 [SMILES: CCOc1ccc(N/C(=N/N)c2ccc3ccccc3n2)cc1] |
| 121 | | 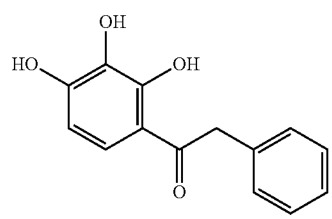 [SMILES: O=C(Cc1ccccc1)c1ccc(O)c(O)c1O] |
| 122 | | 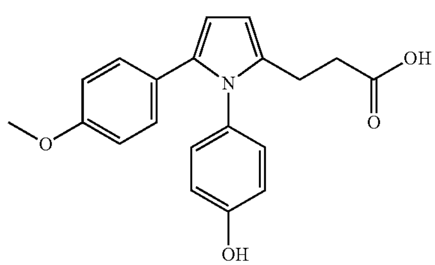 [SMILES: COc1ccc(-c2ccc(CCC(=O)O)n2-c2ccc(O)cc2)cc1] |
| 123 | | 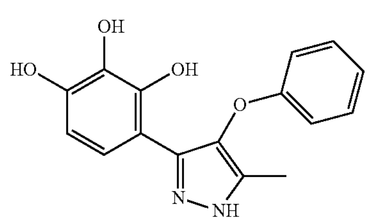 [SMILES: Cc1[nH]nc(-c2ccc(O)c(O)c2O)c1Oc1ccccc1] |

TABLE 1-continued
List of Compounds
| Compound # | Name | Structure |
|---|---|---|
| 124 | | 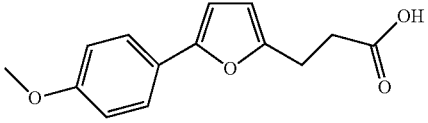 [SMILES: COc1ccc(-c2ccc(CCC(=O)O)o2)cc1] |
| 125 | | 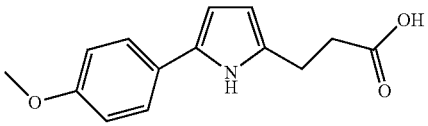 [SMILES: COc1ccc(-c2ccc(CCC(=O)O)[nH]2)cc1] |
| 126 | | 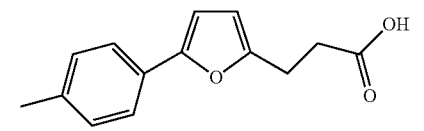 [SMILES: Cc1ccc(-c2ccc(CCC(=O)O)o2)cc1] |
| 127 | | 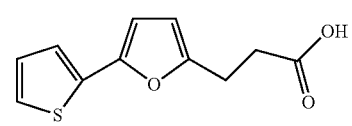 [SMILES: O=C(O)CCc1ccc(-c2cccs2)o1] |
| 128 | | 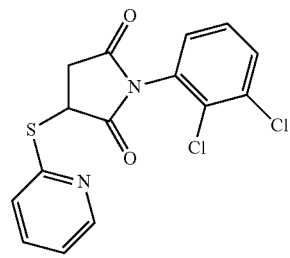 [SMILES: O=C1CC(Sc2ccccn2)C(=O)N1c1cccc(Cl)c1Cl] |
| 129 | | 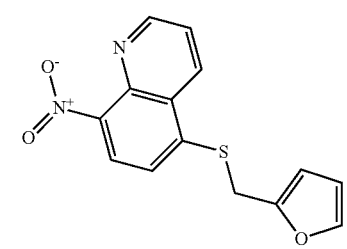 [SMILES: O=[N+]([O-])c1ccc(SCc2ccco2)c2cccnc12] |
| 130 | | 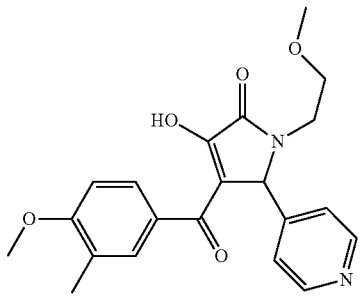 [SMILES: COCCN1C(=O)C(O)=C(C(=O)c2ccc(OC)c(C)c2)C1c1ccncc1] |

TABLE 1-continued

| Compound # | Name | Structure |
|---|---|---|
| 131 | | 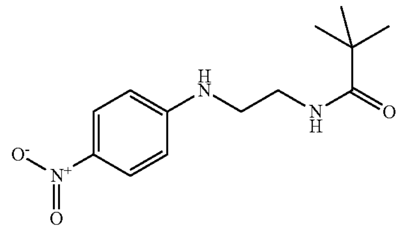 [SMILES: CC(C)(C)C(=O)NCCNc1ccc([N+](=O)[O-])cc1] |
| 132 | | 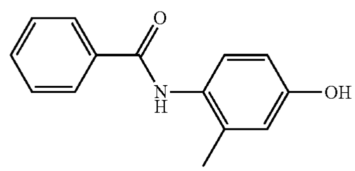 [SMILES: Cc1cc(O)ccc1NC(=O)c1ccccc1] |
| 133 | | 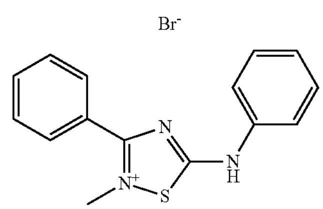 [SMILES: [Br-] ; C[n+]1sc(Nc2ccccc2)nc1-c1ccccc1] |
| 134 | | 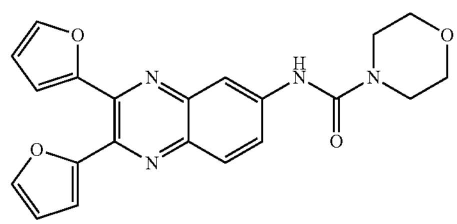 [SMILES: O=C(Nc1ccc2nc(-c3ccco3)c(-c3ccco3)nc2c1)N1CCOCC1] |
| 135 | | 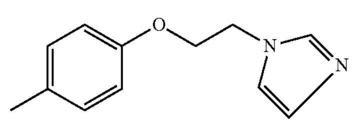 |
| 136 | | 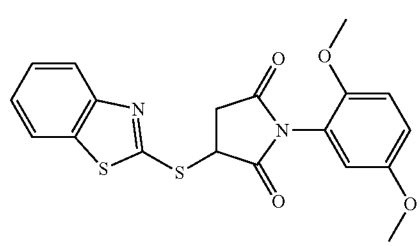 [SMILES: COc1ccc(OC)c(N2C(=O)CC(Sc3nc4ccccc4s3)C2=O)c1] |
| 137 | | 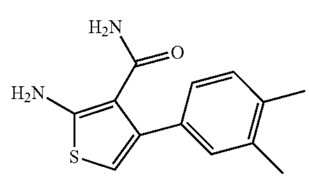 [SMILES: Cc1ccc(-c2csc(N)c2C(N)=O)cc1C] |

TABLE 1-continued

List of Compounds

| Compound # | Name | Structure |
|---|---|---|
| 138 | | 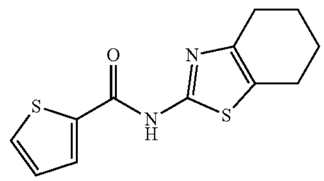 [SMILES: O=C(Nc1nc2c(s1)CCCC2)c1cccs1] |
| 139 | | 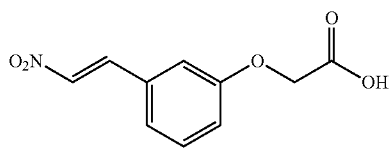 [SMILES: O=C(O)COc1cccc(/C=C/[N+](=O)[O-])c1] |
| 140 | | 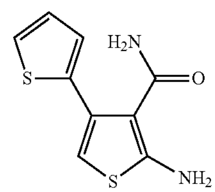 [SMILES: NC(=O)c1c(-c2cccs2)csc1N] |
| 141 | | 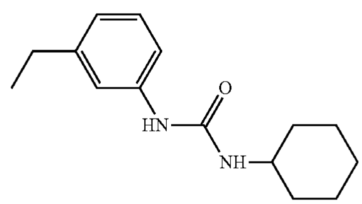 [SMILES: CCc1cccc(NC(=O)NC2CCCCC2)c1] |
| 142 | | 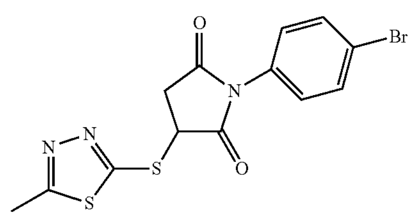 [SMILES: Cc1nnc(SC2CC(=O)N(c3ccc(Br)cc3)C2=O)s1] |
| 143 | | 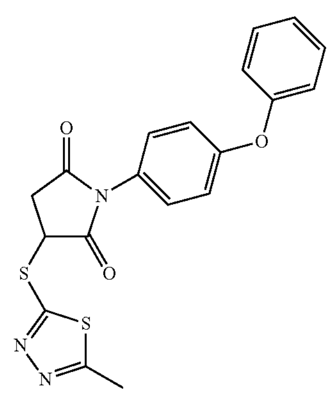 [SMILES: Cc1nnc(SC2CC(=O)N(c3ccc(Oc4ccccc4)cc3)C2=O)s1] |

TABLE 1-continued

List of Compounds

| Compound # | Name | Structure |
|---|---|---|
| 144 | | 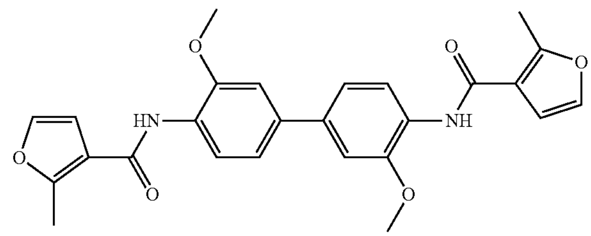 [SMILES: COc1cc(-c2ccc(NC(=O)c3ccoc3C)c(OC)c2)ccc1NC(=O)c1ccoc1C] |
| 145 | | 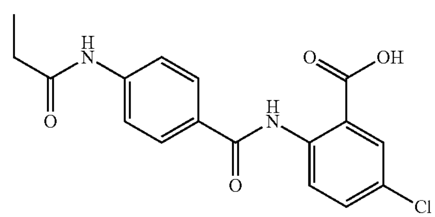 [SMILES: CCC(=O)Nc1ccc(C(=O)Nc2ccc(Cl)cc2C(=O)O)cc1] |
| 146 | | 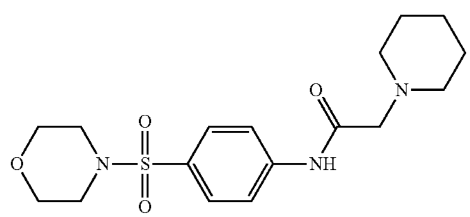 [SMILES: O=C(CN1CCCCC1)Nc1ccc(S(=O)(=O)N2CCOCC2)cc1] |
| 147 | | 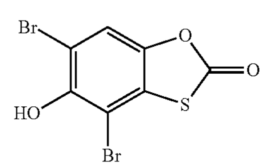 [SMILES: O=c1oc2cc(Br)c(O)c(Br)c2s1] |
| 148 | | 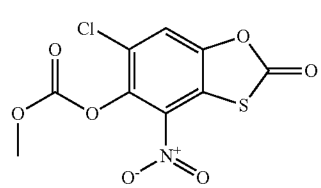 [SMILES: COC(=O)Oc1c(Cl)cc2oc(=O)sc2c1[N+](=O)[O-]] |

TABLE 1-continued
List of Compounds
| Compound # | Name | Structure |
|---|---|---|
| 149 | | 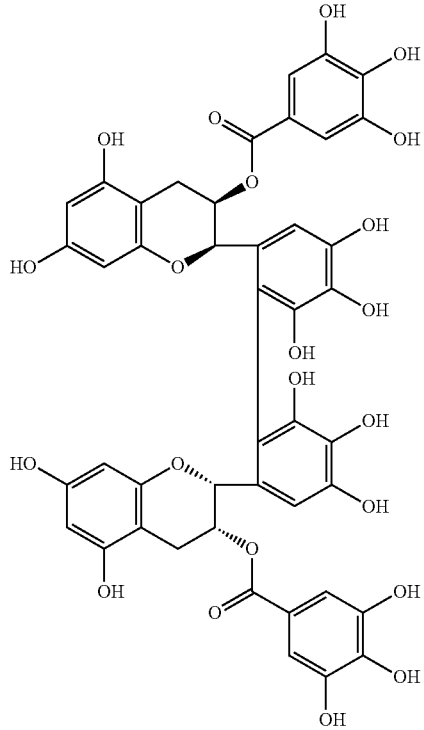 [SMILES: O=C(O[C@@H]1Cc2c(O)cc(O)cc2O[C@@H]1c1cc(O)c(O)c(O)c1-c1c([C@H]2Oc3cc(O)cc(O)c3C[C@H]2OC(=O)c2cc(O)c(O)c(O)c2)cc(O)c(O)c1O)c1cc(O)c(O)c(O)c1] |
| 150 | | 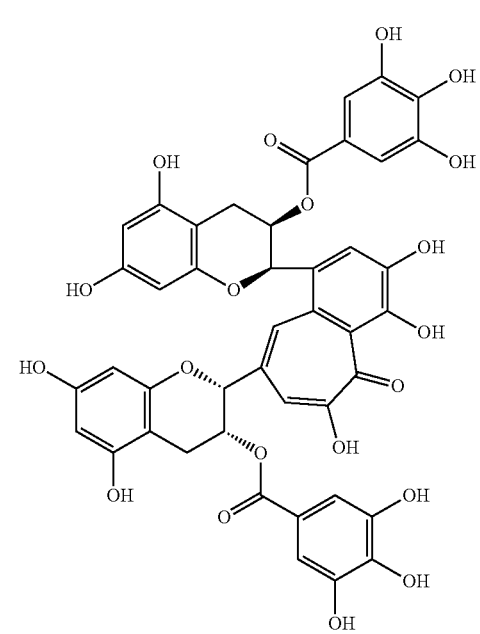 [SMILES: O=C(O[C@@H]1Cc2c(O)cc(O)cc2O[C@@H]1c1cc(O)c(=O)c2c(O)c(O)cc([C@H]3Oc4cc(O)cc(O)c4C[C@H]3OC(=O)c3cc(O)c(O)c(O)c3)c2c1)c1cc(O)c(O)c(O)c1] |

TABLE 1-continued
List of Compounds
| Compound # | Name | Structure |
|---|---|---|
| 151 | | 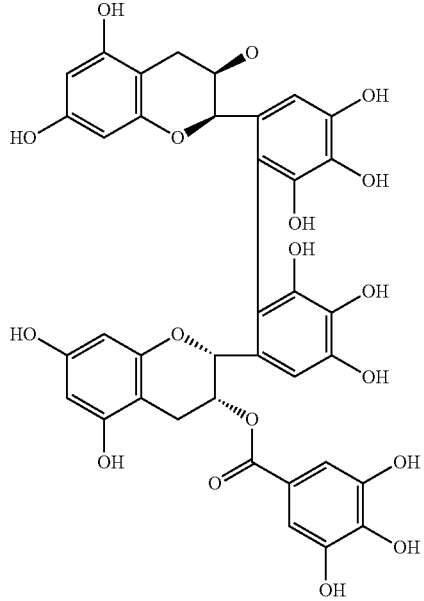 [SMILES: O=C(O[C@@H]1Cc2c(O)cc(O)cc2O[C@@H]1c1cc(O)c(O)c(O)c1-c1c([C@H]2Oc3cc(O)cc(O)c3C[C@H]2O)cc(O)c(O)c1O)c1cc(O)c(O)c(O)c1] |
| 152 | | 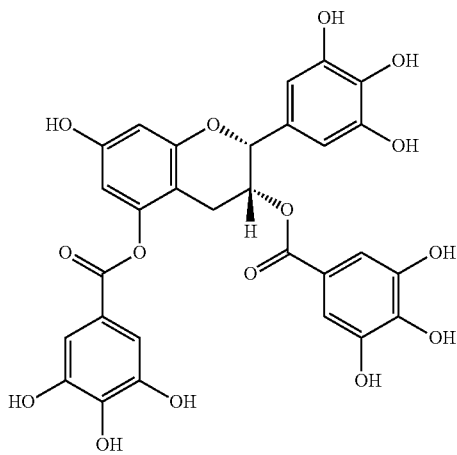 [SMILES: O=C(Oc1cc(O)cc2c1C[C@@H](OC(=O)c1cc(O)c(O)c(O)c1)[C@@H](c1cc(O)c(O)c(O)c1)O2)c1cc(O)c(O)c(O)c1] |
| 153 | | 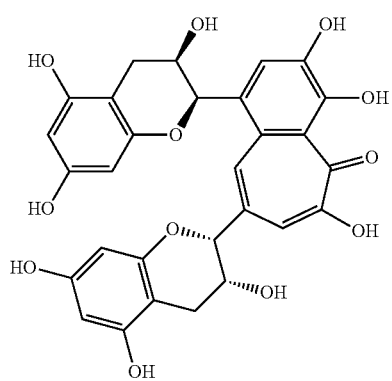 [SMILES: O=c1c(O)cc([C@H]2Oc3cc(O)cc(O)c3C[C@H]2O)cc2c([C@H]3Oc4cc(O)cc(O)c4C[C@H]3O)cc(O)c(O)c12] |

TABLE 1-continued

List of Compounds

| Compound # | Name | Structure |
|---|---|---|
| 154 | | 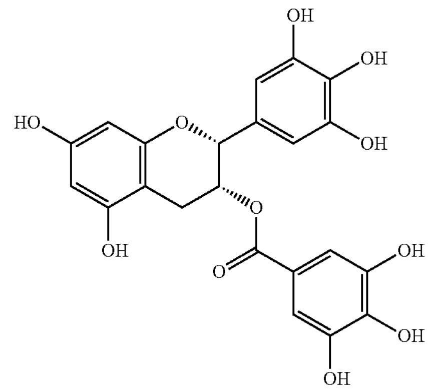 [SMILES: O=C(O[C@@H]1Cc2c(O)cc(O)cc2O[C@@H]1c1cc(O)c(O)c(O)c1)c1cc(O)c(O)c(O)c1] |
| 155 | | 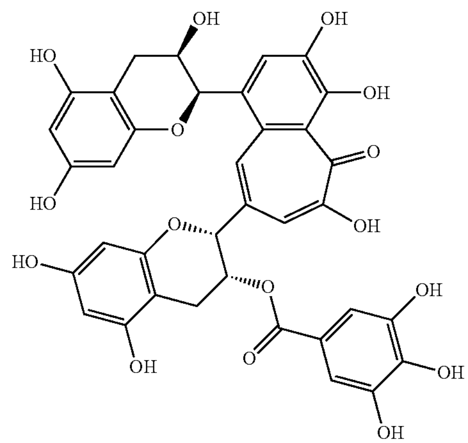 [SMILES: O=C(O[C@@H]1Cc2c(O)cc(O)cc2O[C@@H]1c1cc(O)c(=O)c2c(O)c(O)cc([C@H]3Oc4cc(O)cc(O)c4C[C@H]3O)c2c1)c1cc(O)c(O)c(O)c1] |
| 156 | | 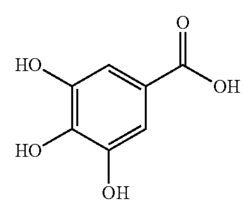 [SMILES: O=C(O)c1cc(O)c(O)c(O)c1] |
| 157 | | 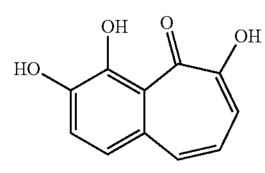 [SMILES: O=c1c(O)cccc2ccc(O)c(O)c12] |
| 158 | | 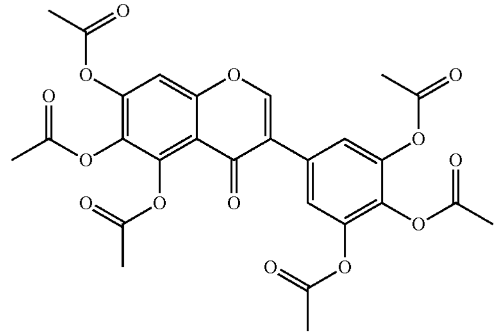 [SMILES: CC(=O)Oc1cc(-c2coc3cc(OC(C)=O)c(OC(C)=O)c(OC(C)=O)c3c2=O)cc(OC(C)=O)c1OC(C)=O] |

TABLE 1-continued

| Compound # | Name | Structure |
|---|---|---|
| 159 | | 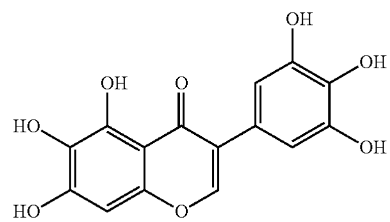 [SMILES: O=c1c(-c2cc(O)c(O)c(O)c2)coc2cc(O)c(O)c(O)c12] |
| 160 | | 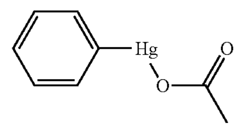 |
| 161 | | 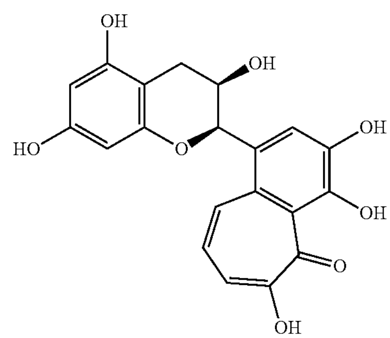 [SMILES: O=c1c(O)cccc2c([C@H]3Oc4cc(O)cc(O)c4C[C@H]3O)cc(O)c(O)c12] |
| 162 | | 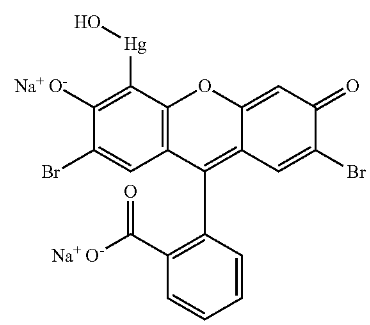 |
| 163 | | 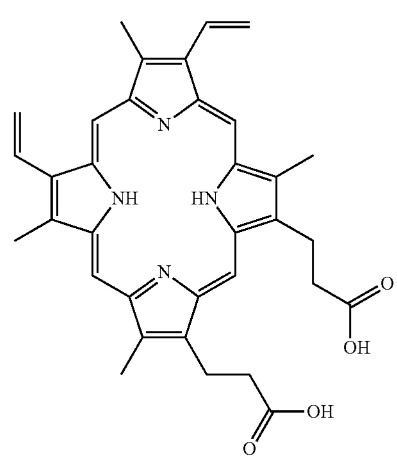 [SMILES: C=CC1=C(C)c2cc3[nH]c(cc4nc(cc5[nH]c(cc1n2)c(C)c5CCC(=O)O)C(CCC(=O)O)=C4C)c(C)c3C=C] |

TABLE 1-continued
List of Compounds
| Compound # | Name | Structure |
|---|---|---|
| 164 | | 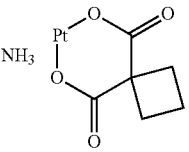 |
| 165 | | 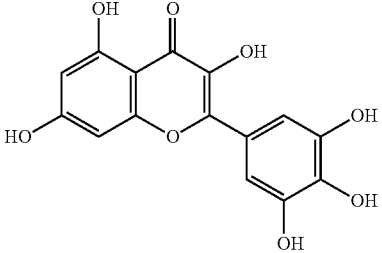 [SMILES: O=c1c(O)c(-c2cc(O)c(O)c(O)c2)oc2cc(O)cc(O)c12] |
| 166 | | 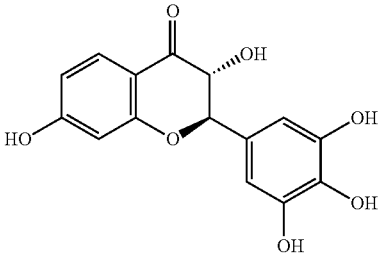 |
| 167 | | 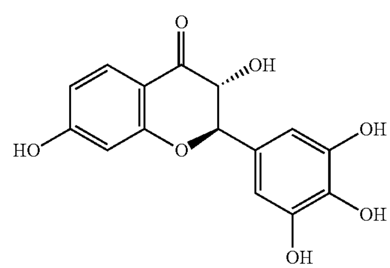 [SMILES: O=C1c2ccc(O)cc2O[C@H](c2cc(O)c(O)c(O)c2)[C@H]1O] |
| 168 | | 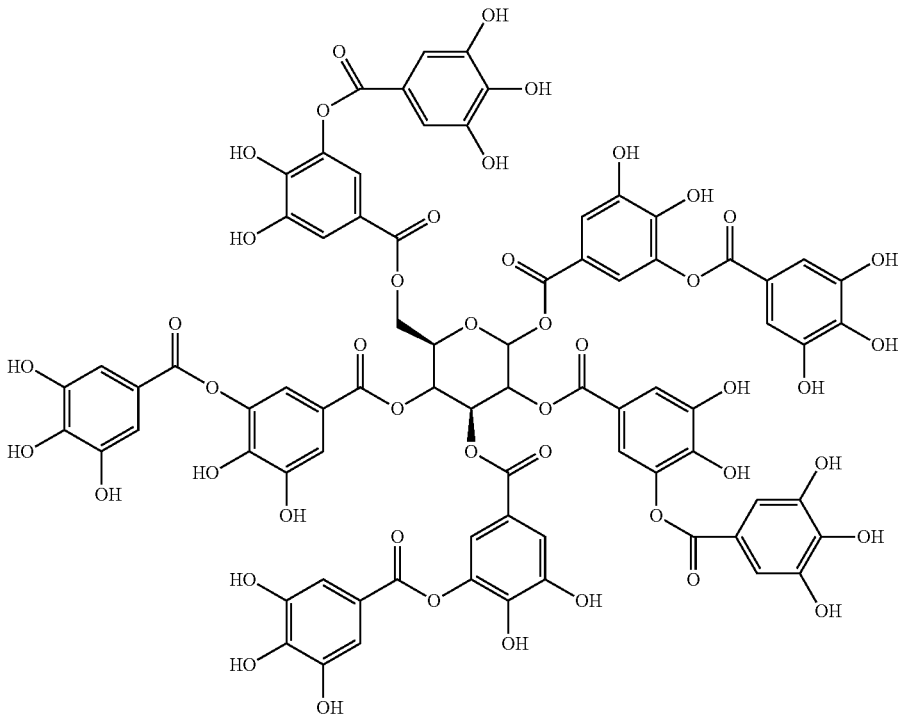 [SMILES: O=C(OC[C@H]1OC(OC(=O)c2cc(O)c(O)c(OC(=O)c3cc(O)c(O)c(O)c3)c2)C(OC(=O)c2cc(O)c(O)c(OC(=O)c3cc(O)c(O)c(O)c3)c2)[C@@H](OC(=O)c2cc(O)c(O)c(OC(=O)c3cc(O)c(O)c(O)c3)c2)C1OC(=O)c1cc(O)c(O)c(OC(=O)c2cc(O)c(O)c(O)c2)c1)c1cc(O)c(O)c(OC(=O)c2cc(O)c(O)c(O)c2)c1] |

TABLE 1-continued

List of Compounds

| Compound # | Name | Structure |
|---|---|---|
| 169 | | 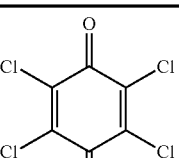 |
| 170 | | 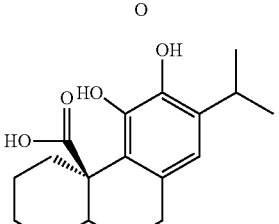 |

The present application further provides a pharmaceutical composition comprising a compound provided herein (e.g., a compound provided in Table 1), or a pharmaceutically acceptable salt thereof, and at least one pharmaceutically acceptable carrier. In some embodiments, the pharmaceutical composition comprises 2,2'-[1-(4-amino-1,2,5-oxadiazol-3-yl)-1H-1,2,3-triazole-4,5-diyl]di(2-butanol) (1), or a pharmaceutically acceptable salt thereof, and at least one pharmaceutically acceptable carrier. In some embodiments, the pharmaceutical composition comprises 3-[5-(2-thienyl)-2-furyl]propanoic acid (31), or a pharmaceutically acceptable salt thereof, and at least one pharmaceutically acceptable carrier.

When employed as pharmaceuticals, the compounds provided herein can be administered in the form of pharmaceutical compositions; thus, the methods described herein can include administering pharmaceutical compositions provided herein.

These compositions can be prepared as described herein or elsewhere, and can be administered by a variety of routes, depending upon whether local or systemic treatment is desired and upon the area to be treated. Administration may be pulmonary (e.g., by inhalation or insufflation of powders or aerosols, including by nebulizer; intratracheal or intranasal), oral, or parenteral. Parenteral administration may include, but is not limited to intravenous, intraarterial, subcutaneous, intraperitoneal, intramuscular injection or infusion; or intracranial, (e.g., intrathecal, intraocular, or intraventricular) administration. Parenteral administration can be in the form of a single bolus dose, or may be, for example, by a continuous perfusion pump. Conventional pharmaceutical carriers, aqueous, powder or oily bases, thickeners and the like may be necessary or desirable.

In making the compositions provided herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments, soft and hard gelatin capsules, suppositories, sterile injectable solutions, and sterile packaged powders.

Some examples of suitable excipients include, without limitation, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include, without limitation, lubricating agents such as talc, magnesium stearate, and mineral oil; wetting agents; emulsifying and suspending agents; preserving agents such as methyl- and propylhydroxy-benzoates; sweetening agents; flavoring agents, or combinations thereof.

The active compounds can be effective over a wide dosage range and are generally administered in a pharmaceutically effective amount. It will be understood, however, that the amount of the compound actually administered and the schedule of administration will usually be determined by a physician, according to the relevant circumstances, including the condition to be treated, the chosen route of administration, the actual compound administered, the age, weight, and response of the individual subject, the severity of the subject's symptoms, and the like.

Methods of Use and Combination Therapies

The present application further provides methods of treating prostate cancer in a patient in need thereof. As used herein, the term "patient" refers to any animal, including mammals, for example, mice, rats, other rodents, rabbits, dogs, cats, swine, cattle, sheep, horses, primates, and humans. In some embodiments, the patient is a human. In some embodiments, the method comprises administering to the patient a therapeutically effective amount of a compound provided herein (e.g., a compound provided in Table 1), or a pharmaceutically acceptable salt thereof. In some embodiments, the compound is 2,2'-[1-(4-amino-1,2,5-oxadiazol-3-yl)-1H-1,2,3-triazole-4,5-diyl]di(2-butanol) (1), or a pharmaceutically acceptable salt thereof. In some embodiments, the compound is 3-[5-(2-thienyl)-2-furyl]propanoic acid (31), or a pharmaceutically acceptable salt thereof.

In some embodiments, the prostate cancer comprises a cancer selected from the group consisting of acinar adenocarcinoma, atropic adenocarcinoma, foamy adenocarcinoma, colloid adenocarcinoma, signet ring carcinoma, ductal adenocarcinoma transitional cell (or urothelial) cancer, squamous cell cancer, carcinoid, small cell cancer, sarcoma cancer, sarcomatoid cancer, and castration resistant prostate cancer (CRPC). In some embodiments, the prostate cancer is castration resistant prostate cancer (CRPC).

In some embodiments, a compound provided herein (e.g., a compound provided in Table 1), or a pharmaceutically acceptable salt thereof is administered in combination with one or more additional therapies. In some embodiments, at least one of the one or more additional therapies is selected from the group consisting of administration of a chemotherapeutic agent, radiation therapy, a surgical procedure, androgen deprivation therapy, or any combination thereof. In some embodiments, at least one of the one or more additional therapies comprises administration of at least one chemotherapeutic agent. In some embodiments, at least one of the one or more additional therapies comprises androgen deprivation therapy. In some embodiments, at least one of the one or more additional therapies is androgen deprivation therapy. In some embodiments, a compound provided herein, or a pharmaceutically acceptable salt thereof, is administered prior to the one or more additional therapies. In some embodiments, a compound provided herein, or pharmaceutically acceptable salt thereof, is administered concurrently with the one or more additional therapies. In some embodiments, a compound provided herein, or a pharmaceutically acceptable salt thereof, is administered after the one or more additional therapies.

In some embodiments, the compound is 2,2'-[1-(4-amino-1,2,5-oxadiazol-3-yl)-1H-1,2,3-triazole-4,5-diyl]di(2-butanol) (1), or a pharmaceutically acceptable salt thereof, and at least one of the one or more additional therapies is androgen deprivation therapy. In some embodiments, the compound is 3-[5-(2-thienyl)-2-furyl]propanoic acid (31), or a pharmaceutically acceptable salt thereof, and at least one of the one or more additional therapies is androgen deprivation therapy.

In some embodiments, the method comprises:
i) administering to the patient a therapeutically effective amount of 2,2'-[1-(4-amino-1,2,5-oxadiazol-3-yl)-1H-1,2,3-triazole-4,5-diyl]di(2-butanol) (1), or a pharmaceutically acceptable salt thereof; and
ii) administering androgen deprivation therapy.

In some embodiments, the method comprises:
i) administering to the patient a therapeutically effective amount of 3-[5-(2-thienyl)-2-furyl]propanoic acid (31), or a pharmaceutically acceptable salt thereof; and
ii) administering androgen deprivation therapy.

The present application further provides a method of modulating an activity of UDP-glucose dehydrogenase (UGDH) in a cell, the method comprising contacting the cell with an effective amount of a compound provided herein (e.g., a compound provided in Table 1), or a pharmaceutically acceptable salt thereof. In some embodiments, the modulating an activity of UDP-glucose dehydrogenase (UGDH) comprises inhibiting UDP-glucose dehydrogenase (UGDH). In some embodiments, the compound is 2,2'-[1-(4-amino-1,2,5-oxadiazol-3-yl)-1H-1,2,3-triazole-4,5-diyl]di(2-butanol) (1), or a pharmaceutically acceptable salt thereof. In some embodiments, the compound is 3-[5-(2-thienyl)-2-furyl]propanoic acid (31), or a pharmaceutically acceptable salt thereof.

The present application further provides a method of treating a prostate cancer mediated by UDP-glucose dehydrogenase (UGDH) in a patient in need thereof, the method comprising administering a therapeutically effective amount of a compound provided herein (e.g., a compound provided in Table 1), or a pharmaceutically acceptable salt thereof.

In some embodiments, the prostate cancer comprises a cancer selected from the group consisting of acinar adenocarcinoma, atropic adenocarcinoma, foamy adenocarcinoma, colloid adenocarcinoma, signet ring carcinoma, ductal adenocarcinoma transitional cell (or urothelial) cancer, squamous cell cancer, carcinoid, small cell cancer, sarcoma cancer, sarcomatoid cancer, and castration resistant prostate cancer (CRPC). In some embodiments, the prostate cancer is castration resistant prostate cancer (CRPC).

In some embodiments, the compound is 2,2'-[1-(4-amino-1,2,5-oxadiazol-3-yl)-1H-1,2,3-triazole-4,5-diyl]di(2-butanol) (1), or a pharmaceutically acceptable salt thereof. In some embodiments, the compound is 3-[5-(2-thienyl)-2-furyl]propanoic acid (31), or a pharmaceutically acceptable salt thereof.

The present application further provides a method of predicting patient response to prostate cancer therapy, comprising:
a) obtaining a biopsy sample from the patient, wherein the biopsy sample comprises prostate cancer cells and non-cancerous tissue cells; and
b) comparing the UDP-glucose dehydrogenase (UGDH) expression in the prostate cancer cells and the non-cancerous tissue cells;
wherein when the UDP-glucose dehydrogenase (UGDH) expression is greater in the prostate cancer cells compared to the UDP-glucose dehydrogenase (UGDH) expression in the non-cancerous tissue cells, then the patient is more likely to respond to the prostate cancer therapy.

In some embodiments, the prostate cancer cells comprise a prostate cancer selected from the group consisting of acinar adenocarcinoma cells, atropic adenocarcinoma cells, foamy adenocarcinoma cells, colloid adenocarcinoma cells, signet ring carcinoma cells, ductal adenocarcinoma transitional cell (or urothelial) cancer cells, squamous cell cancer cells, carcinoid cells, small cell cancer cells, sarcoma cancer cells, sarcomatoid cancer cells, and castration resistant prostate cancer (CRPC) cells. In some embodiments, the prostate cancer cells comprise castration resistant prostate cancer (CRPC) cells. In some embodiments, the prostate cancer is castration resistant prostate cancer (CRPC).

As used herein, the term "non-cancerous tissue cells" refers to non-cancerous tissue cells in the area surrounding the prostate cancer cells. For example, non-cancerous tissue cells may refer to non-cancerous prostate tissue cells, non-cancerous acini, and normal-appearing acini (NAA). In some embodiments, the non-cancerous or normal-appearing acini are selected from the group consisting of acini of the stomach, acini of the sebaceous gland of the scalp, acini of the liver, acini of the lung, acini of the lacrimal gland, acini of mammary gland, acini of the pancreas, and acini of the prostate. In some embodiments, the non-cancerous tissue cells comprise prostate tissue cells. In some embodiments, the non-cancerous tissue cells are prostate tissue cells. In some embodiments, the non-cancerous tissue cells comprise non-cancerous acini or normal-appearing acini (NAA). In some embodiments, the non-cancerous cells comprise normal-appearing acini. Examples of normal-appearing acini that may be used in the method provided herein may be found, for example, in Huang et al., *Int. J. Cancer*, 2010, 126(5), 315-327, the disclosure of which is incorporated herein in its entirety.

In some embodiments, the comparing comprises determining the ratio of UDP-glucose dehydrogenase (UGDH) expression in the prostate cancer cells and UDP-glucose dehydrogenase (UGDH) expression in the non-cancerous tissue cells. In some embodiments, the comparing comprises:

a) immunofluorescence staining of the biopsy sample; and b) quantifying the fluorescence pixel intensity of acini within the prostate cancer cells and the non-cancerous tissue cells.

In some embodiments, the quantifying comprises determining the average mean pixel intensity acini within the prostate cancer cells and acini within the non-cancerous tissue cells (e.g., non-cancerous acini or normal-appearing acini (NAA)).

In some embodiments, the patient is more likely to respond to prostate cancer therapy when the average mean pixel intensity of acini within the prostate cancer cells is at least about 10% greater than the average mean pixel intensity of acini within the non-cancerous tissue cells (e.g., non-cancerous acini or normal-appearing acini (NAA)), for example, at least about 10%, at least about 15% at least about 20%, at least about 25%, at least about 30%, at least about 40%, at least about 50%, at least about 60%, at least about 70%, at least about 80%, at least about 90%, or at least about 100%. In some embodiments, the patient is more likely to respond to prostate cancer therapy when the average mean pixel intensity of acini within the prostate cancer cells is at least about 15% greater than the average mean pixel intensity of acini within the non-cancerous tissue cells (e.g., non-cancerous acini or normal-appearing acini (NAA)).

In some embodiments, the prostate cancer therapy is selected from the group consisting of administration of a chemotherapeutic agent, radiation therapy, a surgical procedure, androgen deprivation therapy, or any combination thereof. In some embodiments, a compound provided herein (e.g., a compound provided in Table 1), or a pharmaceutically acceptable salt thereof, is administered prior to the prostate cancer therapy. In some embodiments, a compound provided herein, or pharmaceutically acceptable salt thereof, is administered concurrently with the prostate cancer therapy. In some embodiments, a compound provided herein, or a pharmaceutically acceptable salt thereof, is administered after the prostate cancer therapy. In some embodiments, the prostate cancer therapy comprises administration of at least one chemotherapeutic agent. In some embodiments, the prostate cancer therapy comprises androgen deprivation therapy. In some embodiments, the prostate cancer therapy is androgen deprivation therapy.

The present application further provides a method of treating a prostate cancer mediated by UDP-glucose dehydrogenase (UGDH) in a patient in need thereof, the method comprising:

a) obtaining a biopsy sample from the patient, wherein the biopsy sample comprises prostate cancer cells and non-cancerous tissue cells;

b) comparing the UDP-glucose dehydrogenase (UGDH) expression in the prostate cancer cells and the non-cancerous tissue cells; and c) if the prostate cancer is determined to be associated with one or more of overexpression and amplification of UDP-glucose dehydrogenase (UGDH) in the prostate cancer cells compared to the non-cancerous tissue cells, administering a therapeutically effective amount of a compound provided herein, or a pharmaceutically acceptable salt thereof.

In some embodiments, the prostate cancer is determined to be associated with one or more of overexpression and amplification of UDP-glucose dehydrogenase (UGDH) in the prostate cancer cells compared to the non-cancerous tissue cells when the average mean pixel intensity of acini within the prostate cancer cells is at least about 10% greater than the average mean pixel intensity of acini within the non-cancerous tissue cells (e.g., non-cancerous acini or normal-appearing acini (NAA)), for example, at least about 10%, at least about 15% at least about 20%, at least about 25%, at least about 30%, at least about 40%, at least about 50%, at least about 60%, at least about 70%, at least about 80%, at least about 90%, or at least about 100%. In some embodiments, the patient is more likely to respond to prostate cancer therapy when the average mean pixel intensity of acini within the prostate cancer cells is at least about 15% greater than the average mean pixel intensity of acini within the non-cancerous tissue cells (e.g., non-cancerous acini or normal-appearing acini (NAA)).

In some embodiments, the prostate cancer is determined to be associated with one or more of overexpression and amplification of UDP-glucose dehydrogenase (UGDH) in the prostate cancer cells compared to the non-cancerous tissue cells when the expression of UGDH within the prostate cancer cells is at least about 10% greater than the expression of UGDH within the non-cancerous tissue cells (e.g., non-cancerous acini or normal-appearing acini (NAA)), for example, at least about 10%, at least about 15% at least about 20%, at least about 25%, at least about 30%, at least about 40%, at least about 50%, at least about 60%, at least about 70%, at least about 80%, at least about 90%, or at least about 100%. In some embodiments, the patient is more likely to respond to prostate cancer therapy when the expression of UGDH is within the prostate cancer cells is at least about 15% greater than the expression of UGDH within the non-cancerous tissue cells (e.g., non-cancerous acini or normal-appearing acini (NAA)).

In some embodiments, the method further comprises administration of one or more additional therapies. In some embodiments, at least one of the one or more additional therapies is selected from the group consisting of administration of a chemotherapeutic agent, radiation therapy, a surgical procedure, androgen deprivation therapy, or any combination thereof. In some embodiments, at least one of the one or more additional therapies administering at least one chemotherapeutic agent. In some embodiments, at least one of the one or more additional therapies comprises androgen deprivation therapy. In some embodiments, at least one of the one or more additional therapies is androgen deprivation therapy. In some embodiments, a compound provided herein (e.g., a compound provided in Table 1), or a pharmaceutically acceptable salt thereof, is administered prior to the one or more additional therapies. In some embodiments, a compound provided herein, or pharmaceutically acceptable salt thereof, is administered concurrently with the one or more additional therapies. In some embodiments, a compound provided herein, or a pharmaceutically acceptable salt thereof, is administered after the one or more additional therapies.

In some embodiments, the compound is 2,2'-[1-(4-amino-1,2,5-oxadiazol-3-yl)-1H-1,2,3-triazole-4,5-diyl]di(2-butanol) (1), or a pharmaceutically acceptable salt thereof. In some embodiments, the compound is 3-[5-(2-thienyl)-2-furyl]propanoic acid (31), or a pharmaceutically acceptable salt thereof.

The present application further provides a method of improving the efficacy of androgen deprivation therapy in a patient, comprising administering to the patient a therapeutically effective amount of a UDP-glucose dehydrogenase (UGDH) inhibitor.

In some embodiments, the prostate cancer comprises a cancer selected from the group consisting of acinar adenocarcinoma, atropic adenocarcinoma, foamy adenocarcinoma, colloid adenocarcinoma, signet ring carcinoma, ductal adenocarcinoma transitional cell (or urothelial) cancer, squamous cell cancer, carcinoid, small cell cancer, sarcoma cancer, sarcomatoid cancer, and castration resistant prostate cancer (CRPC). In some embodiments, the prostate cancer is castration resistant prostate cancer (CRPC).

In some embodiments, the UDP-glucose dehydrogenase (UGDH) inhibitor is selected from a compound provided herein (e.g., a compound provided in Table 1), or a pharmaceutically acceptable salt thereof. In some embodiments, the compound is 2,2'-[1-(4-amino-1,2,5-oxadiazol-3-yl)-1H-1,2,3-triazole-4,5-diyl]di(2-butanol) (1), or a pharmaceutically acceptable salt thereof. In some embodiments, the compound is 3-[5-(2-thienyl)-2-furyl]propanoic acid (31), or a pharmaceutically acceptable salt thereof.

EXAMPLES

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results.

Example 1

High Throughput Screening for Inhibitors of UDP-Glucose Dehydrogenase i. Reagents UDP-glucose Dehydrogenase
Stock 2.5 mg/ml
Stored at −80°, as aliquots of 2 mL, don't refreeze
Storage buffer: 20 mM Tris pH 7.4, 1 mM DTT
$NAD^+$ (MW = 663.4), Sigma N1511
Make 50 mM stock in PBS fresh each day.
Do not store overnight, even if frozen.
UDP-glucose (MW = 610), Sigma U4625
Stock 100 mM in water
Stored at −20°. Do not refreeze.
BSA, Meso Scale Discovery, Blocker A, catalog# R93BA-1
Stock 5.6% in PBS (W/V).
Alliquot and store at −20°
UDP-xylose, lot VX0707 (MW = 554.3), supplied by CaraboSource Services, CCRC/University of Georgia
Stock 1 mM in PBS
Stored at −20°, as aliquots of 1 ml. Don't re-freeze
DMSO (MW = 78.1), Fisher D136-1
PBS, pH 7.4, Sigma #P3813
Dissolve in 1 L water and store at room temp.
NADH (MW = 742), Sigma N4505
Stock 10 mM in PBS
Store at −20° as aliquots of 100 μl. Do not re-freeze.

ii. Cocktails
Enzyme Buffer 2.8×
 14 μg/mL enzyme;
 0.56% BSA; and
 In PBS, pH 7.4.

Preparation of 1 liter: Prepare enzyme in polypropylene. Do not let enzyme touch glass or polystyrene. Because the enzyme is the least stable of all reagents used in the assay, it should be prepared last. Enzyme buffer should be kept cold if any time passes before use.
 1. 900 mL PBS;
 2. 100 mL 5.6% BSA stock; and
 3. 5.6 mL of 2500 μg/mL enzyme stock
Substrate Solution 2.8×
 700 μM NAD+;
 92.4 μM UDP-glucose; and
 In PBS, pH 7.4.
 Preparation of 1 L:
 1. 1 liter PBS;
 2. 14 mL of 50 mM NAD+ stock; and
 3. 9.24 mL of 10 mM UDP-glucose stock or 924 μL of 100 mM UDP-glucose stock.
Positive Control Solution 3.5×
 70 μM UDP-xylose;
 2.5% DMSO; and
 In PBS, pH 7.4
 Preparation of 100 mL:
 1. 97.5 mL PBS;
 2. 2.5 mL DMSO; and
 3. 7 mL 1 mM UDP-xylose stock
Negative Control Solution 3.5×
 2.5% DMSO; and
 In PBS, pH 7.4.
 Preparation of 100 mL:
 1. 97.5 mL PBS
 2. 2.5 mL DMSO
Instruments and Lab-Equipment
 16-channel Finnpipette 5-50 μl
 2 Thermo Scientific Multidrop 384 & cassettes.
 Tecan Safire$^2$.
 Microtiterplates: Greiner FLUOTRAC 200
iii. Methodology
 1. Preparation of the Compound-Plates: Add Positive & Negative Controls
  Plates are stored at −20° with 20 μL/well of 25 μg/mL compound in 2.5% DMSO in water.
   a. Dispense, with the 16channel Finnpipette, 20 μL of the negative control solution (2.5% DMSO) in column 1.
   b. Dispense, with the 16channel Finnpipette, 20 μL of the positive control solution (2.5% DMSO & 70 μM UDP-glucose) in column 2.
 2. First Addition: Add Enzyme to Compounds
  a. Dispense, with the Multidrop 384, 25 μL/well Enzyme solution.
  b. Incubate for 5 minutes at room temperature. Incubation starts as soon as the Multidrop Micro starts adding Enzyme Solution. Incubation has ended when the Multidrop 384 starts adding Substrate solution. So the next step is done while the plates are incubating.
 3. First Read: Measure Baseline (Compound) Fluorescence.
 4. Second Addition: Add Substrates to Enzyme & Compounds
  a. Dispense, with the Multidrop 384, 25 μL/well Substrate solution.
  b. Incubate again for 30 minutes at RT. Again, incubation starts as soon as the Multidrop Micro starts adding Substrate Solution. However, incubation has ended when the Safire$^2$ starts reading the plate. Keep plates stacked with an empty plate on top of the stack to prevent photobleaching and evaporation.

5. Second Read: Measure NADH Levels

6. Standard Curves:

In a separate plate, prepare an 11-point, 2× serial dilution of NADH in 0.2% BSA in PBS. Leave one "no NADH" point. Use BSA from the same stock used to make the Enzyme Solution. Start the serial dilution at 100 µM NADH. Dispense 70 µL/well in quadruplicate Plates can be run in batches up to 25. FIG. 1. provides a gantt chart which shows how the assay timing would work.

iv. Data-Analysis

All data is converted to NADH concentration using the standard curve generated each day. All data is converted to: [second read–the first read]. Because NADH is generated in the reaction, an increase in NADH signals enzyme activity. Percent of Controls (POC) expresses the activity of a compound relative to the positive and negative controls (Equation 1).

$$\% \text{ of controls} = \frac{(C_{CMPD} - C_{NEG})}{(C_{POS} - C_{NEG})}. \quad \text{Equation 1}$$

$C_{CMPD}$=NADH concentration measured in a well containing compound $C_{NEG}$=NADH concentration measured in a negative control well (DMSO only)

$C_{POS}$=NADH concentration measured in a positive control well (UDP-xylose)

Note that the positive control wells (with UDP-xylose) will have lower value (less NADH) than will negative control wells. So the denominator in this equation will be a negative number. An active (inhibitory) compound will also result in a lower value, so the numerator will also be negative. Thus, the higher the POC, the more inhibitory the compound is (see e.g., Table 2).

TABLE 2

POC Values

| POC Value | Compound Effect |
|---|---|
| <0% | Test compound speeds up the reaction |
| =0% | Test compound is not active |
| >0% | Test compound is inhibitory |
| =100% | Test compound is as inhibitory as is 20 µM UDP-glucose |
| >100% | Test compound is more inhibitory than is 20 µM UDP-glucose |

Table 3 shows POC values for compounds screened in the high throughput assay.

TABLE 3

Compound Data

| Compound Structure | POC |
|---|---|
| (structure) | 61% |
| (structure) | 73% |
| (structure) | 86% |
| (structure) | 46% |
| (structure) | 83% |
| (structure) | 81% |

TABLE 3-continued
Compound Data
| Compound Structure | POC |
|---|---|
| 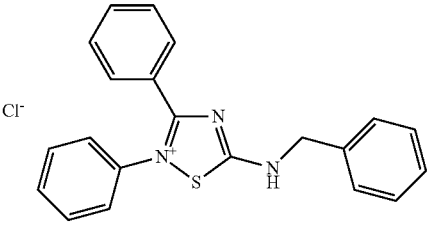 [SMILES: [Cl-] ; c1ccc(CNc2nc(-c3ccccc3)[n+](-c3ccccc3)s2)cc1] | 106% |
| 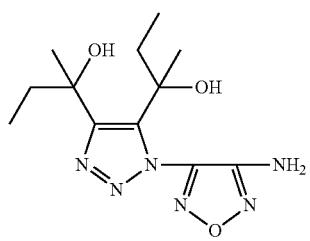 | 101% |
| 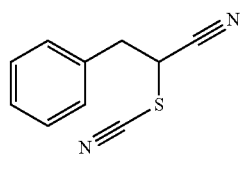 [SMILES: N#CSC(C#N)Cc1ccccc1] | 59% |
| 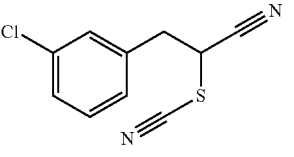 [SMILES: N#CSC(C#N)Cc1cccc(Cl)c1] | 74% |
| 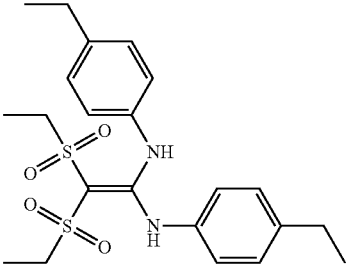 [SMILES: CCc1ccc(NC(Nc2ccc(CC)cc2)=C(S(=O)(=O)CC)S(=O)(=O)CC)cc1] | 47% |
| 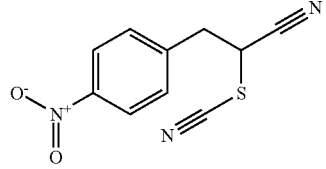 [SMILES: N#CSC(C#N)Cc1ccc([N+](=O)[O-])cc1] | 80% |
| 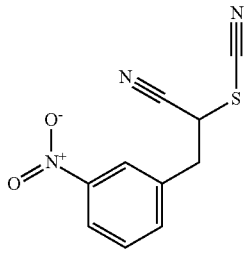 [SMILES: N#CSC(C#N)Cc1cccc([N+](=O)[O-])c1] | 88% |
TABLE 3-continued
Compound Data
| Compound Structure | POC |
|---|---|
| 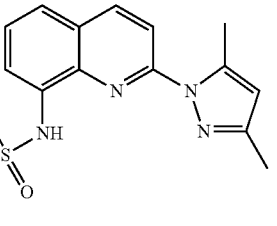 | 148% |
| 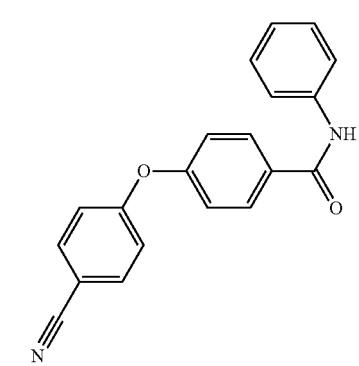 [SMILES: N#Cc1ccc(Oc2ccc(C(=O)Nc3ccccc3)cc2)cc1] | 54% |
| 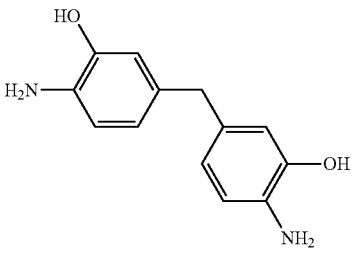 [SMILES: Nc1ccc(Cc2ccc(N)c(O)c2)cc1O] | 62% |
| 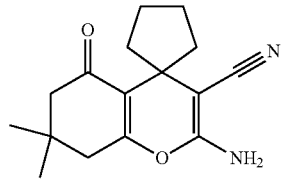 [SMILES: CC1(C)CC(=O)C2=C(C1)OC(N)=C(C#N)C21CCCC1] | 126% |
| 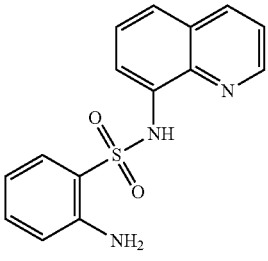 | 72% |
| 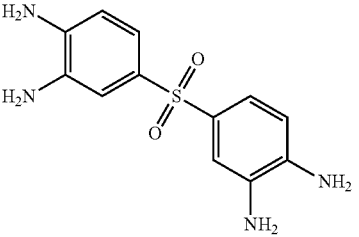 [SMILES: Nc1ccc(S(=O)(=O)c2ccc(N)c(N)c2)cc1N] | 50% |

TABLE 3-continued

| Compound Structure | POC |
|---|---|
| (quinoline with nitro and dimethylpyrazole) | 88% |
| (bis(3,4-diaminophenyl) ketone) | 46% |
| (N-(4-nitrophenyl)-5-bromofuran-2-carboxamide) | 62% |
| (furazano-furazan with morpholine) | 105% |
| (4-methyl-3-(N-(4-methoxyphenyl)sulfamoyl)-N-(4-carboxyphenyl)benzamide) | 61% |
| (dimethyl benzofurazan di-N-oxide) | 63% |
| (2-amino-5-(4-methoxyphenyl)-1,3,4-oxadiazole) | 86% |

TABLE 3-continued

| Compound Structure | POC |
|---|---|
| (3-bromobenzoyl norleucine) | 103% |
| (nitro-methyl-thiophene sulfone vanillylidene) | 65% |
| (3,4,5-trimethoxyphenyl-2-nitropropene) | 61% |
| (4-nitrophenylacetamide dimethylthiophene carboxamide) | 75% |
| (4-hydroxy-3-methoxyphenyl-2-nitrobutene) | 63% |
| (2,6-di-tert-butyl-4-(methoxymethyl)benzene-1,3-diol) | 56% |

TABLE 3-continued

Compound Data

| Compound Structure | POC |
|---|---|
| (2-amino-6-methyl-4,5,6,7-tetrahydrothieno[2,3-c]pyridine-3-carbonitrile) | 55% |
| (2-amino-5-(3,5-dichloro-2,6-dihydroxy-4-chlorophenyl)thiazole) HCl | 71% |
| (2-(cyclohexylamino)-5-thiocyanato-thiazole) | 66% |
| (N-(4-(3-(furan-2-yl)acryloyl)phenyl)furan-2-carboxamide) | 55% |
| (5-amino-2-(o-tolyl)-1,3,4-thiadiazole) | 51% |
| (dihydropyridine with cyano, pyridyl, acetyl, methyl, and 3-nitrobenzylthio substituents) | 51% |
| (2-(2-methyl-3-nitrobenzamido)-4-ethyl-5-methylthiophene-3-carboxamide) | 58% |

TABLE 3-continued

Compound Data

| Compound Structure | POC |
|---|---|
| (2-(2-methylfuran-3-carboxamido)-4-ethyl-5-methylthiophene-3-carboxamide) | 50% |
| (N-(2,3-dihydrobenzo[b][1,4]dioxin-6-yl)benzofuran-2-carboxamide) | 103% |
| (2-(tetrahydrofuran-2-carboxamido)-cycloocta[b]thiophene-3-carboxamide) | 74% |
| (5-nitro-2-(furan-2-yl)-1H-benzimidazole) | 46% |
| (2-(5-bromofuran-2-yl)-2,3-dihydro-1H-benzimidazole) | 65% |
| (8-amino-9-hydroxy-2-methyl-4H-pyrido[1,2-a]pyrimidin-4-one) | 50% |

TABLE 3-continued
| Compound Structure | POC |
|---|---|
| 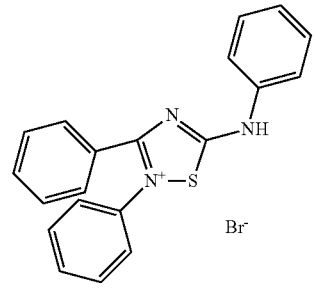 [SMILES: c1ccc(Nc2nc(-c3ccccc3)[n+](-c3ccccc3)s2)cc1 ; [Br-]] | 52% |
| 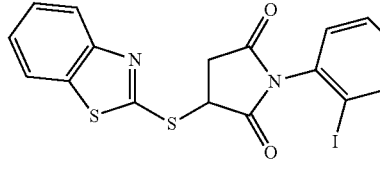 | 58% |
| 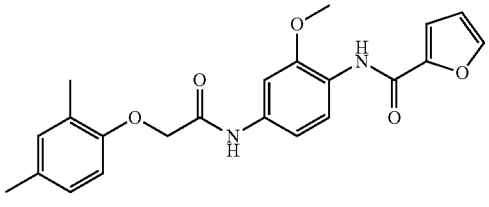 [SMILES: COc1cc(NC(=O)COc2ccc(C)cc2C)ccc1NC(=O)c1ccco1] | 70% |
| 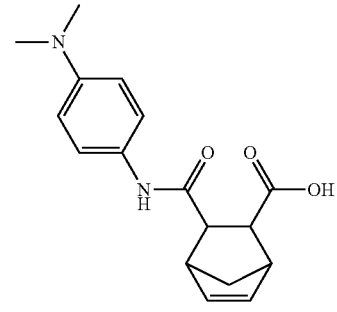 [SMILES: CN(C)c1ccc(NC(=O)C2C3C=CC(C3)C2C(=O)O)cc1] | 56% |
| 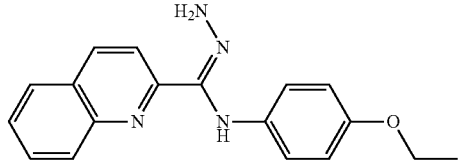 [SMILES: CCOc1ccc(N/C(=N/N)c2ccc3ccccc3n2)cc1] | 66% |
| 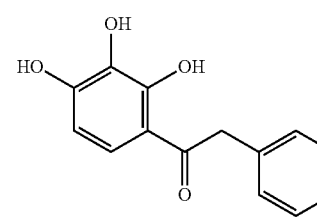 | 46% |
| | 57% |
| | 46% |
| | 57% |
| | 62% |
| | 82% |
| | 87% |
| | 49% |
| | 57% |

TABLE 3-continued
| Compound Structure | POC |
|---|---|
| 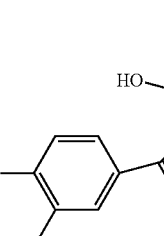 | 51% |
| 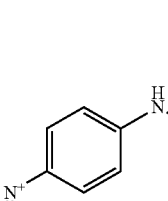 | 47% |
| 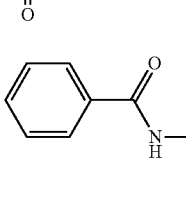 | 46% |
| 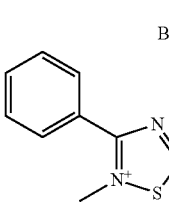 | 58% |
| 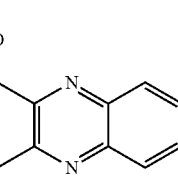 | 47% |
| 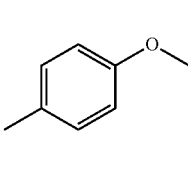 | 85% |
| 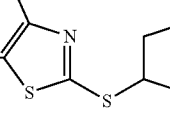 | 68% |
TABLE 3-continued
| Compound Structure | POC |
|---|---|
| 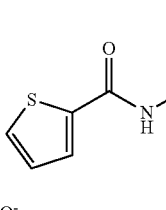 | 47% |
| 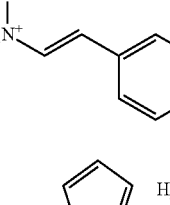 | 45% |
| 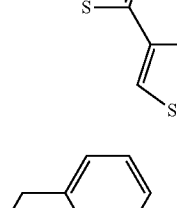 | 67% |
| 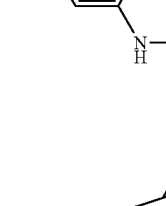 | 46% |
| 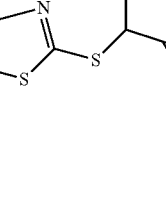 | 45% |
| 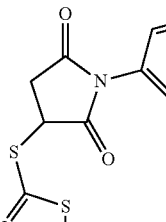 | 47% |
| | 58% |

TABLE 3-continued

Compound Data

| Compound Structure | POC |
|---|---|
| (structure) | 45% |
| (structure) | 50% |
| (structure) | 48% |
| (structure) | 51% |
| (structure) | 73% |
| (structure) | 73% |
| (structure) | 59% |
| (structure) | 83% |

TABLE 3-continued

Compound Data

| Compound Structure | POC |
|---|---|
| (chemical structure: epigallocatechin digallate-like) | 67% |
| (chemical structure: theaflavin-type dimer) | 83% |
| (chemical structure: epigallocatechin gallate) | 76% |
| (chemical structure: theaflavin derivative) | 76% |
| gallic acid | 71% |
| purpurogallin-type tropolone | 73% |
| hexa-acetylated flavone | 98% |
| myricetin-type flavone | 98% |
| phenylmercuric acetate | 99% |

TABLE 3-continued
| Compound Structure | POC |
|---|---|
| 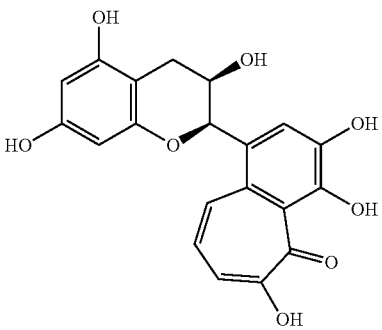 [SMILES: O=c1c(O)cccc2c([C@H]3Oc4cc(O)cc(O)c4C[C@H]3O)cc(O)c(O)c12] | 53% |
| 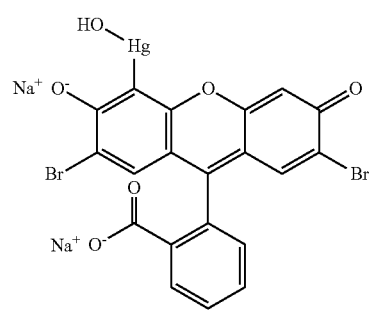 | 97% |
| 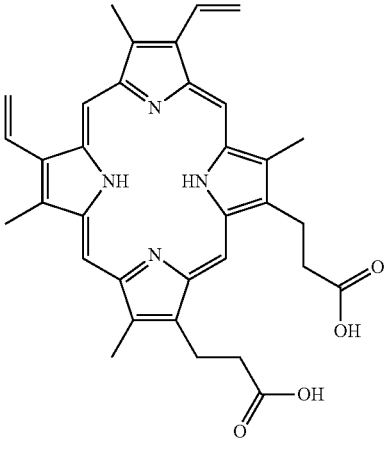 [SMILES: C=CC1=C(C)c2cc3[nH]c(cc4nc(cc5[nH]c(cc1n2)c(C)c5CCC(=O)O)C(CCC(=O)O)=C4C)c(C)c3C=C] | 58% |
| 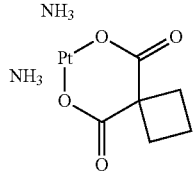 | 61% |
| 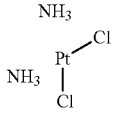 | 73% |
| 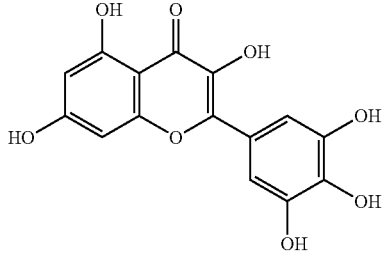 [SMILES: O=c1c(O)c(-c2cc(O)c(O)c(O)c2)oc2cc(O)cc(O)c12] | 91% |
| 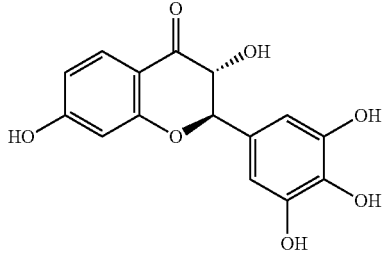 [SMILES: O=C1c2ccc(O)cc2O[C@H](c2cc(O)c(O)c(O)c2)[C@H]1O] | 96% |
| 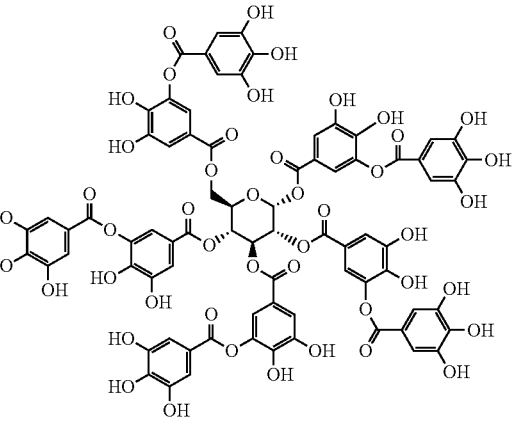 | 69% |
| 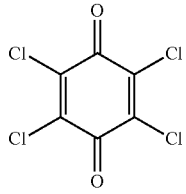 [SMILES: O=C1C(Cl)=C(Cl)C(=O)C(Cl)=C1Cl] | 79% |
| 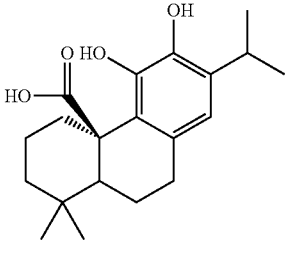 | 66% |

Example 2

Androgen Deprivation Model and UGDH Knockdown

Figure 2:
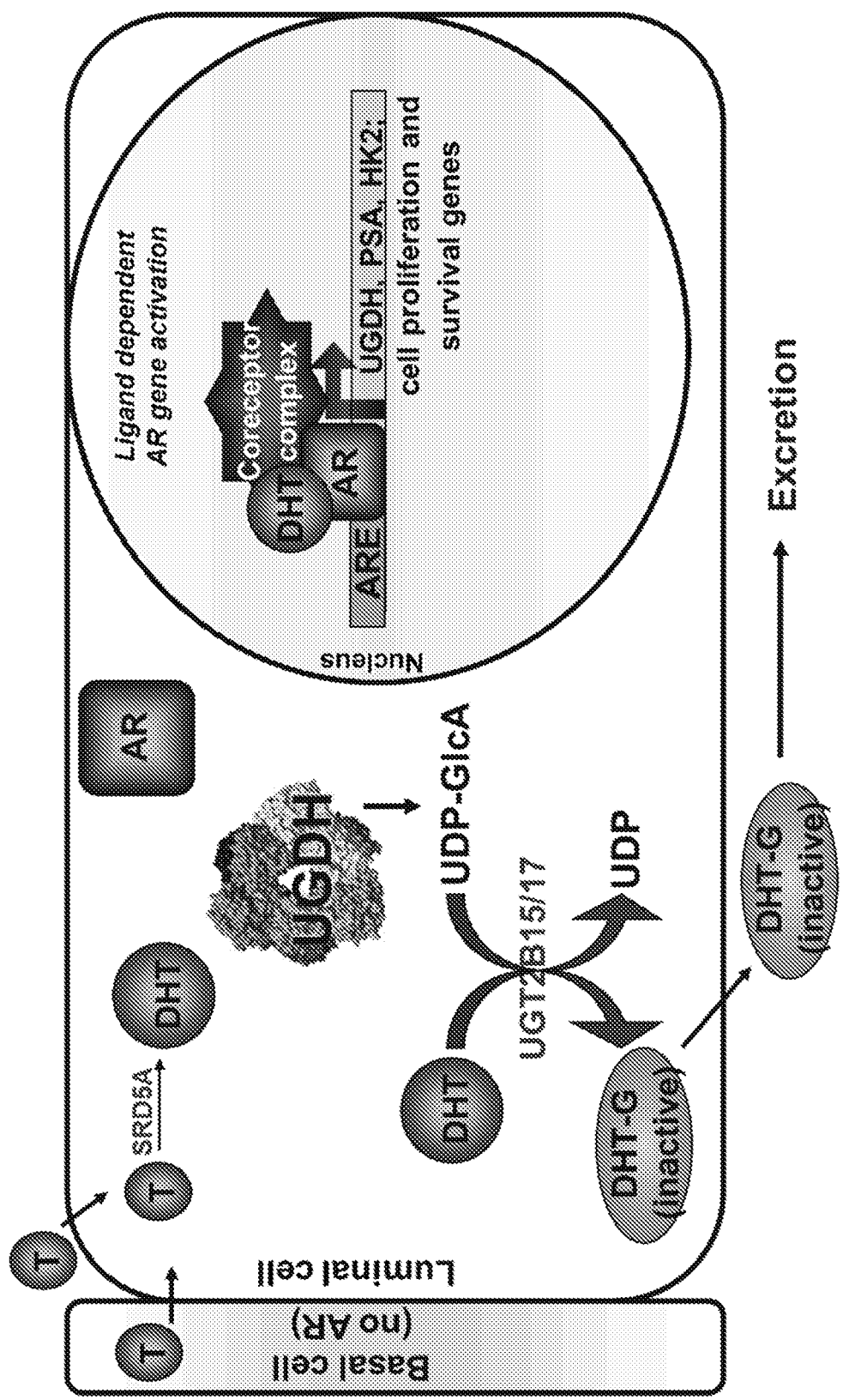
FIG. 2 is a diagram showing a mechanism wherein UGDH provides precursors for androgen inactivation by UGT-mediated glucuronidation.
Figure 3A:
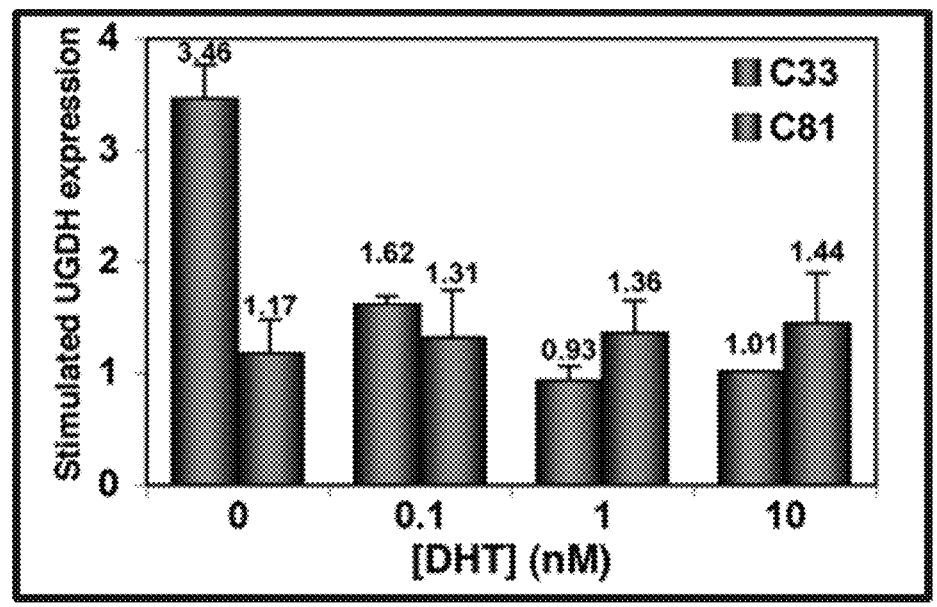
FIGS. 3A-3C shows results of a simulated androgen deprivation therapy assay. For FIG. 3A: Left Bar=C33; Right Bar=C81. For FIG. 3B: Left Bar=3 days; Right Bar=15 days. For FIG. 3C: Left Bar=Basal; Right Bar=DHT 24 h.
Figure 3B:
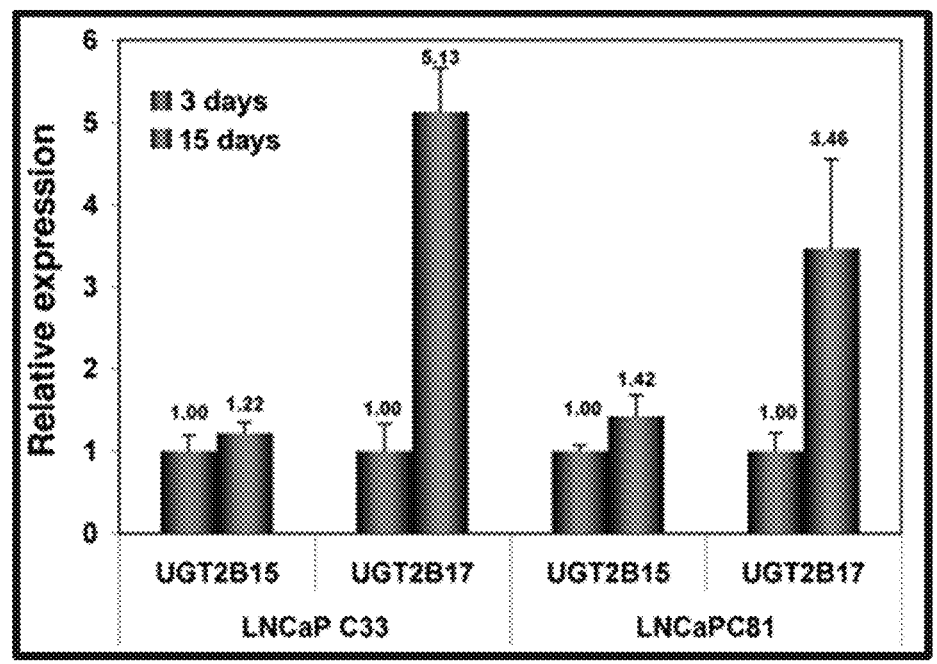
Figure 3C:
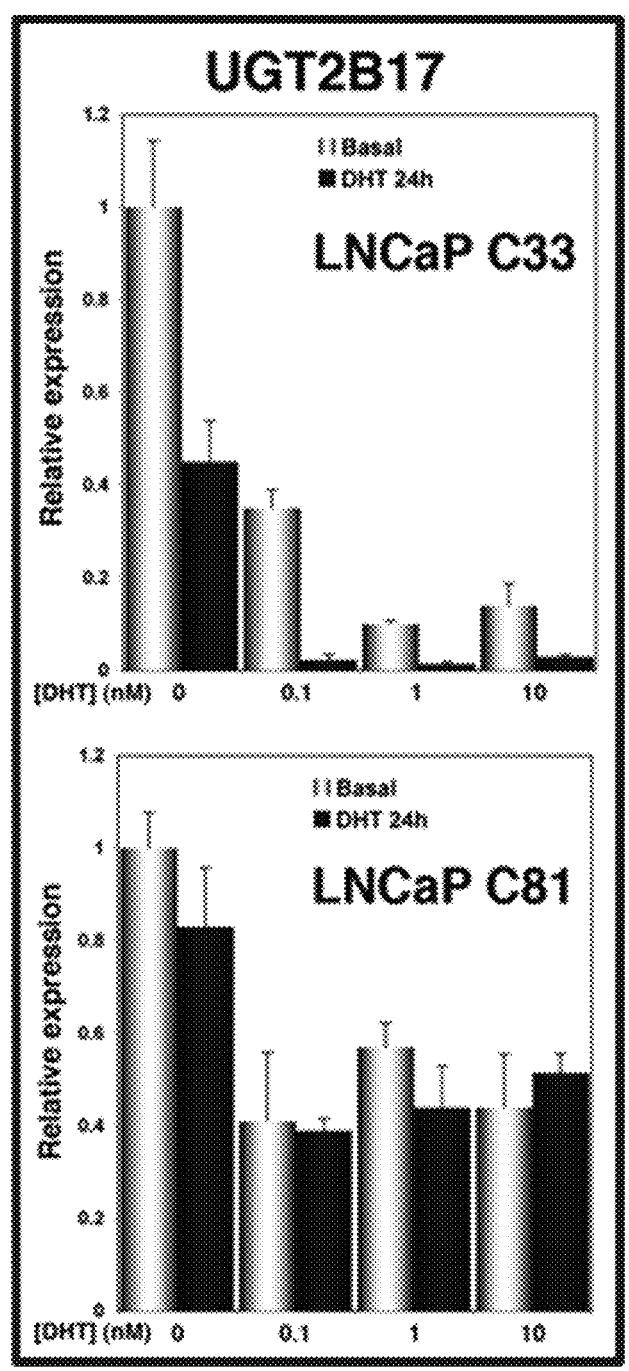
Figure 4:
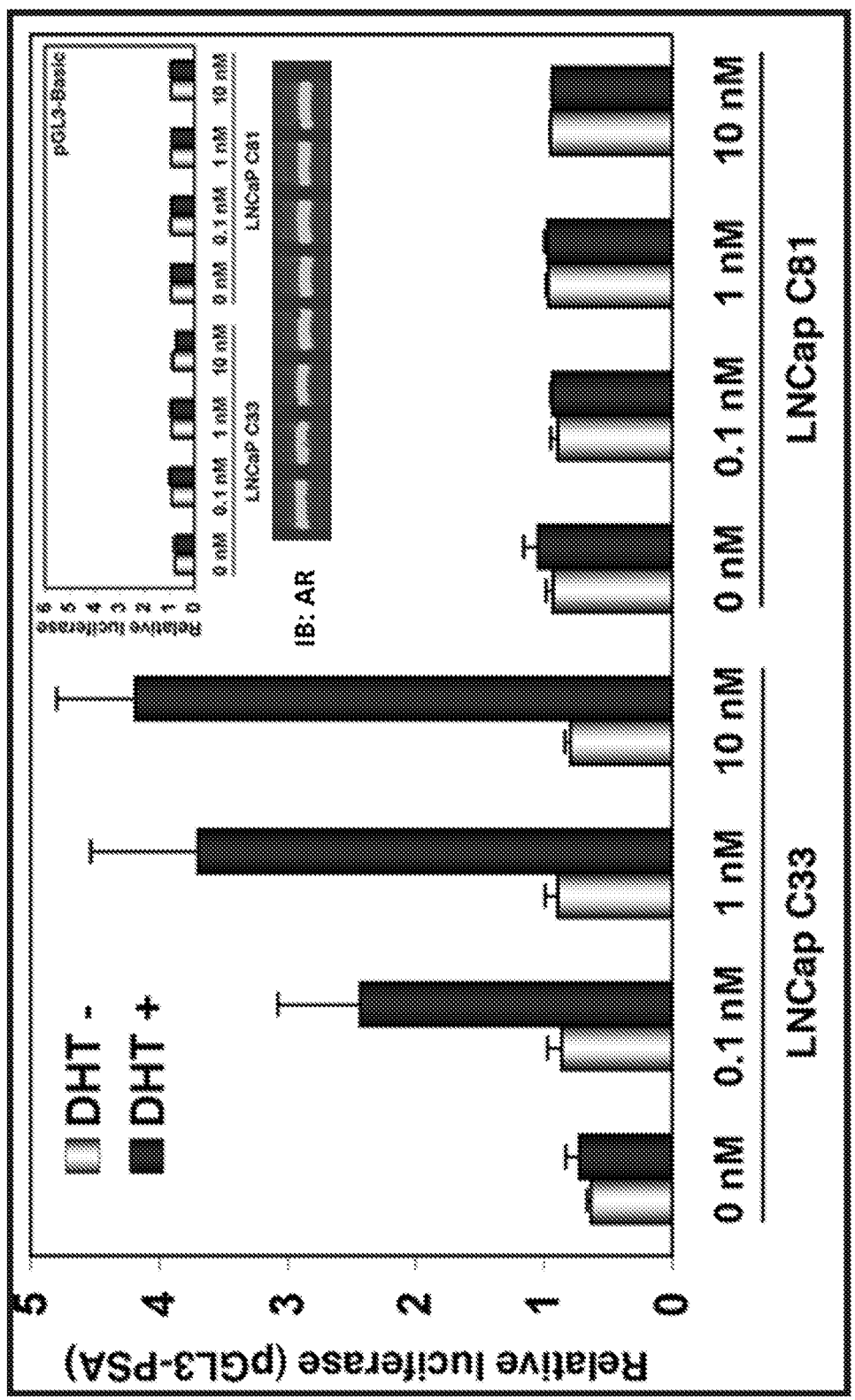
FIG. 4. shows modulation of function of AR using a luciferase reporter assay driven by the AR-stimulated PSA promoter/enhancer region.
Figure 5A:
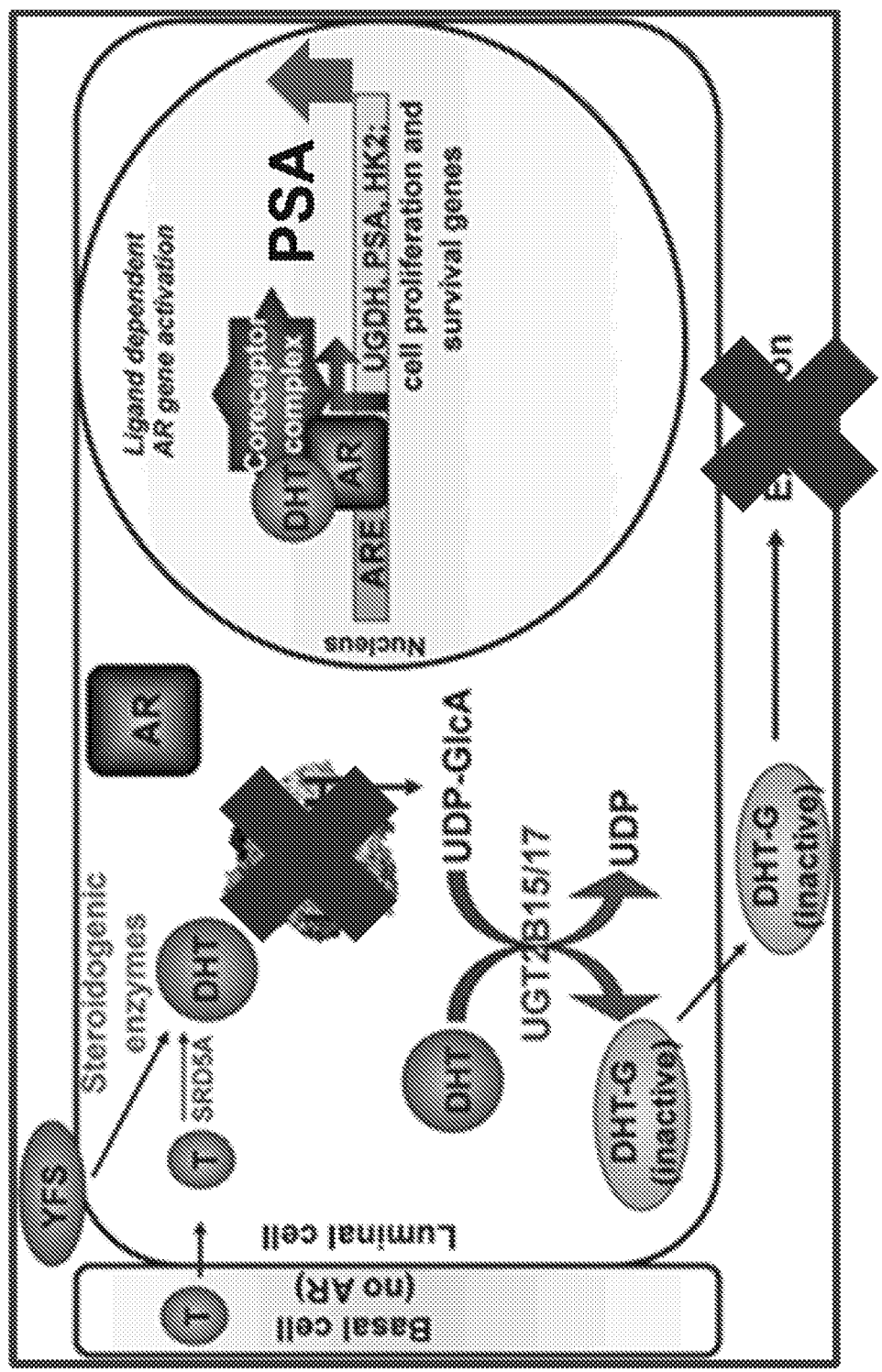
FIG. 5A is a diagram showing a mechanism wherein UGDH loss of activity may allow cells to sustain sensitivity to androgen deprivation.
Figure 5B:
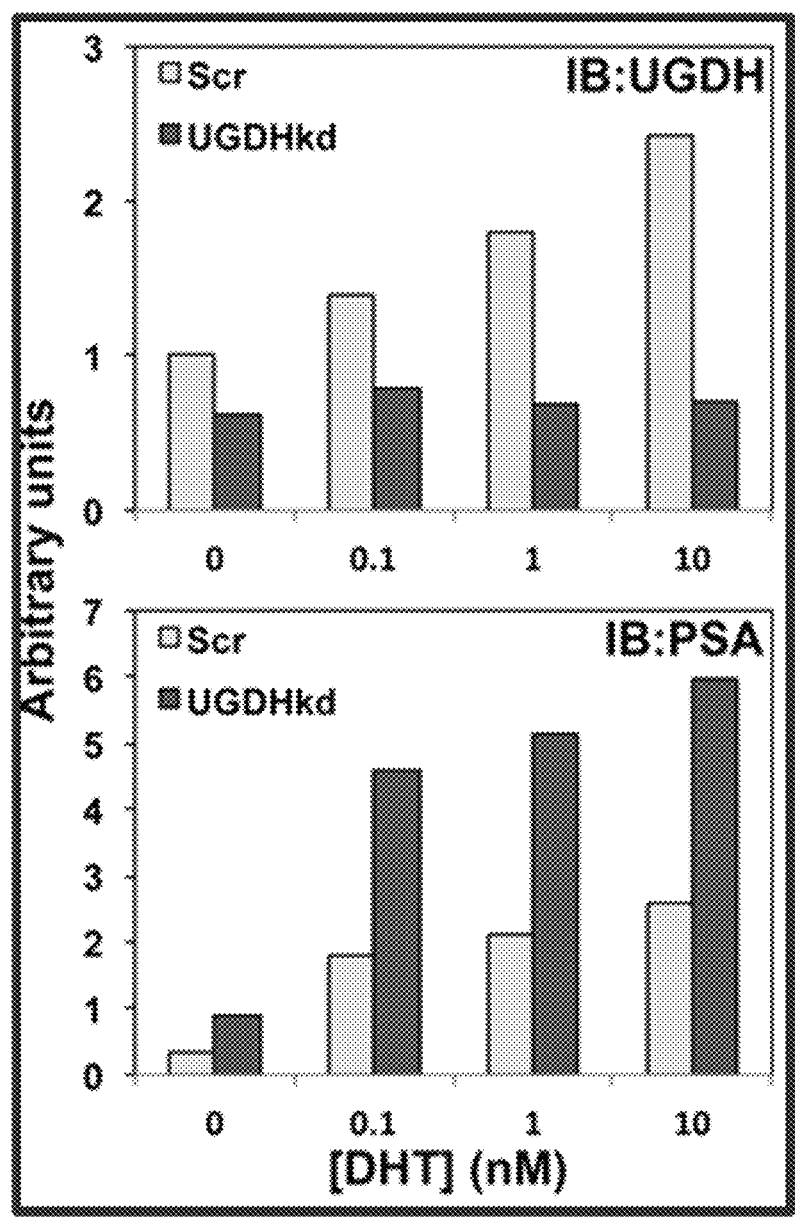
FIG. 5B shows data wherein UGDH knockdown lowers steroid dose required for AR gene expression.

FIG. 2 shows a diagram of UGDH providing precursors for androgen inactivation by UGT-mediated glucuronidation. To model androgen deprivation therapy in cell culture, cells were treated for two weeks in the absence or presence of androgen decrements. Cells were then treated with 10 nM DHT and analyzed by western blot for UGDH, PSA and AR, as shown in FIG. 3. AR promoter binding was modulated, so we further confirmed modulation of the AR using a luciferase reporter assay driven by the AR-stimulated PSA promoter/enhancer region, as shown in FIG. 4. FIG. 5A-5B shows that a loss of activity of UGDH may allow cells to sustain sensitivity to androgen deprivation.

Example 3

UGDH Kinetic Characterizations

Kinetic parameters of WT and mutant UGDH are shown below in Table 4. The $K_m$ and $V_{max}$ for the substrate (UDP-glucose) and cofactor (NAD+) was determined by a nonlinear regression fit of initial velocity vs. substrate/cofactor concentration. T325A and T325D are engineered inducible hexameric and obligate dimeric UGDH species, respectively.

TABLE 4

Kinetic parameters of WT and mutant UGDH

| | UDP-glucose | | NAD+ | |
|---|---|---|---|---|
| | $K_m$ (µM) | $V_{MAX}$ (nmol/min/mg) | $K_m$ (µM) | $V_{MAX}$ (nmol/min/mg) |
| WT-UGDH | 48.8 ± 5.5 | 240.9 ± 8.0 | 1031 ± 215 | 206.1 ± 13.0 |
| T325A-UGDH | 82.2 ± 9.6 | 260.8 ± 9.8 | 1682 ± 455 | 103 ± 8.5 |
| T325D-UGDH | 25.3 ± 4.0 | 63.1 ± 3.2 | 1203 ± 290 | 38.0 ± 2.5 |

Example 4

UGDH Inhibition Assay

Table 5 shows inhibition data for UDP-xylose, inhibitor (1) (i.e., 5210344), and inhibitor (31) (i.e., 6847944). $IC_{50}$ values for UDP-xylose and inhibitor (1) were determined using Km concentrations of UDP-glucose and NAD+ (50 µM UDP-glc and 1 mM NAD+). Ki values were determined by varying [UDP-glc] and holding NAD+ at saturating concentrations. UDP-xylose is a more potent inhibitor than the other compounds. Inhibitor (1) may have greatest effect on the dimer. Inhibitor (31) appears to require the ability for hexamer formation to inhibit which may suggest interference at the dimer-dimer interface as mechanism of action.

TABLE 5

Inhibition Data

| | UDP-xylose | | Inh #5210344 | | Inh #6847944 | |
|---|---|---|---|---|---|---|
| | $IC_{50}$ (µM) | $K_i$ (µM) | $IC_{50}$ (µM) | $K_i$ (µM) | $IC_{50}$ (µM) | $K_i$ (µM) |
| WT-UGDH | 0.58 ± 0.09 | 2.67 ± 0.54 | 260.7 ± 6.2 | ND* | 146.8 ± 1.05 | ND*** |
| T325A-UGDH | ND | ND | ND | 421.4 ± 117.6 | 86.98 ± 0.03 | ND |
| T325D-UGDH | ND | ND | ND | ND | 799.4 ± 0.05** | ND |

*Inhibitor (1) caused a synergistic product inhibition curve (very high Ki)
**Required 4 µM T325D in order to see effect instead of 1 µM
***Fit to allosteric sigmoidal curve which led to increased Hill coefficients

Example 5

UDP-xylose $K_i$ and $IC_{50}$ Determination

Figures 6A, 6B:
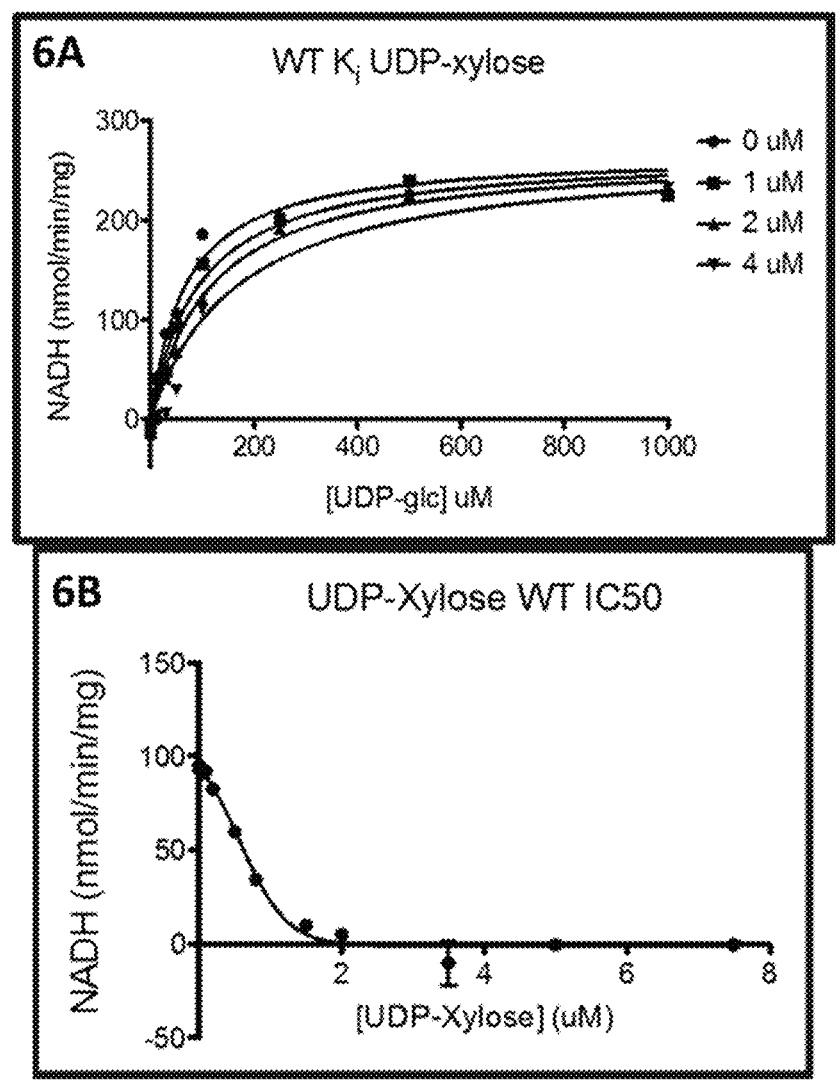
FIGS. 6A-6B shows a mixed-model inhibition fit for UDP-xylose used for determination of $K_i$.
Figure 7C:
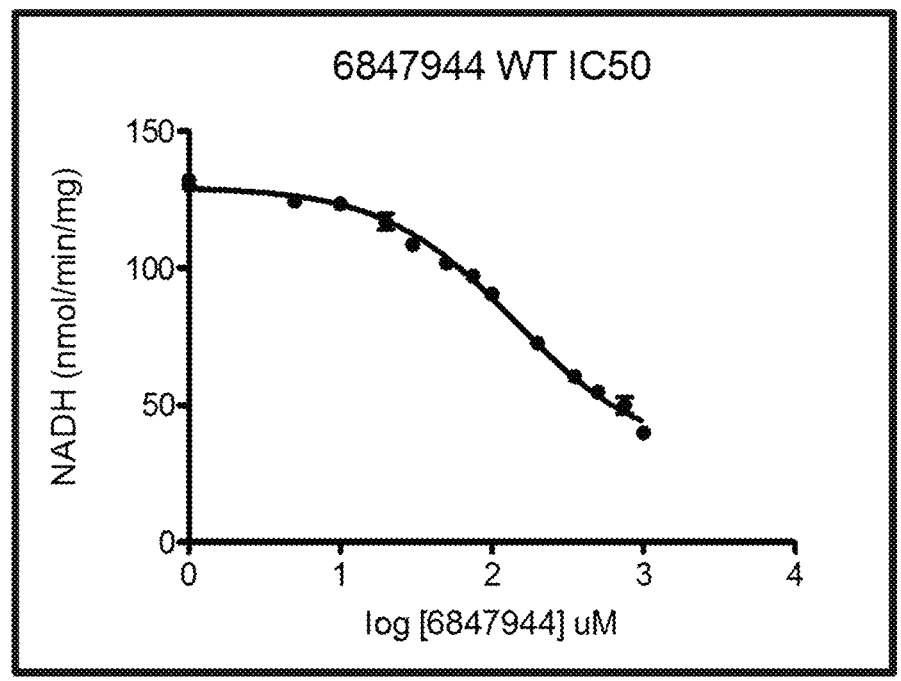
Figure 7D:
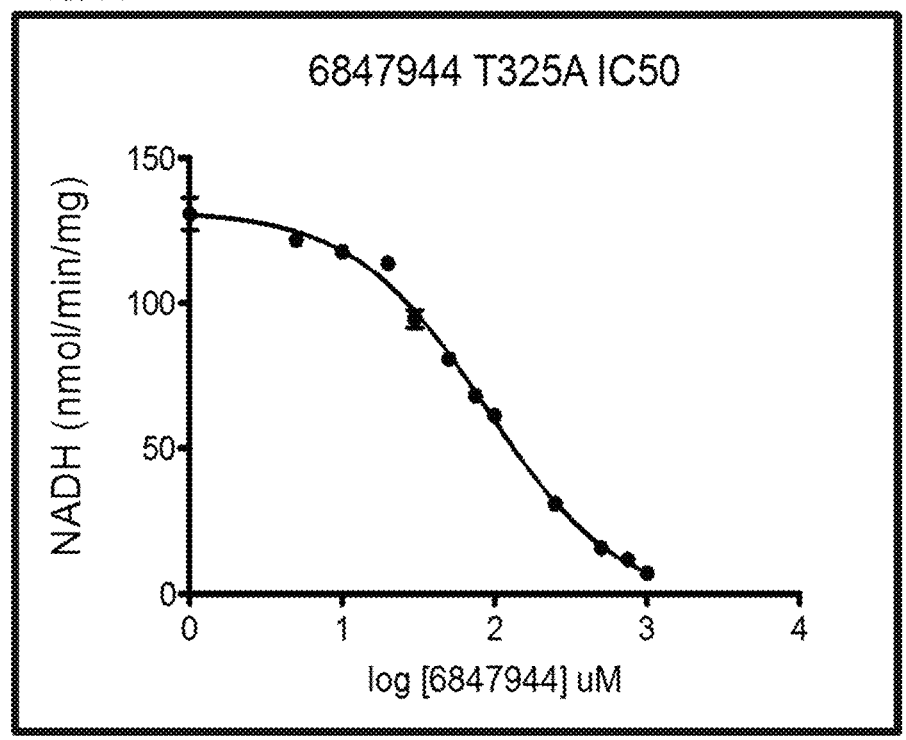
Figure 7E:
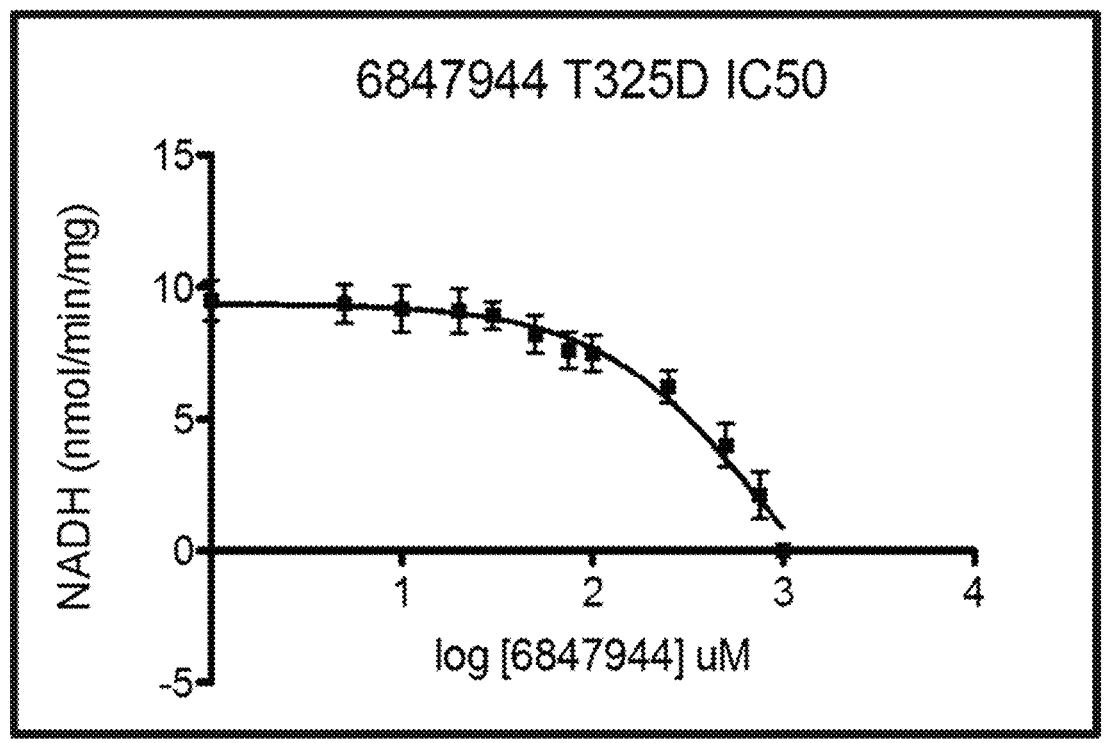
Figures 8A, 8B:
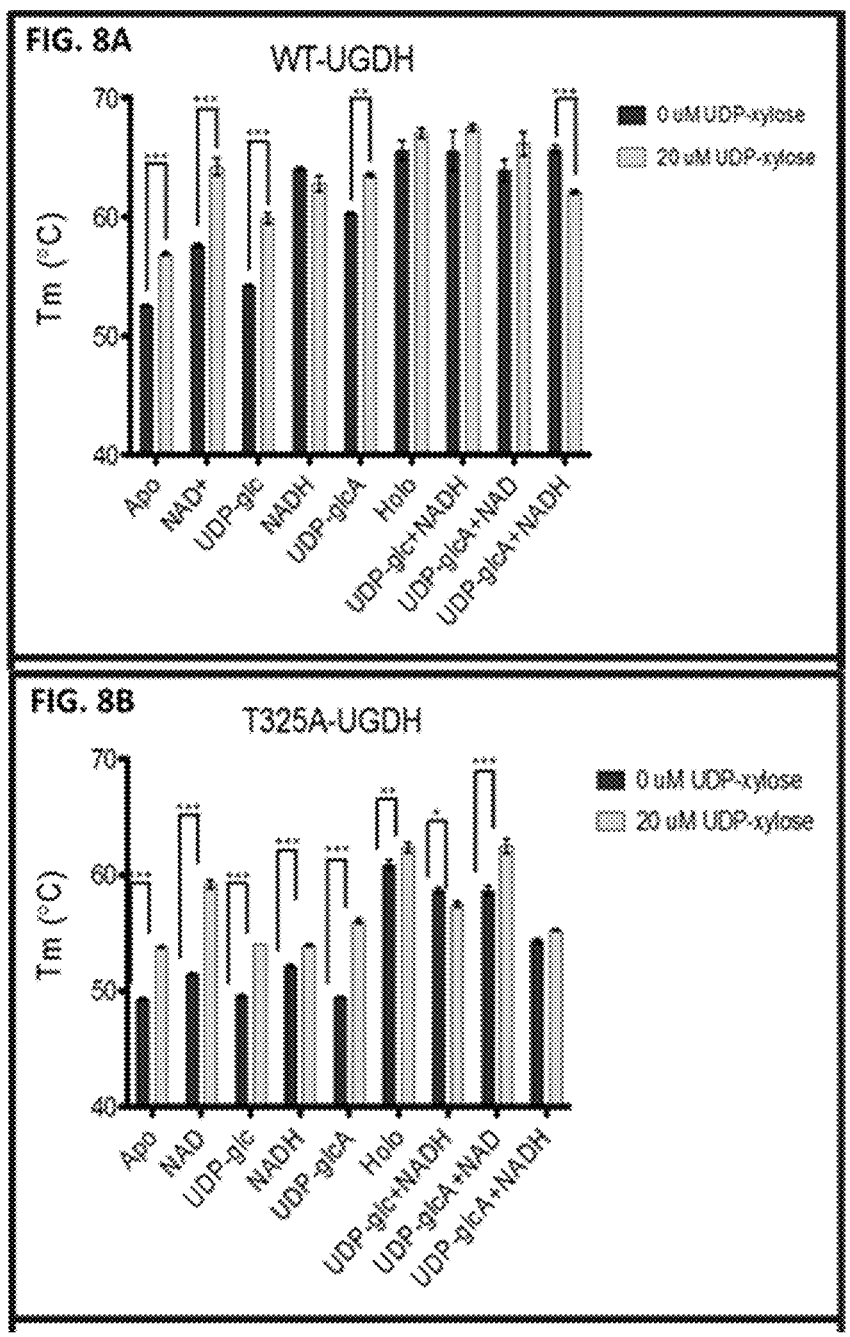
FIGS. 8A-8D show UDP-xylose effects on the thermal stability of WT, T325A (inducible hexamer), and T325D (obligate dimer) UGDH.
Figures 8C, 8D:
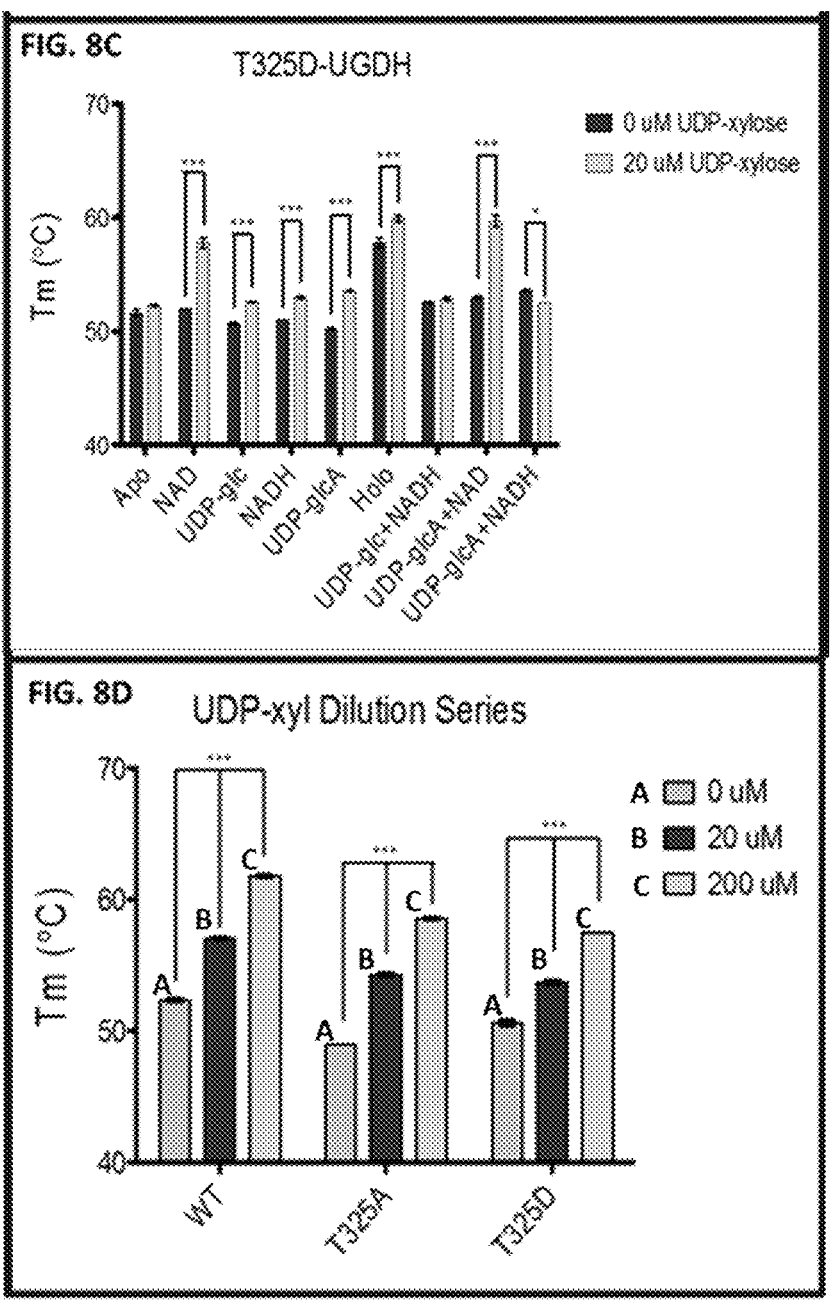
Figures 9A, 9B:
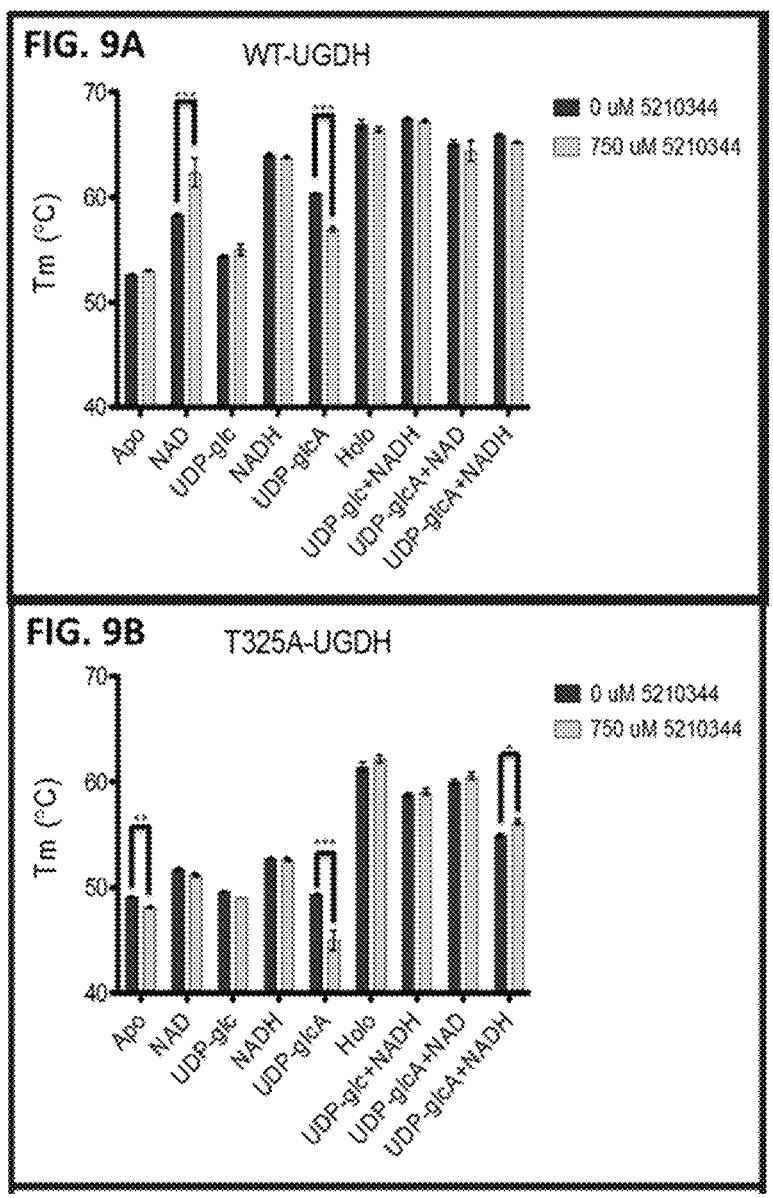
FIGS. 9A-9D shows inhibitor (1) effects on the thermal stability of WT, T325A (inducible hexamer), and T325D (obligate dimer) UGDH.
Figure 9C:
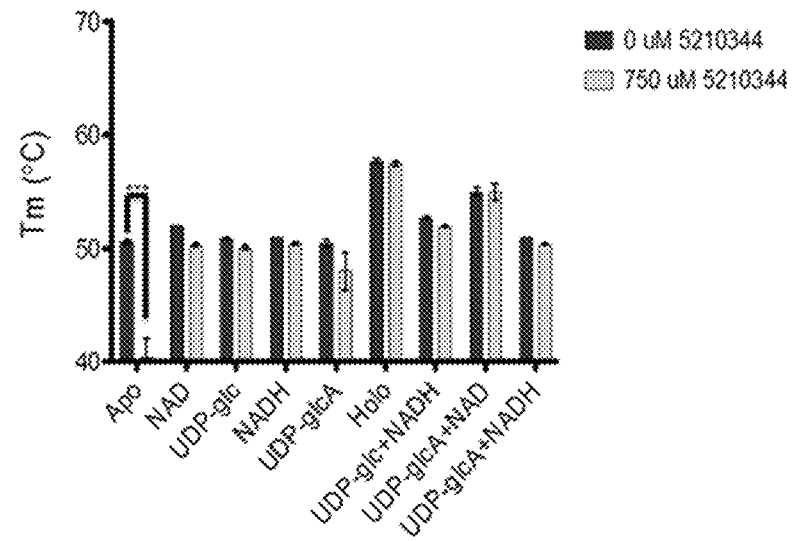
Figure 9D:
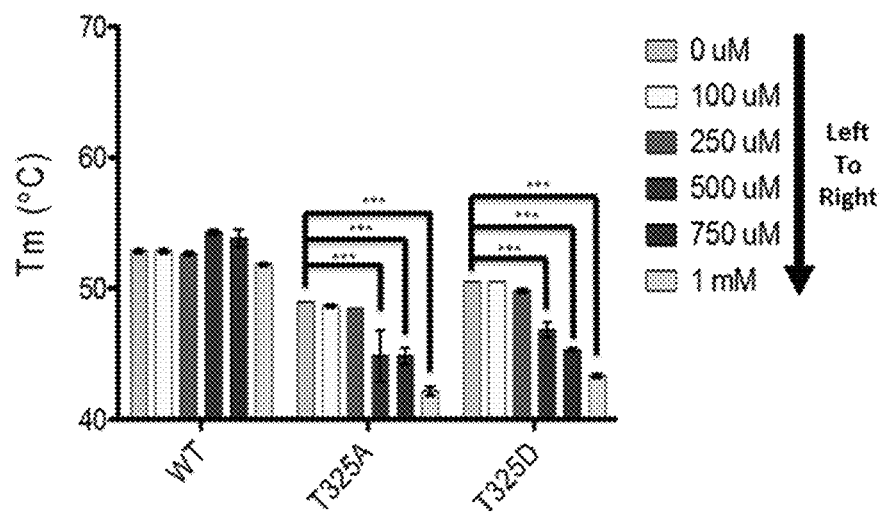

FIGS. 6A-6B show a mixed-model inhibition fit for UDP-xylose used for determination of $K_i$. UDP-xylose is a competitive inhibitor of UGDH ($K_i$=2.67±0.54 µM). $IC_{50}$ curve was performed as described above (see, e.g., Example 2) and was found to be 0.58±0.09 µM.

Example 6

Inhibitors $K_i$ and $IC_{50}$ Comparisons

FIG. 7A-7E show kinetic characterization of inhibitors (1) and (31). $IC_{50}$ experiments were performed as described above (see e.g., Example 2). Calculated $IC_{50}$ and $K_i$ values can be found in Table 5. Inhibitor (1) did not show inhibition in the WT K curve, but did with T325A which may support requirement of the dimer for inhibition. Inhibitor (31) is an allosteric inhibitor that may bind in the dimer-dimer interface or alter the interface to disrupt hexamer formation and inhibit the enzyme.

Example 7

Thermal Stability

UDP-Xylose Enhances Thermal Stability
FIG. 8A-8D show UDP-xylose effects on the thermal stability of WT, T325A (inducible hexamer), and T325D (obligate dimer) UGDH. The UDP-xylose inhibitor triggered multiple unfolding events of UGDH, and increased the thermal stability of apo WT and T325A, similarly to the effect of the UDP-sugar substrate and cofactor. UDP-xylose appears to significantly increase thermal stability of NAD+ complexes with WT, T325A, and T325D, similarly to the effect of the productive holo complexes. Statistical analyses were performed using a two-way ANOVA with Bonferroni post tests on PRISM.

Inhibitor (1) Selectively Affects Thermal Stability
FIG. 9A-9D shows inhibitor (1) (i.e., 5210344) effects on the thermal stability of WT, T325A (inducible hexamer), and T325D (obligate dimer) UGDH. The previously validated inhibitor appears to decrease thermal stability and cause multiple unfolding events of UDP-glcA complexes with WT, T325A, and T325D. This inhibitor also causes multiple unfolding events with the apo T325D and T325A mutants, which may indicate that this inhibitor can only bind to the dimeric form of UGDH in order to affect activity (supports the high $IC_{50}$ value with WT-UGDH).

Inhibitor (31) has Negligible Effect on Thermal Stability

Figures 10A, 10B:
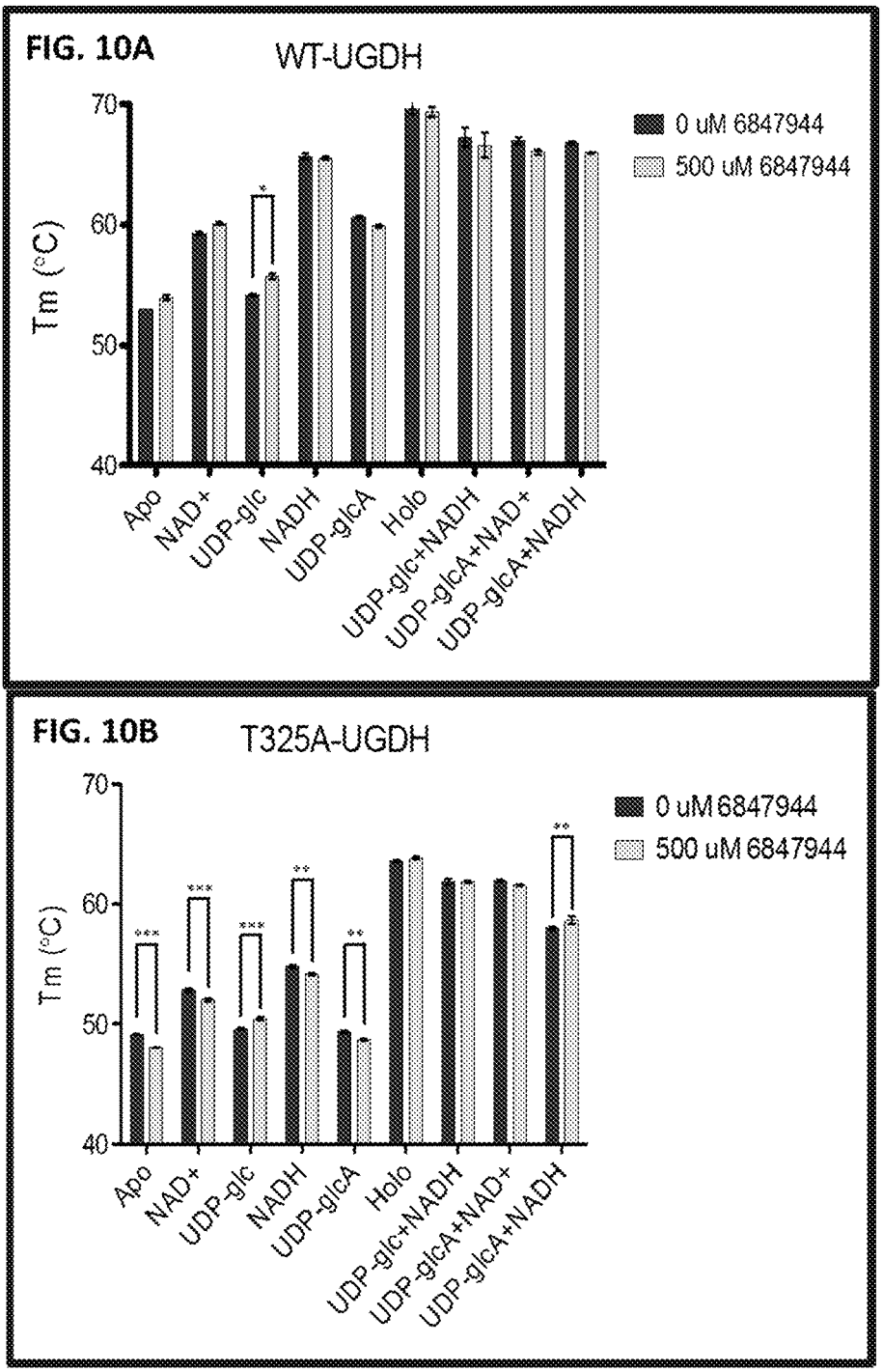
FIG. 10A-10C shows inhibitor (31) effects on the thermal stability of WT, T325A (inducible hexamer), and T325D (obligate dimer) UGDH.
Figure 10C:
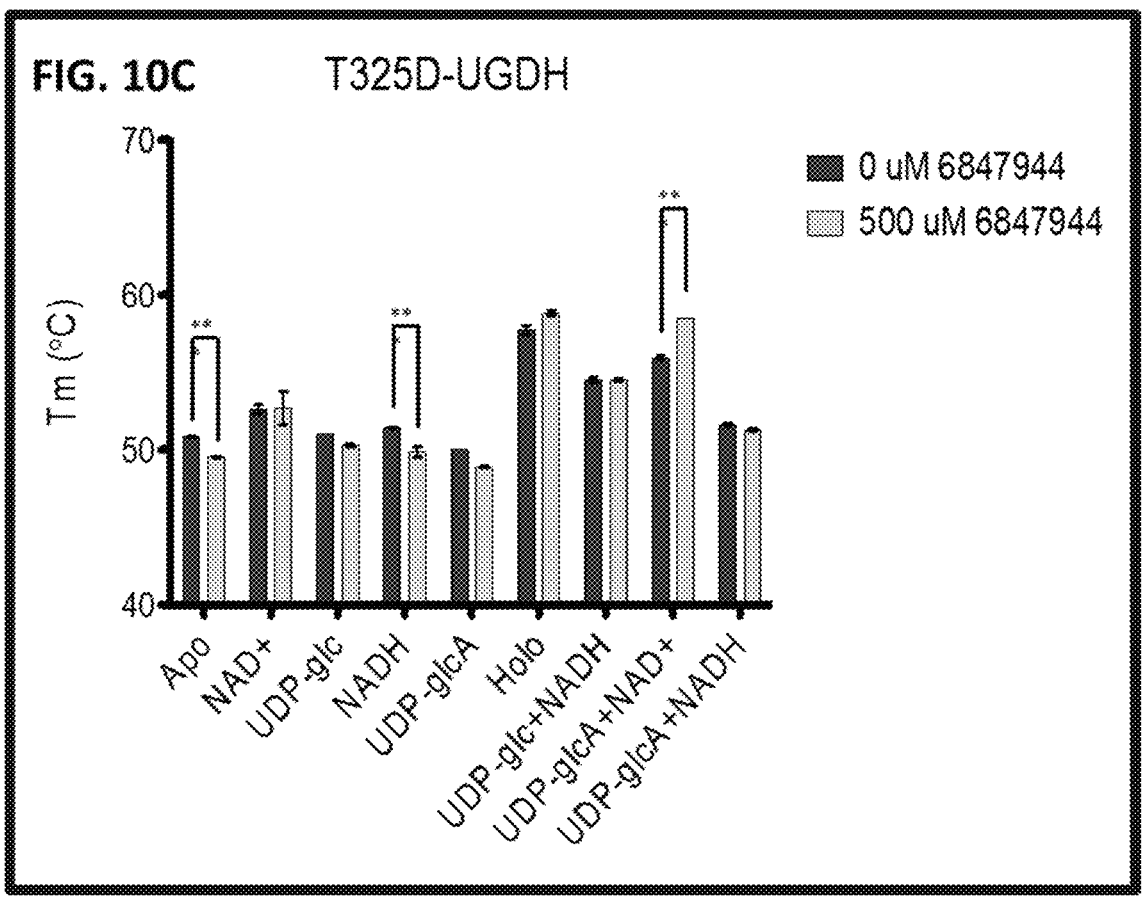

FIG. 10A-10C shows inhibitor (31) (i.e., 6847944) effects on the thermal stability of WT, T325A (inducible hexamer), and T325D (obligate dimer) UGDH. This modestly affects the T325A and T325D mutants by decreasing thermal stability of all binary complexes except UDP-glucose.

Example 8

Trypsin Sensitivity

Figure 11:
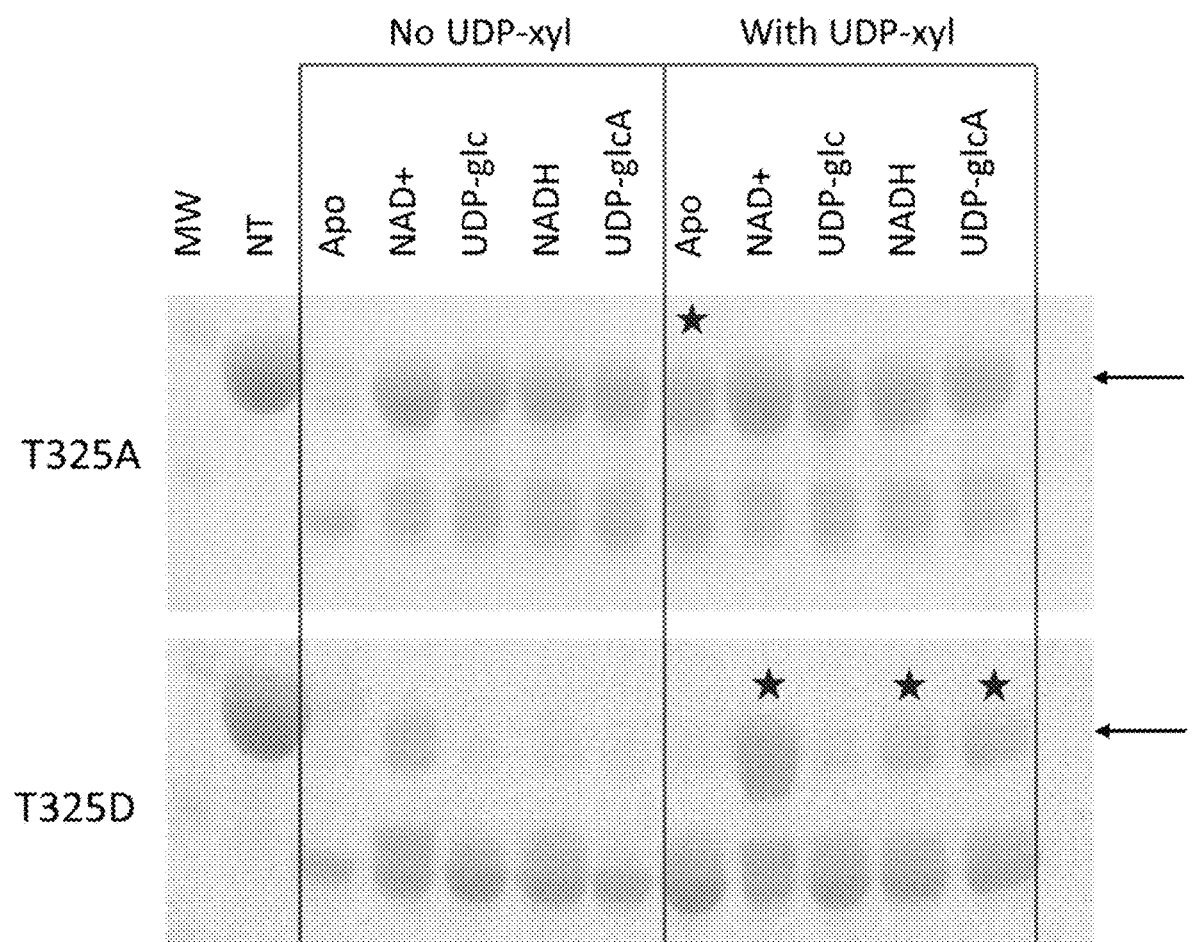
FIG. 11 shows UDP-xylose stabilizing UGDH T325A and T325D mutants against limited trypsin proteolysis.

UDP-xylose stabilizes UGDH T325A and T325D mutants against limited trypsin proteolysis, as shown in FIG. 11. UDP-xylose [20 µM] protected T325A apo from trypsin digestion (red star) and only slightly affected the other forms. UDP-xylose [20 µM] also significantly protected T325D complexes with NAD+, NADH, and UDP-glcA, but did not affect the apo and UDP-glc forms. Each assay contained 10 µg of enzyme, 10 ng Trypsin, and combinations of substrate, cofactor, and UDP-xylose, which was incubated 2.5 h, followed by SDS-PAGE.

Example 9

Proteolysis

Figure 12:
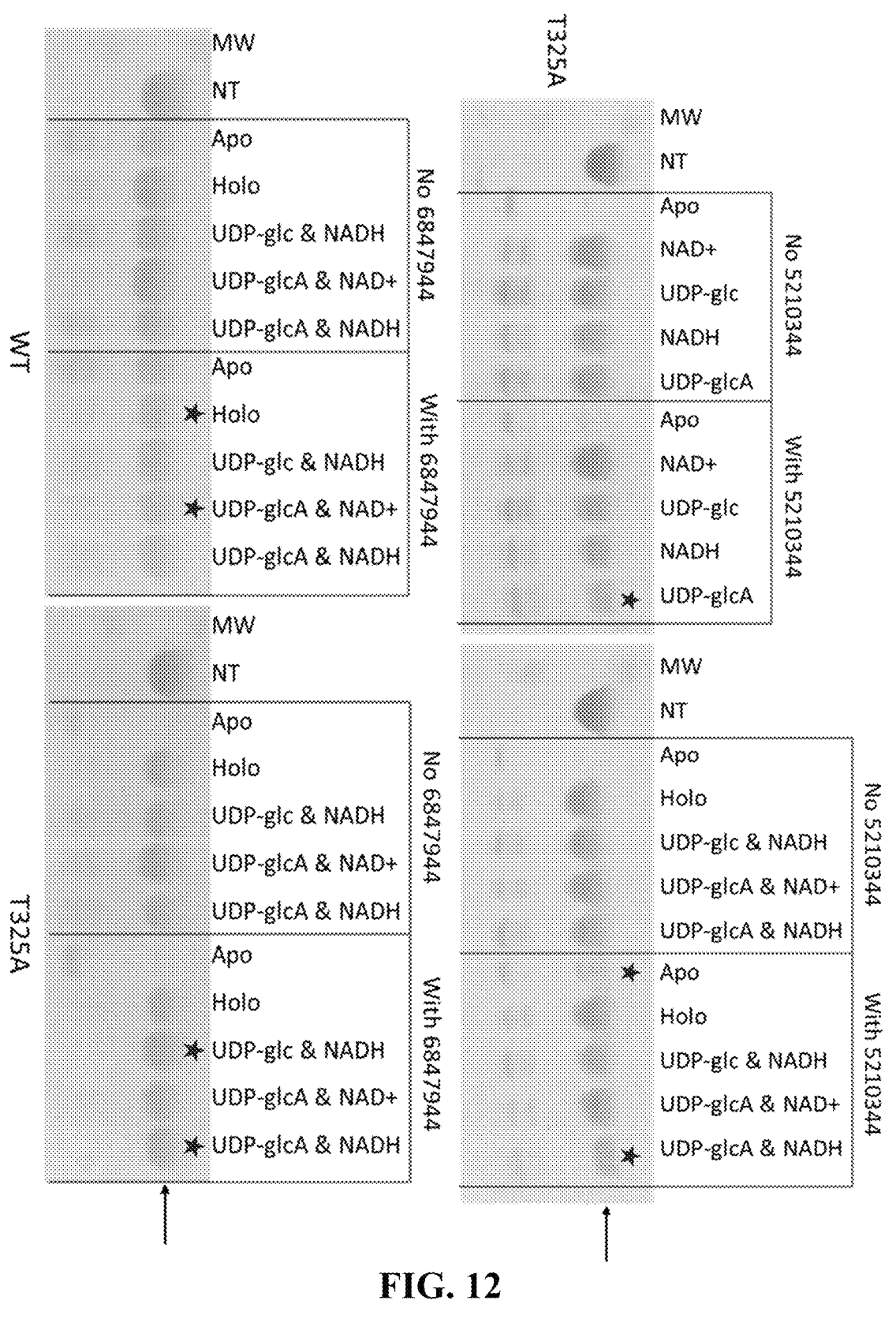

FIG. 12 shows inhibitor (1) and (31) effects on trypsin digestion of WT and mutant UGDH. Inhibitor (1) [750 µM] significantly affects trypsin digestion of T325A with UDP-glcA and UDP-glcA with NADH. 6847944 [500 µM] significantly affects ternary complexes for both WT and T325A. The same procedures from above (see e.g., Example 7) were followed.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:
1. A method of treating prostate cancer, comprising administering to a patient in need thereof a therapeutically effective amount of a compound selected from the group consisting of:

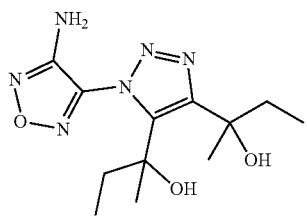

-continued

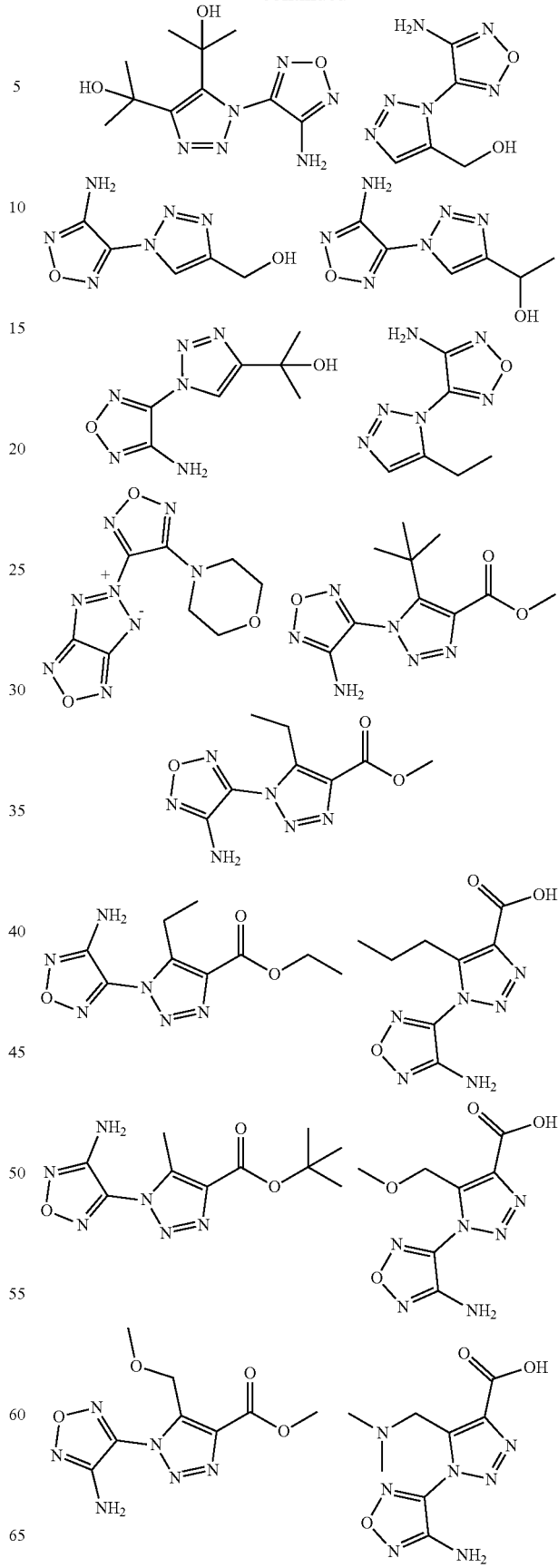

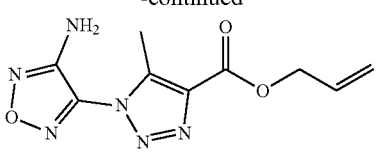
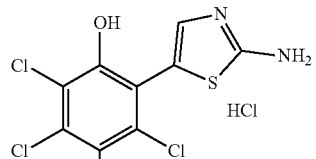
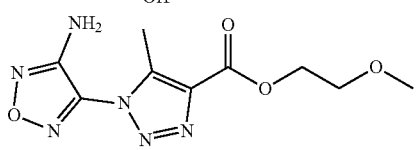
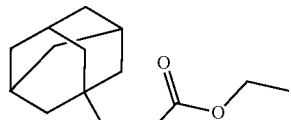
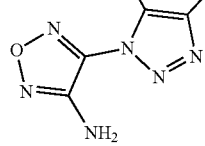
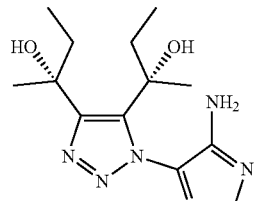
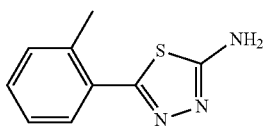
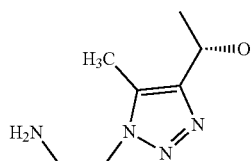
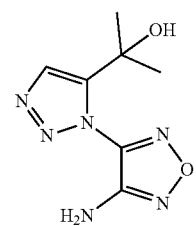
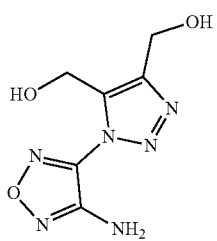
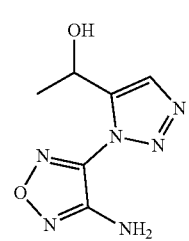
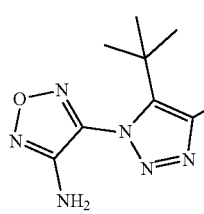
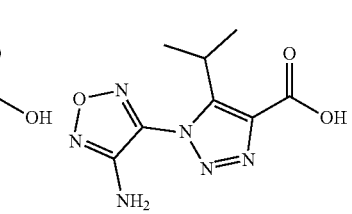
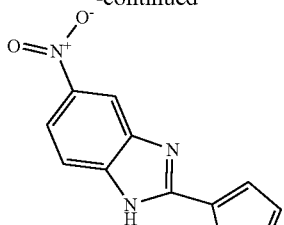
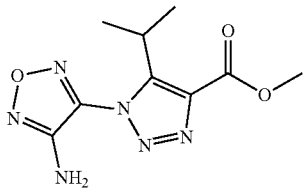
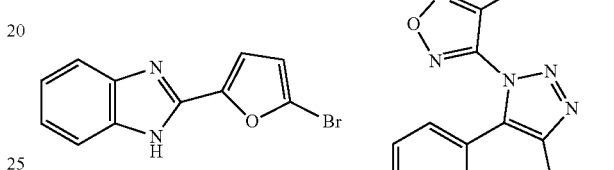
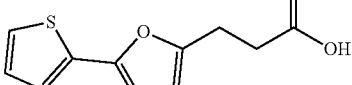
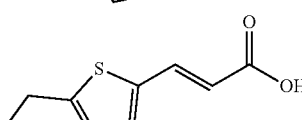
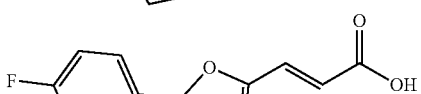
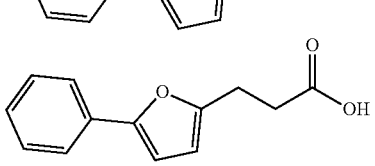
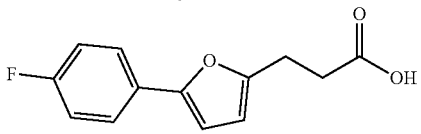
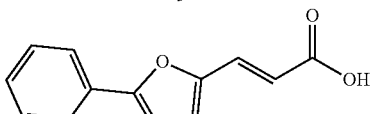
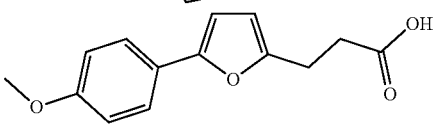
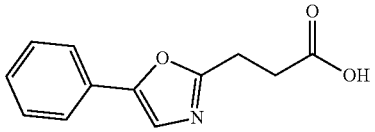

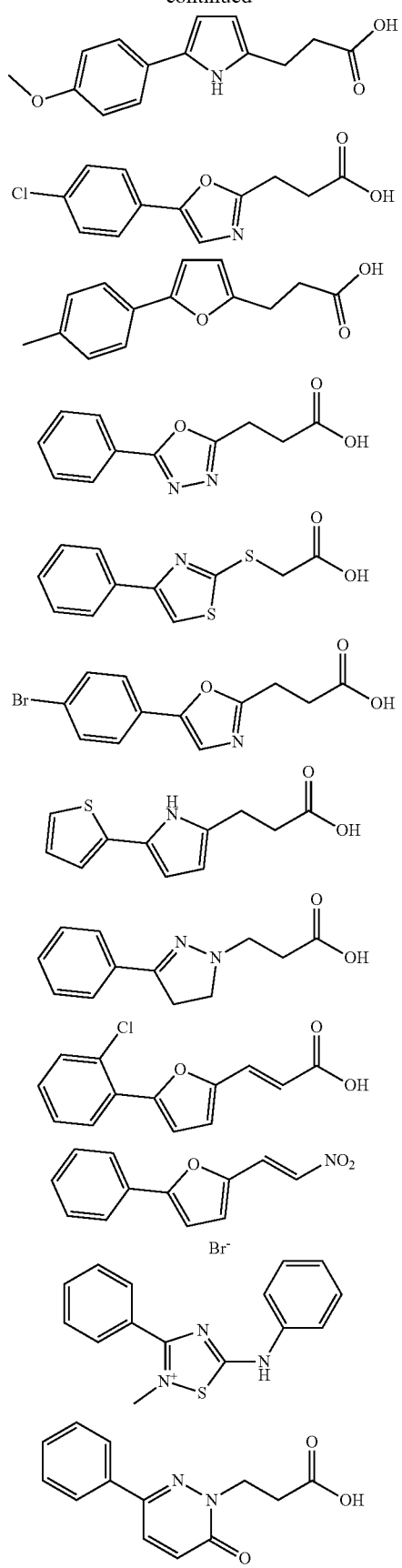
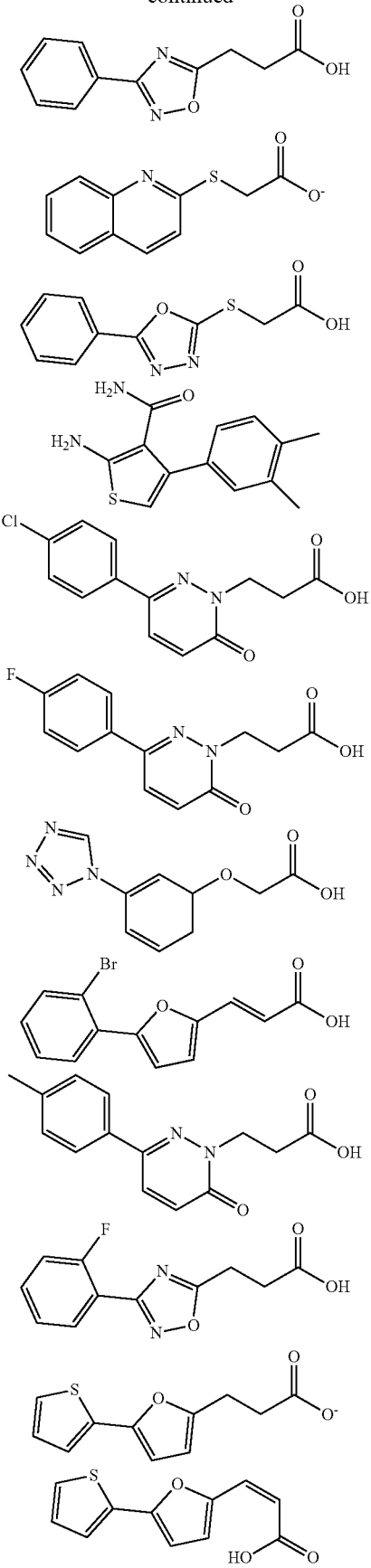

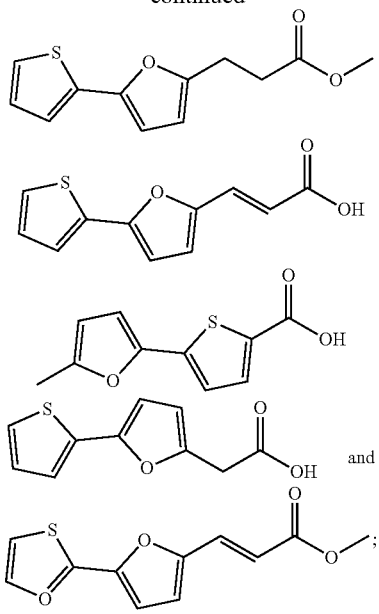

or a pharmaceutically acceptable salt thereof.

2. The method of claim 1, wherein the compound is administered in combination with one or more additional therapies comprising administration of a chemotherapeutic agent, androgen deprivation therapy, or a combination thereof.

3. The method of claim 1, wherein the compound is selected from the group consisting of 2,2'-[1-(4-amino-1,2, 5-oxadiazol-3-yl)-1H-1,2,3-triazole-4,5-diyl]di(2-butanol) (1), or a pharmaceutically acceptable salt thereof, and 3-[5-(2-thienyl)-2-furyl]propanoic acid (31), or a pharmaceutically acceptable salt thereof.

4. The method of claim 1, wherein the prostate cancer is mediated by UDP-glucose dehydrogenase (UGDH).

5. The method of claim 4, wherein the compound is selected from the group consisting of 2,2'-[1-(4-amino-1,2, 5-oxadiazol-3-yl)-1H-1,2,3-triazole-4,5-diyl]di(2-butanol) (1), or a pharmaceutically acceptable salt thereof, and 3-[5-(2-thienyl)-2-furyl]propanoic acid (31), or a pharmaceutically acceptable salt thereof.

6. The method of claim 1, wherein the prostate cancer is castration resistant prostate cancer (CRPC).

7. The method of claim 1, wherein the compound is 2,2'-[1-(4-amino-1,2,5-oxadiazol-3-yl)-1H-1,2,3-triazole-4, 5-diyl]di(2-butanol) (1), or a pharmaceutically acceptable salt thereof.

8. The method of claim 1, wherein the compound is 3-[5-(2-thienyl)-2-furyl]propanoic acid (31), or a pharmaceutically acceptable salt thereof.

9. The method of claim 2, wherein the compound is 2,2'-[1-(4-amino-1,2,5-oxadiazol-3-yl)-1H-1,2,3-triazole-4, 5-diyl]di(2-butanol) (1), or a pharmaceutically acceptable salt thereof.

10. The method of claim 2, wherein the compound is 3-[5-(2-thienyl)-2-furyl]propanoic acid (31), or a pharmaceutically acceptable salt thereof.

11. The method of claim 4, wherein the compound is 2,2'-[1-(4-amino-1,2,5-oxadiazol-3-yl)-1H-1,2,3-triazole-4, 5-diyl]di(2-butanol) (1), or a pharmaceutically acceptable salt thereof.

12. The method of claim 4, wherein the compound is 3-[5-(2-thienyl)-2-furyl]propanoic acid (31), or a pharmaceutically acceptable salt thereof.

13. A method of treating castration resistant prostate cancer (CRPC), comprising administering to a patient in need thereof a therapeutically effective amount a compound which is 2,2'-[1-(4-amino-1,2,5-oxadiazol-3-yl)-1H-1,2,3-triazole-4,5-diyl]di(2-butanol) (1), or a pharmaceutically acceptable salt thereof.

14. The method of claim 13, wherein the compound is administered in combination with one or more additional therapies comprising administration of a chemotherapeutic agent, androgen deprivation therapy, or a combination thereof.

15. A method of treating castration resistant prostate cancer (CRPC), comprising administering to a patient in need thereof a therapeutically effective amount a compound which is 345-(2-thienyl)-2-furyl]propanoic acid (31), or a pharmaceutically acceptable salt thereof.

16. The method of claim 15, wherein the compound is administered in combination with one or more additional therapies comprising administration of a chemotherapeutic agent, androgen deprivation therapy, or a combination thereof.

17. A method of treating castration resistant prostate cancer (CRPC) mediated by UDP-glucose dehydrogenase (UGDH), comprising administering to a patient in need thereof a therapeutically effective amount a compound selected from the group consisting of 2,2'-[1-(4-amino-1,2, 5-oxadiazol-3-yl)-1H-1,2,3-triazole-4,5-diyl]di(2-butanol) (1), or a pharmaceutically acceptable salt thereof, and 3-[5-(2-thienyl)-2-furyl]propanoic acid (31), or a pharmaceutically acceptable salt thereof.

18. The method of claim 17, wherein the compound is administered in combination with one or more additional therapies comprising administration of a chemotherapeutic agent, androgen deprivation therapy, or a combination thereof.

* * * * *

UNITED STATES PATENT AND TRADEMARK OFFICE
CERTIFICATE OF CORRECTION

PATENT NO. : 11,478,457 B2  Page 1 of 2
APPLICATION NO. : 15/136419
DATED : October 25, 2022
INVENTOR(S) : Melanie A. Simpson and Joseph Barycki It is certified that error appears in the above-identified patent and that said Letters Patent is hereby corrected as shown below:

In the Claims

In Column 86, approximately Lines 2-8, in Claim 1, after " 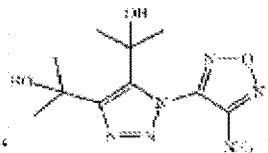 " please insert -- 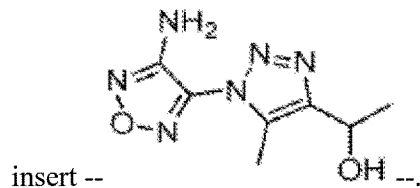 --.

In Column 90, approximately Lines 36-41, in Claim 1, delete " 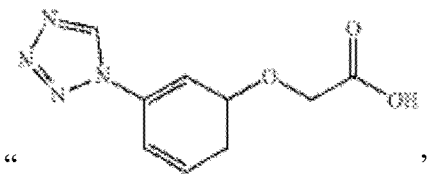 " and insert -- 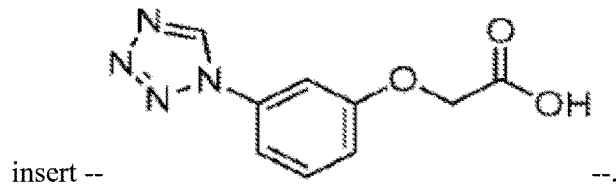 --.

Signed and Sealed this
Thirty-first Day of January, 2023

Katherine Kelly Vidal
*Director of the United States Patent and Trademark Office*

In Column 91, approximately Lines 20-24, in Claim 1, delete
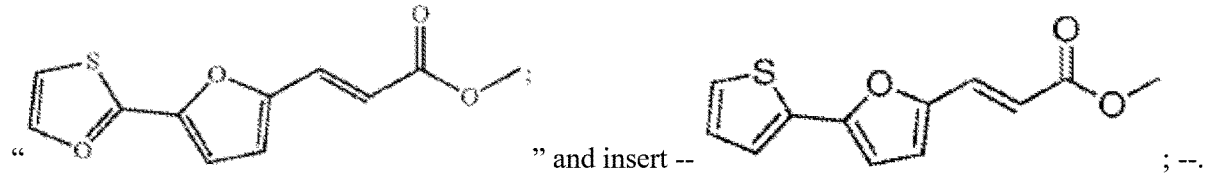
In Column 92, Line 19, in Claim 13, after "amount" insert -- of --.
In Column 92, Line 30, in Claim 15, after "amount" insert -- of --.
In Column 92, Line 31, in Claim 15, delete "345" and insert -- 3-[5 --.
In Column 92, Line 41, in Claim 17, after "amount" insert -- of --.